US010722529B2

(12) United States Patent
Rappaport et al.

(10) Patent No.: US 10,722,529 B2
(45) Date of Patent: Jul. 28, 2020

(54) MODULATION OF NAD+ METABOLIC PATHWAYS FOR TREATMENT OF DISEASE

(71) Applicant: Temple University—Of The Commonwealth System of Higher Education, Philadelphia, PA (US)

(72) Inventors: Jay F. Rappaport, Wynnewood, PA (US); Xuebin Qin, Westwood, MA (US); Stephani Velasquez, Philadelphia, PA (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 15/780,664

(22) PCT Filed: Dec. 2, 2016

(86) PCT No.: PCT/US2016/064748
§ 371 (c)(1),
(2) Date: Jun. 1, 2018

(87) PCT Pub. No.: WO2017/096246
PCT Pub. Date: Jun. 8, 2017

(65) Prior Publication Data
US 2018/0353526 A1  Dec. 13, 2018

Related U.S. Application Data

(60) Provisional application No. 62/262,739, filed on Dec. 3, 2015, provisional application No. 62/413,120, filed on Oct. 26, 2016.

(51) Int. Cl.
| | |
|---|---|
| A61K 31/706 | (2006.01) |
| C07H 19/048 | (2006.01) |
| A61P 31/18 | (2006.01) |
| A61K 31/353 | (2006.01) |
| A61K 39/395 | (2006.01) |
| A61K 45/06 | (2006.01) |

(52) U.S. Cl.
CPC .......... *A61K 31/706* (2013.01); *A61K 31/353* (2013.01); *A61K 39/3955* (2013.01); *A61K 45/06* (2013.01); *A61P 31/18* (2018.01); *C07H 19/048* (2013.01)

(58) Field of Classification Search
None
See application file for complete search history.

(56) References Cited

U.S. PATENT DOCUMENTS

| | | |
|---|---|---|
| 2011/0009372 A1 | 1/2011 | Frincke |
| 2011/0110913 A1 | 5/2011 | Grant |
| 2012/0328526 A1 | 12/2012 | Kristian |
| 2014/0363411 A1 | 12/2014 | Eisenbach-Schwartz |
| 2015/0175645 A1 | 6/2015 | Milburn |

OTHER PUBLICATIONS

Baker et al., Critical appraisal of animal models of multiple sclerosis, 2011, Multiple Sclerosis Journal 17(6):647-657 (Year: 2011).*
Benatar, M., Lost in translation: Treatment trials in the SOD1 mouse and in human ALS, 2007, Neurobiology of Disease 26:1-13 (Year: 2007).*
DiBernardo et al., Translating preclinical insights into effective human trials in ALS, 2006, Biochimica et Biophysica Acta 1762:1139-1149 (Year: 2006).*
Gong et al., Nicotinamide riboside restores cognition through an upregulation of proliferator-activated receptor-g coactivator 1a regulated b-secretase 1 degradation and mitochondrial gene expression in Alzheimer's mouse models, 2013, Neurobiology of Aging 34:1581e1588 (Year: 2013).*
Asghar et al., "Indoleamine 2,3-Dioxygenase Expression and Activity in Patients with Hepatitis C Virus-Induced Liver Cirrhosis" Exp Ther Med. 2015, 9:901-904.
Barth et al., "Persistent Infectious Diseases Say—IDO. Role of Indoleamine-2,3-Dioxygenase in Disease Pathogenesis and Implications for Therapy" Grit Rev Microbiol. 2014, 40:360-368.
Bieganowski et al., "Discoveries of Nicotinamide Riboside as a Nutrient and Conserved NRK Genes Establish a Preiss-Handler Independent Route to NAD+ in Fungi and Humans" Cell, 2004, 117:495-502.
Boasso et al., "How Does Indoleamine 2,3-Dioxygenase Contribute to HIV-Mediated Immune Dysregulation" Curr Drug Metab. 2007, 8:217-223.
Bofill et al., "T-lymphocytes from AIDS patients are unable to synthesize ribonucleotides de novo in response to mitogenic stimulation. Impaired pyrimidine responses are already evident at early stages of HIV-1 infection" J Biol Chem. 1995, 270:29690-29697.
Cassol et al., "Cerebrospinal fluid metabolomics reveals altered waste clearance and accelerated aging in HIV patients with neurocognitive impairment" AIDS. 2014, 28:1579-1591.
Grohmann et al., "Tolerance, DCs and Tryptophan: Much Ado about IDO" Trends Immunol. 2003, 24:242-248.
Hassa et al., "Nuclear ADP-ribosylation reactions in mammalian cells: where are we today and where are we going?" Microbiol Mol Biol Rev. 2006, 70:789-829.
Jenabian et al., "Influence of Hepatitis C Virus Sustained Virological Response on Immunosuppressive Tryptophan Catabolism in ART-Treated HIV/HCV Coinfected Patients" J Acquir Immune Defic Syndr. 2016, 71:254-262.
Mellor et al., "Creating Immune Privilege: Active Local Suppression that Benefits Friends, but Protects Foes" Nat Rev Immunol. 2008, 8:74-80.
Mellor et al., "Tryptophan Catabolism and T-cell Tolerance: Immunosuppression by Starvation?" Immunol Today. 1999, 20:469-473.
Mouchiroud et al., "NAD+ Metabolism: a Therapeutic Target for Age-Related Metabolic Disease" Crit Rev Biochem Mol Biol. 2013, 48:397-408.
Murray et al., "Increased plasma tryptophan in HIV-infected patients treated with pharmacologic doses of nicotinamide" Nutrition. 2001;17:654-656.

(Continued)

*Primary Examiner* — John D Ulm
(74) *Attorney, Agent, or Firm* — Riverside Law LLP

(57) ABSTRACT

The present invention encompasses compositions and methods for regulating the kynurenine to tryptophan ratio, NAD+ level and CD16 expression for the treatment diseases.

4 Claims, 33 Drawing Sheets

(56) References Cited

OTHER PUBLICATIONS

Nemeth et al., "Kynurenines in the Central Nervous System: Recent Developments" Central Nervous System Agents in Medicinal Chemistry, 2007, 7:45-56.
Prodinger et al., "The Tryptophan Metabolite Picolinic Acid Suppresses Proliferation and Metabolic Activity of CD4+ T Cells and Inhibits c-Myc Activation" J Leukoc Biol. 2016, 99:583-594.
Schmidt et al., "New Insights into IDO Biology in Bacterial and Viral Infections" Front Immunol. 2014, 5:384, 12 pages.
Vacchelli et al., "Trial Watch: IDO Inhibitors in Cancer Therapy" Oncoimmunology, 2014, 3:e957994, 10 pages.

* cited by examiner

B

MODULATION OF NAD+ METABOLIC PATHWAYS FOR TREATMENT OF DISEASE

CROSS-REFERENCE TO RELATED APPLICATIONS

This application is the U.S. national phase application filed under 35 U.S.C. § 371 claiming benefit to International Patent Application No. PCT/US2016/064748, filed on Dec. 2, 2016, which is entitled to priority under 35 U.S.C. § 119(e) to U.S. Provisional Application No. 62/262,739, filed Dec. 3, 2015, and U.S. Provisional Application No. 62/413,120, filed Oct. 26, 2016, the disclosures of which are incorporated herein by reference in their entirety.

STATEMENT REGARDING FEDERALLY SPONSORED RESEARCH OR DEVELOPMENT

This invention was made with government support under P01MH105303-01 R01MH090910 and 5R01MH101010-03 awarded by the National Institutes of Health. The government has certain rights in the invention.

BACKGROUND OF THE INVENTION

The essential amino acid tryptophan (TRP) is a precursor for the synthesis of nicotinamide adenine dinucleotide (NAD+) and serotonin. TRP is metabolized by two pathways the kynurenine (KYN) pathway resulting in NAD and the methoxyindole pathway which generates serotonin and melatonin. The KYN pathway is important in controlling immune function in the setting of inflammation, since kynurenine metabolites exhibit immune suppressive activity. Furthermore, the downstream product quinolinic acid exhibits neurotoxic properties and is likely involved in neuronal injury in a variety of central nervous system diseases. Excess tryptophan catabolism likely depletes the necessary tryptophan needed for the biosynthesis of serotonin, potentially leading to depression, and melatonin, potentially leading to sleep disorders. An increased kynurenine to tryptophan ratio has been observed and implicated in the pathogenesis of several disease states including cardiovascular disease, Alzheimer's disease, amyotrophic lateral sclerosis, Huntington's disease, Parkinson's disease, stroke and epilepsy (Central Nervous System Agents in Medicinal Chemistry, 2007, 7, 45-56), malaria, cancer, depression, schizophrenia, obesity, eating disorders, metabolic syndrome, insulin resistance, diabetes, osteoporosis, rheumatoid arthritis, migraine, systemic lupus erythematosus, and HIV infection. In HIV infection, increased tryptophan catabolism has been implicated in immunopathogenesis as well as comorbid conditions associated with HIV/AIDS. Notably, depression and sleep disorders are common comorbidities in HIV infection. The metabolism of tryptophan has critical relevance in pregnancy (survival of the allogeneic conceptus/fetus), transplant biology, cancer therapeutics, as well as normal immunologic control (Mellor and Munn, Immunol Today. 1999, 20:469-473, Grohmann et al., Trends Immunol. 2003, 24:242-248).

The initial, rate-limiting step in the kynurenine pathway is performed by heme-containing oxidoreductase enzymes, including indoleamine 2,3-dioxygenase (IDO). Increased production of the enzyme IDO is exhibited in cancers, as a consequence of inflammatory signals such as interferons, NFkB activation, and TNF alpha, as well as the combined stimulus of LPS. With IDO promoting the rate limiting step in tryptophan breakdown, this process leads to reduced local levels of tryptophan as well as increased kynurenine metabolites (Prodinger et al., J Leukoc Biol. 2016, 99:583-594) that both contribute to immune suppression and HIV associated pathogenesis. The mechanism whereby regulatory myeloid cells degrade tryptophan as well as arginine (via arginase 1 in M2 macrophages) results in the accumulation of uncharged tRNAs in T cells, activation of GCN2 kinase in naïve and regulatory T cells, resulting in immune suppression via inhibition of effector T cell function (Boasso and Shearer, Curr Drug Metab. 2007, 8:217-223; Mellor and Munn, Nat Rev Immunol. 2008, 8:74-80; Barth and Raghuraman, Crit Rev Microbiol. 2014, 40:360-368; Schmidt and Schultze, Front Immunol. 2014, 5:384). The inhibition of tryptophan catabolism is therefore an important target for immune modulation; IDO is the subject of intense investigation in clinical trials for cancer (Vacchelli et al., Oncoimmunology, 2014, 3:e957994).

Although NAD+ can be synthesized from dietary precursors (such as niacin) through salvage pathways, TRP catabolism is required for the de novo synthesis of $NAD^+$. $NAD^+$ is involved in virtually all biological processes, including energy transfer, and is the active subject of investigation for therapeutics in many diseases which include Parkinson's disease, Alzheimer's disease, cardiovascular disease as well as aging (Mouchiroud et al., Crit Rev Biochem Mol Biol. 2013, 48:397-408). $NAD^+$ is required for the action of Sirtuin deacetylases, where their action is dependent upon the availability of $NAD^+$. Strategies that either increase $NAD^+$ production via niacin related salvage pathways and/or strategies that prevent $NAD^+$ consumption/degradation by downstream pathways are the subject of intense interest as therapeutic strategies for age related diseases.

HIV infection is associated with increased TRP metabolism as determined by elevated kynurenine to tryptophan ratio, which often incompletely resolves in the context of antiviral therapy. Continued elevations in the kynurenine to tryptophan ratio is associated with $CD4^+$ T cell decline, more rapid decline in CD4/CD8 ratios, and the development of comorbidities associated with HIV infection including cardiovascular disease, HIV associated neurocognitive disorder (HAND), depression and sleep disorders.

HIV enters the central nervous system within the first weeks of infection. A mature $CD14^+$ $CD16^+$ monocyte subset may contribute to HAND by transporting virus into the CNS, by serving as a target for HIV infection in the CNS, contributing to inflammation and vascular injury within blood vessels and CNS compartments, and promoting neuro-inflammatory injury. This subset constitutes only 5-10% of peripheral blood monocytes in healthy seronegative individuals but their percentage increases in HIV infected people. $CD16^+$ monocytes in circulation correlate with HAND, cardiovascular disease, as well as other disorders involving monocyte macrophage activation.

HIV infection can be effectively suppressed by current anti-retroviral therapy regimens, however, the virus remaining is recalcitrant to eradication due to the long-lived nature of latently infected cells, as well as low levels of ongoing virus replication. There are also significant side effects and economic costs of long-term antiviral therapies. Up to now latency reversing strategies have been insufficiently successful and new paradigms are needed to eliminate latent and persistent infection.

TRP catabolism is also important chronic hepatitis C infection in HIV/Hepatitis C co-infection (Jenabian et al., J Acquir Immune Defic Syndr. 2016 Mar. 1; 71(3):254-62), as well as in hepatitis C infection alone (Asghar et al., Exp Ther Med. 2015 March; 9(3):901-904). Typtophan catabolism as determined by IDO activity and kynurenine metabolites correlate liver disease pathogenesis, where liver disease is particularly difficult to treat in HIV/HCV coinfection, despite treatment with cART and ribivarin and pegilated interferon for HIV and HCV respectively. While HCV appears to be more difficult to treat in HIV co-infected patients, TRP catabolism remains elevated in co-infected patients using interferon containing treatment strategies, despite sustained virological response (SRV) to HCV (even after 6 months of SRV), relative to monoinfected patients. Even in HCV and HIV/HCV co-infected patients treated with interferon free regimens, cirrhosis and inadequate SRV remains a significant problem for a large fraction of patients (Nicolini et al., Eur J Gastroenterol Hepatol. 2016 January; 28(1):37-41).

Liver disease is promoted by excess tryptophan catabolism in HCV/HIV patients, despite effective cART treatment and/or HCV treatment. Targeting IDO has been proposed, as a therapeutic in this setting, however, targeting IDO alone may not be sufficient to suppress inflammation.

There is a need in the art for improved methods for modulating pathways associated with tryptophan and NAD+ metabolism for treating diseases, particularly to combine strategies to support NAD+ production, reduce NAD+ hydrolysis, and increase the activity of Sirtuins. The present invention satisfies this unmet need.

BRIEF SUMMARY OF THE INVENTION

In one embodiment, the invention relates to a method of treating a disease in a subject, the method comprising modulating the kynurenine to tryptophan ratio in the subject. In one embodiment, the method comprises administering a composition comprising a NAD+ precursor to the subject. In one embodiment, a NAD+ precursor is administered in combination with an indoleamine 2,3 dioxygenase (IDO) antagonist. In one embodiment, a NAD+ precursor is nicotinamide riboside.

In one embodiment, the disease has an immunosuppressive character.

In one embodiment, the disease is selected from the group consisting of viral infections, bacterial infections, parasitic infections, comorbidities of viral infections, cancers, neurodegenerative diseases or disorders, immune-mediated disorders, inflammatory diseases, cardiovascular diseases, kidney diseases, autoimmune diseases, lupus, systemic lupus erythematosus, age-related disorders, diabetes, obesity, insulin resistance, eating disorders, metabolic syndrome, pain, migraine, rheumatoid arthritis, osteoporosis, sleep disorders, mood disorders, psychiatric diseases or disorders, neurologic diseases or disorders, depression, schizophrenia, Alzheimer disease and Parkinson's Disease.

In one embodiment, a viral infection is HIV infection. In one embodiment, a viral infection is HCV infection.

In one embodiment, the invention relates to a method of treating a disease in a subject, the method comprising modulating NAD+ turnover in the subject. The one embodiment, the method comprises administering a composition comprising a NAD+ precursor to the subject. In one embodiment, a NAD+ precursor is nicotinamide riboside. In one embodiment, a NAD+ precursor is administered in combination with a CD38 antagonist.

In one embodiment, the disease has an immunosuppressive character.

In one embodiment, the disease is selected from the group consisting of viral infections, bacterial infections, parasitic infections, comorbidities of viral infections, cancers, neurodegenerative diseases or disorders, immune-mediated disorders, inflammatory diseases, cardiovascular diseases, kidney diseases, autoimmune diseases, lupus, systemic lupus erythematosus, age-related disorders, diabetes, obesity, insulin resistance, eating disorders, metabolic syndrome, pain, migraine, rheumatoid arthritis, osteoporosis, sleep disorders, mood disorders, psychiatric diseases or disorders, neurologic diseases or disorders, depression, schizophrenia, Alzheimer disease and Parkinson's Disease.

In one embodiment, the invention relates to a method of modulating CD16 expression in a subject, comprising administering to the subject an effective amount of a composition comprising an agent that modulates NAD level. In one embodiment, the method reduces CD16 expression. In one embodiment, the method reduces the frequency of CD16+ monocytes.

In one embodiment, the agent is selected from the group consisting of: a modulator of tryptophan metabolism and a modulator of the NAD salvage pathway. In one embodiment, the agent is nicotinamide riboside or an analog thereof. In one embodiment, nicotinamide riboside is administered in combination with a Sirtuin agonist.

In one embodiment, the invention relates to a method of treating or preventing a disease or disorder associated with CD16 in a subject, comprising administering to the subject an effective amount of a composition comprising an agent that modulates NAD level. In one embodiment, method reduces CD16 expression. In one embodiment, the method reduces the frequency of CD16+ monocytes.

In one embodiment, the agent is selected from the group consisting of: a modulator of tryptophan metabolism and a modulator of the NAD salvage pathway. In one embodiment, the agent is nicotinamide riboside or an analog thereof.

In one embodiment, the disease or disorder is selected from the group consisting of: HIV infection, SIV infection, HIV-associated neurocognitive disorders (HAND), HIV-associated viral infections, cardiovascular disease, kidney disease, obesity, autoimmune diseases, Crohn's disease, rheumatoid arthritis, cancer, atherosclerosis, and central nervous system diseases (with or without infection).

In one embodiment, the invention relates to a method of treating HIV infection or an HIV-associated disorder in a subject, comprising administering to the subject an effective amount of a composition comprising an agent that modulates NAD level. In one embodiment, the method reduces CD16 expression. In one embodiment, the method reduces the frequency of CD16+ monocytes.

In one embodiment, the agent is selected from the group consisting of: a modulator of tryptophan metabolism and a modulator of the NAD salvage pathway. In one embodiment, the agent is nicotinamide riboside or an analog thereof.

In one embodiment, the invention relates to a method of treating HCV infection or an HCV-associated disorder in a subject, comprising administering to the subject an effective amount of a composition comprising an agent that modulates NAD level. In one embodiment, an agent that modulates NAD level is a NAD+ precursor. In one embodiment, the NAD+ precursor is nicotinamide riboside.

In one embodiment, the method comprises administering to the subject an effective amount of a composition comprising an agent that modulates NAD level in combination with one or more additional agents selected from the group consisting of an indoleamine 2,3 dioxygenase (IDO) antagonist, a CD38 antagonist and a sirtuin agonist.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2, comprising FIG. 2A is from Hassa et al., Microbiol Mol Biol Rev. 2006 September; 70(3):789-829 and depicts NAD+ production from tryptophan (via the kynurenine pathway) and salvage pathways and catabolism, ADPR cyclases (i.e. primarily by CD38). The role of IDO as the initial step in tryptophan breakdown is shown. Shown in the salvage pathway is nicotinamide riboside (NR, dashed-line box), an intermediate demonstrated in recent years to be an important precursor for NAD+ synthesis, and the subject our therapeutic strategy (Bieganowski et al., Cell. 2004; 117(4):495-502). FIG. 2B depicts a schematic diagram showing that, in HIV infection, NAD+ destruction by CD38 is central to immune suppression, chronic inflammation and latency, as well as a mechanism that draws on increased IDO mediated tryptophan catabolism, increasing NAD+ turnover in the presence of CD38 activation, KYN metabolites, and HIV latency involving acetylated Tat mediated by defective SIRT-1 activity. This figure illustrates the increased catabolism of tryptophan, initiating with the IDO enzyme step, leading to the production of kynurenine metabolites contributing to immune suppression and CNS injury in the context of HIV infection. The catabolism of tryptophan results in immune suppression, T cell apoptosis, and anergy. Metabolism of tryptophan as well as salvage pathway NAD+ precursors needed to replace NAD+ consumed primarily by CD38, an NAD+ glycohydrolase. As NAD+ levels are reduced, particularly in the context of metabolic activation, SIRT-1 activity is inhibited as NAD+ is rate limiting. SIRT-1 is required to control inflammation through the acetylation of p65NFkB. As a result of NAD+ depletion and SIRT-1 inactivation, inflammation and accelerated aging promote comorbidities observed with HIV infection. Further, the loss of regulation of NFkB results in increased IDO expression via TNFα activation. Since HIV-1 Tat inhibits SIRT-1 activity and also is a substrate of SIRT-1 deacetylation, acetylated Tat protein is prevented from recycling at the HIV LTR promoter and does not initiate new rounds of transcription, contributing to the maintenance of latency. The loss of tryptophan in this model by catabolism contributes to immune suppression as well as inadequate levels for melatonin and serotonin production, with the latter providing a mechanism for sleep disorders and depression commonly occurring in HIV infection.

FIG. 4, comprising FIG. 4A depicts the plasma tryptophan concentration for uninfected and SIV infected macaques. FIG. 4B depicts the plasma kynurenine concentration for uninfected and SIV infected macaques. FIG. 4C depicts the kynurenine to tryptophan ratio. Data was analyzed across 3 time points, for 5 seronegative and 10 SIV infected animals. The results indicate a decrease in Tryptophan concentration and an increase in Kynurenine concentration in SIV positive animals when compared to uninfected controls resulting in an increase in kynurenine to tryptophan ratio. Paired T test was performed $P \leq 0.01$; *$P \leq 0.001$; n=53.

FIG. 5, comprising FIG. 5A depicts a correlation plot demonstrating that kynurenine to tryptophan ratios increased in relations to higher viral loads (r=0.4774; p=0.0028). FIG. 5B depicts a correlation plot demonstrating a positive correlation between kynurenine to tryptophan ratio and sCD163 plasma concentration is observed (r=0.473; p=0.0027). FIG. 5C depicts a correlation plot demonstrating kynurenine to tryptophan ratios also exhibited a positive correlation with plasma ATP levels (r=0.3514; p=0.0305). Pearson correlation was performed n=53.

FIG. 6, comprising FIG. 6A depicts results showing the KTR before SIV infection, 14 days following infection and 30 days following infection. FIG. 6B depicts results showing the NAD concentration before SIV infection, 14 days following infection and 30 days following infection. FIG. 6C depicts results showing the KTR 14 days following infection and 1 year following infection. FIG. 6D depicts results showing the NAD concentration 14 days following infection and 1 year following infection.

FIG. 7, comprising FIG. 7A depicts NAD+ concentrations before NR treatment demonstrate significantly lower NAD+ concentrations in SIV infected macaques. FIG. 7B depicts that there was not a significant change in NAD+ concentration in uninfected animals (P=0.0883). FIG. 7C depicts experimental results demonstrating that treatment with NR significantly increased NAD+ concentration in SIV infected rhesus macaques. Paired T test and one way ANOVA was performed *P≤0.05; **P≤0.01 n=9.

FIG. 8, comprising FIG. 8A depicts the KTR in SIV infected animals treated with different concentrations of NR. FIG. 8B depicts the KTR in uninfected animals treated with different concentrations of NR.

FIG. 9, comprising FIG. 9A depicts flow cytometry results demonstrating that prior to treatment with NR monocyte populations demonstrate normal CD16 expression. FIG. 9B depicts flow cytometry results demonstrating that after treatment with NR CD16 expression decreased in all animals examined.

FIG. 10, comprising FIG. 10A depicts results showing that CD16 MFI before NR treatment was significantly higher than after treatment in all animals. FIG. 10B depicts that the percent frequency of CD16 was significantly decreased after treatment with NR in uninfected and SIV infected macaques. One-way ANOVA was performed *P≤0.05; P≤0.01; *P≤0.001; n=9.

FIG. 22, comprising FIG. 22A depicts representative images of atherosclerotic lesions formed in the aortic root. FIG. 22B depicts a quantification of the percentage of the aortic root that had lesions.

FIG. 24, comprising FIG. 24A depicts serum cholesterol levels. FIG. 24B depicts serum triglyceride levels.

FIG. 25, comprising FIG. 25A depicts kynurenine concentration. FIG. 24B depicts tryptophan concentration.

FIG. 28, comprising FIG. 28A depicts representative images showing an increase in the number of foam cells present in Tg26$^{+/-}$ Apoe$^{-/-}$ mice as compared to Tg26$^{-/-}$ Apoe$^{-/-}$ mice. FIG. 28B depicts a quantification of foam cell formation.

DETAILED DESCRIPTION

Figure 1:
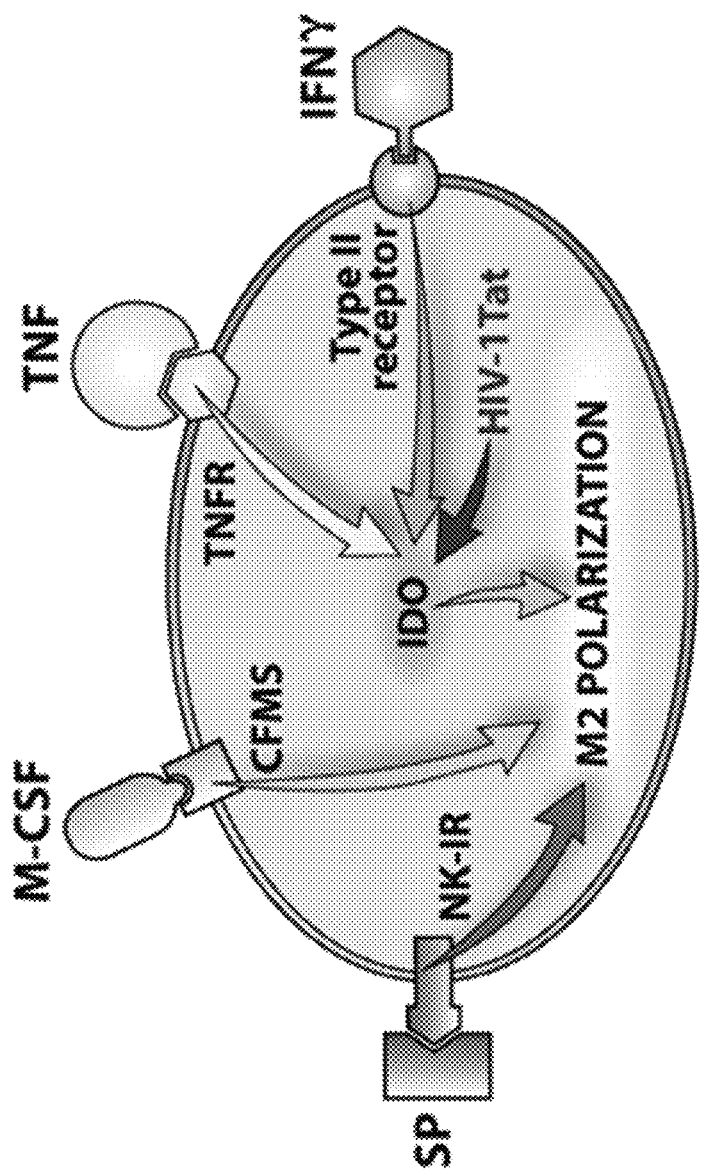
FIG. 1 depicts a schematic illustration depicting pathways affecting macrophage M2 polarization, including a role for IDO.

NAD+ is an important metabolite in virtually every biologic process. Without wishing to be bound by any particular theory, it is believed that immune suppression, in HIV infection is driven by the turnover of NAD+. It is believed that NAD+ turnover is driven by two things, the hydrolysis of NAD+ by the ecto-enzyme CD38, as well as the increased production of NAD via the catabolism of tryptophan as well as salvage pathways involving niacin and nicotinamide riboside. The demand and degradation of tryptophan results in immune suppression, immune suppressive metabolites derived from the kynurenine pathway. Immunosuppression and CNS disease arise from these processes. The catabolism of tryptophan reduces the amount of tryptophan shunted to the production of serotonin and melatonin. Hence this process promotes sleep disorders and depression. Since NAD+ is required for the action of the sirtuin deacetylases, NAD+ catabolism results in reduced SIRT activity. SIRT-I controls inflammation and controls the effects of aging through NAD+ which is limiting. Reduced SIRT-1 activity also promotes latency by stalling HIV-1 protein within the HIV-I promoter in association with cyclinT/CDK9. As deacetylation is required to recycle new rounds of Tat mediated transcription, the reduction of NAD induces a latent state in otherwise active chromatin. This invention details an approach to modulate pathways involved in tryptophan and NAD+ metabolism. In one embodiment, modulation of pathways involved in tryptophan and NAD+ metabolism is associated with one or more of increased SIRT-I activity, increased serotonin levels, reduced CD16 expression, reduced kynurenine metabolites, reduced inflammation and increased immunity.

In one embodiment, the present invention relates to a method of modulating tryptophan and NAD+ metabolism to reverse HIV latency, and effectively treat HIV infection or an HIV associated comorbidity. The strategy described could also be used to treat diseases in persons not infected with HIV.

In one embodiment, the present invention relates to preventing NAD degradation and at the same time providing an alternate source of NAD precursors (other than tryptophan). There is a major benefit in reducing accelerated aging, immunosuppression, comorbidities (cardiovascular, pulmonary, nervous system, etc.). Furthermore, the treatment method of the invention restores SIRT activity, reverses latency, and reduces chronic inflammation. In the context of antiretroviral treatment, this approach would restore immunity such that antiretroviral treatment could be interrupted, as long as the treatment to maintain NAD levels via precursors and blocking degradation remain intact. Without wishing to be bound by any particular theory, it is believed that this enables the immune system to function appropriately and clear latent reservoirs.

In one embodiment, the invention provides the combined use of nicotinamide riboside as a NAD+ precursor is provided in combination with a CD38 antagonist, which represent the major source of NAD+ degradation. CD38 expression remains elevated in the context of antiretroviral treatment and expression on CD8 T cells appears to be a biomarker for continued virus replication. CD38+ CD4+Th cells which harbor virus are also cleared more slowly than CD38-Th cells. The results presented herein demonstrates the importance of Sirtuins. Without wishing to be bound by any particular theory, it is believed that Nicotinamide Riboside would be more effective than nicotinamide, as an NAD+ precursor. This treatment could also benefit from Sirtuin agonists such as resveratrol or SRT-21 011.

In one embodiment, the invention provides a curative therapy of HIV as an adjunctive to cART and treatment interruption.

In one embodiment, the invention provides treatment of comorbidities of HIV due to accelerated aging including renal, cardiovascular, CNS, pulmonary, associated cancers, neurocognitive impairment, depression, Alzheimer disease and Parkinson's Disease.

In one embodiment, the invention provides a treatment of diseases in the absence of HIV therapy. In one embodiment, the invention provides treatment of viral infections, bacterial infections, parasitic infections, comorbidities of viral infections, cancers, neurodegenerative diseases or disorders, immune-mediated disorders, inflammatory diseases, cardiovascular diseases, kidney diseases, autoimmune diseases, lupus, systemic lupus erythematosus, age-related disorders, diabetes, obesity, insulin resistance, eating disorders, metabolic syndrome, pain, migraine, rheumatoid arthritis, osteoporosis, sleep disorders, mood disorders, psychiatric diseases or disorders, neurologic diseases or disorders, depression, schizophrenia, Alzheimer disease and Parkinson's Disease.

The invention is partly based on the discovery that NAD+ turnover is at the center of the HIV problem and key to a cure. Accordingly, the invention encompasses modulating other NAD+ consuming enzymes like SIRT-1, PPAR-gamma, CD38, and the like. In some instances, the invention is able to correct PPARgamma regulation on NAD catabolism.

In one embodiment, the invention provides a method for treating HIV and HIV-associated disorders. For example, in one embodiment, the method comprises administering an effective amount of an agent that modulates NAD level to a subject having HIV or an HIV-associated disorder. In one embodiment, the agent that modulates NAD level is a modulator of TRP metabolism or the NAD salvage pathway. In one embodiment, the agent is nicotinamide riboside, or an analog thereof.

In one embodiment, the method comprises treating or preventing any disease or disorder associated with CD16. In one embodiment, the method comprises administering an effective amount of an agent that modulates NAD level to a subject having a disease or disorder associated with CD16, or to a subject at risk for developing a disease or disorder associated with CD16. In one embodiment, the agent that modulates NAD level is a modulator of TRP metabolism or the NAD salvage pathway. In one embodiment, the agent is nicotinamide riboside, or an analog thereof. In one embodiment, the method decreases CD16 expression, thereby treating or preventing the disease. In one embodiment, the method decreases the frequency of CD16+ monocytes, thereby treating or preventing the disease.

In certain embodiments, the invention provides compositions and methods related to the combination of an agents that increases NAD+ concentration and one or more additional agents that modulate an activity of a gene or gene product affected by NAD+ concentration (e.g. CD16 expression and Sirtuin activation), tryptophan metabolism, or kynurenine to tryptophan ratio.

In certain embodiments, the invention provides compositions and methods related to the combination of increasing NAD+ and decreasing degradation of NAD+ through inhibition of CD38. In one embodiment, the invention provides a combination of a NAD precursor and an inhibitor of CD38. In one embodiment, a NAD precursor is one of nicotinamide riboside, nicotinamide mononucleotide and nicotinamide and a CD38 inhibitor is one of a monoclonal antibody inhibitor of CD38, Isatuximab (SAR650984, Sanofi), and 4-amino-8-quinoline carboxamides (e.g. 1ah and 1ai).

In certain embodiments, the invention provides compositions and methods related to the combination of increasing NAD+ and activating a Sirtuin. In one embodiment, a Sirtuin is Sirtuin-1. In one embodiment, the invention provides a combination of a NAD precursor and a Sirtuin agonist. In one embodiment, a NAD precursor is one of nicotinamide riboside, nicotinamide mononucleotide and nicotinamide and a Sirtuin agonist is one of Resveratrol, Resveratrol modified compounds with improved bioavailability, resVida, Lonevinex, SRT501, Pterostilbene, agonists of sirtuins unrelated to resveratrol including but not limited to SRT1720, SRT2104, SRT2379, berberine, acetylsalicylic acid, Metformin, AICAR, AZD-769662 oxaloacetate, and inhibitors of mTOR, including but not limited to rapamycin.

In certain embodiments, the invention provides compositions and methods related to the combination of increasing NAD+ and decreasing tryptophan catabolism. In one embodiment, the invention provides a combination of a NAD precursor and an IDO antagonist. In one embodiment, a NAD precursor is one of nicotinamide riboside, nicotinamide mononucleotide and nicotinamide and an IDO antagonist is 1-methyl tryptophan.

Exemplary diseases or disorders treated or prevented by way of the compositions or combinations of the invention include, but are not limited to, HIV infection, SIV infection, HIV-associated neurocognitive disorders (HAND), HIV-associated viral infections, cardiovascular disease, kidney disease, obesity, autoimmune diseases, Crohn's disease, rheumatoid arthritis, cancer, atherosclerosis, and central nervous system diseases (with or without infection).

Liver disease is promoted by excess tryptophan catabolism in HCV/HIV patients, despite effective cART treatment and/or HCV treatment. In various embodiments, the methods of the invention are used to reduce inflammation in HIV, HCV, and HIV-HCV, effectively preventing and treating HIV, HCV, and HIV/HCV morbidities and comorbidities, as well as to provide curative strategies through enhancement of immune function. Therefore, in one embodiment, the invention relates to methods of targeting IDO in combination with one or more of providing NAD+ salvage pathway precursors, CD38+ antagonists, and/or sirtuin agonists to reduce inflammation in HIV, HCV, and HIV-HCV, effectively preventing and treating HIV, HCV, and HIV/HCV morbidities and comorbidities.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Generally, the nomenclature used herein and the laboratory procedures in cell culture, molecular genetics, organic chemistry, and nucleic acid chemistry and hybridization are those well-known and commonly employed in the art.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The term "activate," as used herein, means to induce or increase an activity or function, for example, about ten percent relative to a control value. Preferably, the activity is induced or increased by 50% compared to a control value, more preferably by 75%, and even more preferably by 95%. "Activate," as used herein, also means to increase a molecule, a reaction, an interaction, a gene, an mRNA, and/or a protein's expression, stability, function or activity by a measurable amount or to increase entirely. Activators are compounds that, e.g., bind to, partially or totally induce stimulation, increase, promote, induce activation, activate, sensitize, or up regulate a protein, a gene, and an mRNA stability, expression, function and activity, e.g., agonists.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The an antibody in the present invention may exist in a variety of forms where the antigen binding portion of the antibody is expressed as part of a contiguous polypeptide chain including, for example, a single domain antibody fragment (sdAb), a single chain antibody (scFv) and a humanized antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "cancer" as used herein is defined as disease characterized by the abnormal growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer, sarcoma and the like.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity or frequency of at least one sign or symptom of the disease or disorder experienced by a patient is reduced.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

The term "inhibit," as used herein, means to suppress or block an activity or function, for example, about ten percent relative to a control value. Preferably, the activity is suppressed or blocked by 50% compared to a control value, more preferably by 75%, and even more preferably by 95%. "Inhibit," as used herein, also means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is a naturally-occurring sequence.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

The term "protein" typically refers to large polypeptides.
The term "peptide" typically refers to short polypeptides.

As used herein, a "peptidomimetic" is a compound containing non-peptidic structural elements that is capable of mimicking the biological action of a parent peptide. A peptidomimetic may or may not comprise peptide bonds.

"Sample" or "biological sample" as used herein means a biological material from a subject, including but is not limited to organ, tissue, exosome, blood, plasma, saliva, urine and other body fluid. A sample can be any source of material obtained from a subject.

The terms "treat," "treating," and "treatment," refer to therapeutic or preventative measures described herein. The methods of "treatment" employ administration to a subject, in need of such treatment, a composition of the present invention, for example, a subject afflicted a disease or disorder, or a subject who ultimately may acquire such a disease or disorder, in order to prevent, cure, delay, reduce the severity of, or ameliorate one or more symptoms of the disorder or recurring disorder, or in order to prolong the survival of a subject beyond that expected in the absence of such treatment.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The invention is based, in part, on the discoveries that elevated kynurenine to tryptophan ratio associated with HIV infection and HIV-associated comorbidities and furthermore, the inventors hypothesis that CD38 mediated NAD+ hydrolysis reduces intracellular cellular NAD+, activates de novo and salvage pathway synthesis of NAD+ via the IDO pathway as well as NAD+ salvage pathways, respectively. CD38 activity, de novo and salvage NAD synthesis pathways can be modulated alone or together to ameliorate disease. Therefore the present invention relates generally to compositions for modulating CD38 and the kynurenine to tryptophan ratio and the use of such compositions in methods of treating disease. In one embodiment a modulator of the kynurenine to tryptophan ratio affects one or more of tryptophan metabolism, a kynurenine pathway, biosynthesis of serotonin, or biosynthesis of melatonin in a subject.

Modulators

The invention relates to modulators that effect various metabolic processes in a subject, such as for example modulating tryptophan metabolism, modulating kynurenine to tryptophan ratio, and regulating the kynurenine pathway in a subject. In one embodiment, a modulator of the invention increases biosynthesis, and/or the levels, of $NAD^+$ in a subject. In one embodiment, a modulator of the invention increases biosynthesis, and/or the levels, of chemical entities in a subject, for example serotonin and/or melatonin. In one embodiment, a modulator of the invention decreases biosynthesis, and/or the levels, of chemical entities in a subject, for example kynurenine metabolites such as quinolinic acid.

Compositions

In one embodiment, the compositions of the invention modulate the amount or level of tryptophan metabolism. In one embodiment, the compositions of the invention modulate tryptophan metabolism through modulation of the kynurenine pathway, modulation of the methoxyindole pathway or the modulation of the NAD salvage pathway.

In one embodiment, the composition of the invention modulates (inhibits) CD38 activity, thereby decreasing NAD+ turnover and reducing the need for tryptophan catabolism. In one embodiment, CD38 antagonists can be applied together with IDO antagonists, salvage pathway precursors, or combinations of all three elements.

In one embodiment, the compositions of the invention increase the activity of the methoxyindole pathway. In one embodiment, compositions of the invention increase the level or amount of a metabolite of the methoxyindole pathway (e.g. serotonin and/or melatonin.)

In one embodiment, the invention provides a modulator of the kynurenine pathway. In various embodiments, the present invention includes compositions for modulating the level or activity of the kynurenine pathway in a subject, a cell, a tissue, or an organ in need thereof. In various embodiments, the compositions of the invention modulates the amount of polypeptide, the amount of mRNA, or activity of a protein in the kynurenine pathway, or a combination thereof. In one embodiment, a protein in the kynurenine pathway may be indoleamine dioxygenase. In one embodiment, the compositions of the invention decrease the level or activity of indoleamine dioxygenase.

In one embodiment, the compositions of the invention modulate the amount or level of a product of the kynurenine pathway. In one embodiment, a product of the kynurenine pathway is NAD+. In one embodiment, the compositions of the invention increase the level or concentration of NAD+.

In one embodiment, the invention relates to increasing NAD levels via modulation of TRP metabolism and/or modulation of the NAD salvage pathway in order to modulate CD16 expression. Therefore, in one embodiment, the compositions of the invention modulate CD16 expression. In one embodiment, a composition useful for modulating CD16 expression is nicotinamide riboside, or analog thereof. For example, in certain aspects the invention relates to the use of nicotinamide riboside to increase NAD level and/or decrease CD16 expression.

Modulators of the kynurenine to tryptophan ratio include, but are not limited to, NAD and NAD precursors (e.g. nicotinamide mononucleotide, nicotinamide, nicotinic acid (Niacin) and nicotinamide riboside (Niagen®)); IDO antagonists (e.g. 1-methyl tryptophan); CD38 antagonists (e.g. Isatuximab and other monoclonal antibodies, 4-amino-8-quinoline carboxamides such as 1ah and 1ai (Becherer et al., J Med Chem. 2015, 58:7021-7056)); Sirtuin activators (e.g. Resveratrol, Resveratrol modified compounds with improved bioavailability such as resVida, Lonevinex, SRT501 and Pterostilbene, SRT1720, SRT2104, SRT2379, and Berberine), AMPK (AMP-activated protein kinase) activators (e.g. Metformin, AICAR (AMP analog), AZD-769662 and acetylsalicylic acid); Oxaloacetate (Williams et al., Aging Cell, 2009, 8:765-768); Inhibitors of mammalian Target of Rapamycin (mTOR) pathway (e.g. rapamycin); and immune checkpoint blockers (e.g. drugs/monoclonal antibodies targeting CTLA-4, LAG-3, TIGIT, and PD-1 and/or their ligands), or combinations thereof.

Activators

In one embodiment, the present invention relates to the prevention and treatment of a disease or disorder by administration of a NAD precursor alone or in combination with a Sirtuin activator or agonist. Therefore, in various embodiments, the composition for treating a disease comprises an activator of Sirtuin. In one embodiment, the activator of the invention increases the amount of Sirtuin polypeptide, the amount of Sirtuin mRNA, the amount of Sirtuin activity, or a combination thereof. In one embodiment, a Sirtuin is Sirtuin-1.

It will be understood by one skilled in the art, based upon the disclosure provided herein, that an increase in the level of Sirtuin encompasses the increase in Sirtuin expression, including transcription, translation, or both. The skilled artisan will also appreciate, once armed with the teachings of the present invention, that an increase in the level of Sirtuin includes an increase in Sirtuin activity. Thus, increasing the level or activity of Sirtuin includes, but is not limited to, increasing the amount of Sirtuin polypeptide, increasing transcription, translation, or both, of a nucleic acid encoding Sirtuin; and it also includes increasing any activity of a Sirtuin polypeptide as well.

Thus, the present invention relates to the prevention and treatment of a disease or disorder by administration of a NAD precursor alone or in combination with a a Sirtuin polypeptide, a recombinant Sirtuin polypeptide, an active Sirtuin polypeptide fragment, an organic compound, an inorganic compound, a small molecule or an activator of Sirtuin expression or activity.

It is understood by one skilled in the art, that an increase in the level of Sirtuin encompasses the increase of Sirtuin protein expression. Additionally, the skilled artisan would appreciate, that an increase in the level of Sirtuin includes an increase in Sirtuin activity. Thus, increasing the level or activity of Sirtuin includes, but is not limited to, increasing transcription, translation, or both, of a nucleic acid encoding a Sirtuin; and it also includes increasing any activity of a Sirtuin as well.

Activation of a Sirtuin can be assessed using a wide variety of methods, including those disclosed herein, as well as methods well-known in the art or to be developed in the future. That is, increasing the level or activity of a Sirtuin can be readily assessed using methods that assess the level of a nucleic acid encoding a Sirtuin (e.g., mRNA) and/or the level of a Sirtuin polypeptide in a biological sample obtained from a subject.

A Sirtuin activator can include, but should not be construed as being limited to, a chemical compound, a protein, a peptidomemetic, an antibody, a nucleic acid molecule. One of skill in the art would readily appreciate, based on the disclosure provided herein, that a Sirtuin activator encompasses a chemical compound that increases the level, enzymatic activity, or the like of a Sirtuin. In some embodiments, the enzymatic activity is protein deacetylation. Additionally, a Sirtuin activator encompasses a chemically modified compound, and derivatives, as is well known to one of skill in the chemical arts.

It will be understood by one skilled in the art, based upon the disclosure provided herein, that an increase in the level of a Sirtuin encompasses the increase in Sirtuin expression, including transcription, translation, or both. The skilled artisan will also appreciate, once armed with the teachings of the present invention, that an increase in the level of a Sirtuin includes an increase in Sirtuin activity (e.g., enzymatic activity, receptor binding activity, etc.). Thus, increasing the level or activity of a Sirtuin includes, but is not limited to, increasing the amount of a Sirtuin polypeptide, increasing transcription, translation, or both, of a nucleic acid encoding a Sirtuin; and it also includes increasing any activity of a Sirtuin polypeptide as well. The Sirtuin activator compositions and methods of the invention can selectively activate a Sirtuin. Thus, the present invention relates to administration of a Sirtuin polypeptide, a recombinant Sirtuin polypeptide, an active Sirtuin polypeptide fragment, an organic compound, an inorganic compound, a small molecule or a Sirtuin activator.

Further, one of skill in the art would, when equipped with this disclosure and the methods exemplified herein, appreciate that a Sirtuin activator includes such activators as discovered in the future, as can be identified by well-known criteria in the art of pharmacology, such as the physiological results of activation of a Sirtuin as described in detail herein and/or as known in the art. Therefore, the present invention is not limited in any way to any particular Sirtuin activator as exemplified or disclosed herein; rather, the invention encompasses those activators that would be understood to be useful as are known in the art and as are discovered in the future.

Further methods of identifying and producing a Sirtuin activator are well known to those of ordinary skill in the art, including, but not limited, obtaining an activator from a naturally occurring source. Alternatively, a Sirtuin activator can be synthesized chemically. Further, the routineer would appreciate, based upon the teachings provided herein, that a Sirtuin activator can be obtained from a recombinant organism. Compositions and methods for chemically synthesizing Sirtuin activators and for obtaining them from natural sources are well known in the art and are described in the art.

One of skill in the art will appreciate that an activator can be administered as a small molecule chemical, a protein, a nucleic acid construct encoding a protein, or combinations thereof. Numerous vectors and other compositions and methods are well known for administering a protein or a nucleic acid construct encoding a protein to cells or tissues. Therefore, the invention includes a method of administering a protein or a nucleic acid encoding a protein that is an activator of a Sirtuin.

One of skill in the art will realize that diminishing the amount or activity of a molecule that itself diminishes the amount or activity of a Sirtuin can serve to increase the amount or activity of a Sirtuin. Any inhibitor of a regulator of a Sirtuin is encompassed in the invention. As a non-limiting example, antisense is described as a form of inhibiting a regulator of a Sirtuin in order to increase the amount or activity of a Sirtuin. Antisense oligonucleotides are DNA or RNA molecules that are complementary to some portion of a mRNA molecule. When present in a cell, antisense oligonucleotides hybridize to an existing mRNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931). The methods of the invention include the use of antisense oligonucleotide to diminish the amount of a molecule that causes a decrease in the amount or activity of a Sirtuin, thereby increasing the amount or activity of a Sirtuin. Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing a protein that diminishes the level or activity of a Sirtuin can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

One of skill in the art will appreciate that a Sirtuin polypeptide, a recombinant Sirtuin polypeptide, an active Sirtuin polypeptide fragment, an organic compound, an inorganic compound or a small molecule can be administered singly or in any combination thereof. Further, a Sirtuin polypeptide, a recombinant Sirtuin polypeptide, an active Sirtuin polypeptide fragment, an organic compound, an inorganic compound or a small molecule can be administered singly or in any combination thereof in a temporal sense, in that they may be administered simultaneously, before, and/or after each other. One of ordinary skill in the art will appreciate, based on the disclosure provided herein, that a Sirtuin polypeptide, a recombinant Sirtuin polypeptide, an active Sirtuin polypeptide fragment, an organic compound, an inorganic compound, a small molecule or an activator of a Sirtuin can be used to prevent or treat a disease or disorder, and that an activator can be used alone or in any combination with a NAD precursor to effect a therapeutic result.

One of skill in the art, when armed with the disclosure herein, would appreciate that the treating a disease or disorder encompasses administering to a subject a Sirtuin polypeptide, a recombinant Sirtuin polypeptide, an active Sirtuin polypeptide fragment, an organic compound, an inorganic compound, a small molecule or Sirtuin activator as a preventative measure against the disease or disorder. As more fully discussed elsewhere herein, methods of increasing the level or activity of a Sirtuin encompass a wide plethora of techniques for increasing not only Sirtuin activity, but also for increasing expression of a nucleic acid encoding Sirtuin. Additionally, as disclosed elsewhere herein, one skilled in the art would understand, once armed with the teaching provided herein, that the present invention encompasses a method of preventing a wide variety of diseases where increased expression and/or activity of a Sirtuin mediates, treats or prevents the disease. Further, the invention encompasses treatment or prevention of such diseases discovered in the future.

The invention encompasses administration of a Sirtuin polypeptide, a recombinant Sirtuin polypeptide, an active Sirtuin polypeptide fragment, an organic compound, an inorganic compound, a small molecule or Sirtuin activator to practice the methods of the invention; the skilled artisan would understand, based on the disclosure provided herein, how to formulate and administer the appropriate a Sirtuin polypeptide, a recombinant Sirtuin polypeptide, an active Sirtuin polypeptide fragment, an organic compound, an inorganic compound, a small molecule or Sirtuin activator to a subject. However, the present invention is not limited to any particular method of administration or treatment regimen. This is especially true where it would be appreciated by one skilled in the art, equipped with the disclosure provided herein, including the reduction to practice using an art-recognized model of a disease, that methods of administering a Sirtuin polypeptide, a recombinant Sirtuin polypeptide, an active Sirtuin polypeptide fragment, an organic compound, an inorganic compound, a small molecule or Sirtuin activator can be determined by one of skill in the pharmacological arts.

As used herein, the term "pharmaceutically-acceptable carrier" means a chemical composition with which an appropriate Sirtuin polypeptide, a recombinant Sirtuin polypeptide, an active Sirtuin polypeptide fragment, an organic compound, an inorganic compound, a small molecule or Sirtuin activator, may be combined and which, following the combination, can be used to administer the appropriate Sirtuin polypeptide, a recombinant Sirtuin polypeptide, an active Sirtuin polypeptide fragment, an organic compound, an inorganic compound, a small molecule or a Sirtuin activator to a subject.

Inhibitors

In one embodiment, the present invention relates to the prevention and treatment of a disease or disorder by administration of a NAD precursor alone or in combination with an inhibitor of NAD degradation. In one embodiment, an inhibitor of NAD degradation is an inhibitor of CD38.

In one embodiment, the present invention relates to the prevention and treatment of a disease or disorder by administration of a NAD precursor in combination with an inhibitor of tryptophan catabolism. In one embodiment, an inhibitor of tryptophan catabolism is an inhibitor of IDO.

In various embodiments, the composition for treating disease comprises an inhibitor of NAD degradation and/or tryptophan catabolism. In one embodiment, the inhibitor of the invention decreases the amount of polypeptide, the amount of mRNA, the amount of activity, or a combination thereof of a protein required for NAD degradation and/or tryptophan catabolism.

It will be understood by one skilled in the art, based upon the disclosure provided herein, that a decrease in the level of a protein required for NAD degradation and/or tryptophan catabolism encompasses the decrease in the expression, including transcription, translation, or both. The skilled artisan will also appreciate, once armed with the teachings of the present invention, that a decrease in the level of a protein required for NAD degradation and/or tryptophan catabolism includes a decrease in the activity of the protein required for NAD degradation and/or tryptophan catabolism. Thus, a decrease in the level or activity of CD38 includes, but is not limited to, decreasing the amount of polypeptide of CD38, and decreasing transcription, translation, or both, of a nucleic acid encoding CD38; and it also includes decreasing any activity of CD38 as well. Similarly, a decrease in the level or activity of IDO includes, but is not limited to, decreasing the amount of polypeptide of IDO, and decreasing transcription, translation, or both, of a nucleic acid encoding IDO; and it also includes decreasing any activity of IDO as well.

In one embodiment, the invention provides a generic concept for increasing NAD as a therapeutic treatment for disease. CD38 promotes NAD degradation, therefore, in one embodiment, the composition of the invention comprises an inhibitor of CD38. In one embodiment, the inhibitor is selected from the group consisting of a small interfering RNA (siRNA), a microRNA, an antisense nucleic acid, a ribozyme, an expression vector encoding a transdominant negative mutant, an antibody, a peptide and a small molecule.

In one embodiment, the invention provides a concept for increasing NAD concentration in combination with inhibiting tryptophan catabolism as a therapeutic treatment for disease. IDO promotes tryptophan catabolism by the kynurenine pathway, therefore, in one embodiment, the composition of the invention comprises an inhibitor of IDO.

One skilled in the art will appreciate, based on the disclosure provided herein, that one way to decrease the mRNA and/or protein levels of a protein required for NAD degradation and/or tryptophan catabolism in a cell is by reducing or inhibiting expression of the nucleic acid encoding a protein required for NAD degradation and/or tryptophan catabolism. Thus, the protein level of a protein required for NAD degradation and/or tryptophan catabolism in a cell can also be decreased using a molecule or compound that inhibits or reduces gene expression such as, for example, siRNA, an antisense molecule or a ribozyme. However, the invention should not be limited to these examples.

In one embodiment, siRNA is used to decrease the level of a protein required for NAD degradation and/or tryptophan catabolism. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19): 306-311; Timmons et al., 1998, Nature 395:854; Montgomery et al., 1998, TIG 14 (7):255-258; David R. Engelke, Ed., RNA Interference (RNAi) Nuts & Bolts of RNAi Technology, DNA Press, Eagleville, P A (2003); and Gregory J. Hannon, Ed., RNAi A Guide to Gene Silencing, Cold Spring Harbor Laboratory Press, Cold Spring Harbor, N.Y. (2003). Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of a protein required for NAD degradation and/or tryptophan catabolism at the protein level using RNAi technology.

In other related aspects, the invention includes an isolated nucleic acid encoding an inhibitor, wherein an inhibitor such as an siRNA or antisense molecule, inhibits a protein required for NAD degradation and/or tryptophan catabolism, a derivative thereof, a regulator thereof, or a downstream effector, operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York) and as described elsewhere herein. In another aspect of the invention, a protein required for NAD degradation and/or tryptophan catabolism or a regulator thereof, can be inhibited by way of inactivating and/or sequestering one or more of a protein required for NAD degradation and/or tryptophan catabolism, or a regulator thereof. As such, inhibiting the effects of a protein required for NAD degradation and/or tryptophan catabolism can be accomplished by using a transdominant negative mutant.

In another aspect, the invention includes a vector comprising an siRNA or antisense polynucleotide. Preferably, the siRNA or antisense polynucleotide is capable of inhibiting the expression of a protein required for NAD degradation and/or tryptophan catabolism. The incorporation of a desired polynucleotide into a vector and the choice of vectors is well-known in the art as described in, for example, Sambrook et al., supra.

The siRNA or antisense polynucleotide can be cloned into a number of types of vectors as described elsewhere herein. For expression of the siRNA or antisense polynucleotide, at least one module in each promoter functions to position the start site for RNA synthesis.

In order to assess the expression of the siRNA or antisense polynucleotide, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

In one embodiment of the invention, an antisense nucleic acid sequence which is expressed by a plasmid vector is used to inhibit a protein required for NAD degradation and/or tryptophan catabolism. The antisense expressing vector is used to transfect a mammalian cell or the mammal itself, thereby causing reduced endogenous expression of a protein required for NAD degradation and/or tryptophan catabolism.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

Compositions and methods for the synthesis and expression of antisense nucleic acids are as described elsewhere herein.

Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is the fact that ribozymes are sequence-specific.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

In one embodiment of the invention, a ribozyme is used to inhibit a protein required for NAD degradation and/or tryptophan catabolism. Ribozymes useful for inhibiting the expression of a target molecule may be designed by incorporating target sequences into the basic ribozyme structure which are complementary, for example, to the mRNA sequence of a protein required for NAD degradation and/or tryptophan catabolism of the present invention. Ribozymes targeting a protein required for NAD degradation and/or tryptophan catabolism may be synthesized using commercially available reagents (Applied Biosystems, Inc., Foster City, Calif.) or they may be genetically expressed from DNA encoding them.

When the inhibitor of the invention is a small molecule, a small molecule antagonist may be obtained using standard methods known to the skilled artisan. Such methods include chemical organic synthesis or biological means. Biological means include purification from a biological source, recombinant synthesis and in vitro translation systems, using methods well known in the art.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

In another aspect of the invention, a protein required for NAD degradation and/or tryptophan catabolism can be inhibited by way of inactivating and/or sequestering the protein. As such, inhibiting the effects of a protein required for NAD degradation and/or tryptophan catabolism can be accomplished by using a transdominant negative mutant. Alternatively an antibody specific for a protein required for NAD degradation and/or tryptophan catabolism (e.g., an antagonist to CD38) may be used. In one embodiment, the antagonist is a protein and/or compound having the desirable property of interacting with a protein required for NAD degradation and/or tryptophan catabolism and thereby sequestering the protein.

As will be understood by one skilled in the art, any antibody that can recognize and bind to an antigen of interest is useful in the present invention. Methods of making and using antibodies are well known in the art. For example, polyclonal antibodies useful in the present invention are generated by immunizing rabbits according to standard immunological techniques well-known in the art (see, e.g., Harlow et al., 1988, In: Antibodies, A Laboratory Manual, Cold Spring Harbor, N.Y.). Such techniques include immunizing an animal with a chimeric protein comprising a portion of another protein such as a maltose binding protein or glutathione (GSH) tag polypeptide portion, and/or a moiety such that the antigenic protein of interest is rendered immunogenic (e.g., an antigen of interest conjugated with keyhole limpet hemocyanin, KLH) and a portion comprising the respective antigenic protein amino acid residues. The chimeric proteins are produced by cloning the appropriate nucleic acids encoding the marker protein into a plasmid vector suitable for this purpose, such as but not limited to, pMAL-2 or pCMX.

However, the invention should not be construed as being limited solely to methods and compositions including these antibodies or to these portions of the antigens. Rather, the invention should be construed to include other antibodies, as that term is defined elsewhere herein, to antigens, or portions thereof. Further, the present invention should be construed to encompass antibodies, inter alia, bind to the specific antigens of interest, and they are able to bind the antigen present on Western blots, in solution in enzyme linked immunoassays, in fluorescence activated cells sorting (FACS) assays, in magnetic affinity cell sorting (MACS) assays, and in immunofluorescence microscopy of a cell transiently transfected with a nucleic acid encoding at least a portion of the antigenic protein, for example.

One skilled in the art would appreciate, based upon the disclosure provided herein, that the antibody can specifically bind with any portion of the antigen and the full-length protein can be used to generate antibodies specific therefor. However, the present invention is not limited to using the full-length protein as an immunogen. Rather, the present invention includes using an immunogenic portion of the protein to produce an antibody that specifically binds with a specific antigen. That is, the invention includes immunizing an animal using an immunogenic portion, or antigenic determinant, of the antigen.

Once armed with the sequence of a specific antigen of interest and the detailed analysis localizing the various conserved and non-conserved domains of the protein, the skilled artisan would understand, based upon the disclosure provided herein, how to obtain antibodies specific for the various portions of the antigen using methods well-known in the art or to be developed.

The skilled artisan would appreciate, based upon the disclosure provided herein, that that present invention includes use of a single antibody recognizing a single antigenic epitope but that the invention is not limited to use of a single antibody. Instead, the invention encompasses use of at least one antibody where the antibodies can be directed to the same or different antigenic protein epitopes.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.).

Monoclonal antibodies directed against full length or peptide fragments of a protein or peptide may be prepared using any well-known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein. Further, the antibody of the invention may be "humanized" using the technology described in, for example, Wright et al., and in the references cited therein, and in Gu et al. (1997, Thrombosis and Hematocyst 77:755-759), and other methods of humanizing antibodies well-known in the art or to be developed.

The present invention also includes the use of humanized antibodies specifically reactive with epitopes of an antigen of interest. The humanized antibodies of the invention have a human framework and have one or more complementarity determining regions (CDRs) from an antibody, typically a mouse antibody, specifically reactive with an antigen of interest. When the antibody used in the invention is humanized, the antibody may be generated as described in Queen, et al. (U.S. Pat. No. 6,180,370), Wright et al., (supra) and in the references cited therein, or in Gu et al. (1997, Thrombosis and Hematocyst 77(4):755-759). The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, such as an epitope on an antigen of interest, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to the humanized immunoglobulin coding sequences, including naturally-associated or heterologous promoter regions. The expression control sequences can be eukaryotic promoter systems in vectors capable of transforming or transfecting eukaryotic host cells or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

The invention also includes functional equivalents of the antibodies described herein. Functional equivalents have binding characteristics comparable to those of the antibodies, and include, for example, hybridized and single chain antibodies, as well as fragments thereof. Methods of producing such functional equivalents are disclosed in PCT Application WO 93/21319 and PCT Application WO 89/09622.

Functional equivalents include polypeptides with amino acid sequences substantially the same as the amino acid sequence of the variable or hypervariable regions of the antibodies. "Substantially the same" amino acid sequence is defined herein as a sequence with at least 70%, preferably at least about 80%, more preferably at least about 90%, even more preferably at least about 95%, and most preferably at least 99% homology to another amino acid sequence (or any integer in between 70 and 99), as determined by the FASTA search method in accordance with Pearson and Lipman, 1988 Proc. Nat'l. Acad. Sci. USA 85: 2444-2448. Chimeric or other hybrid antibodies have constant regions derived substantially or exclusively from human antibody constant regions and variable regions derived substantially or exclusively from the sequence of the variable region of a monoclonal antibody from each stable hybridoma.

Single chain antibodies (scFv) or Fv fragments are polypeptides that consist of the variable region of the heavy chain of the antibody linked to the variable region of the light chain, with or without an interconnecting linker. Thus, the Fv comprises an antibody combining site.

Functional equivalents of the antibodies of the invention further include fragments of antibodies that have the same, or substantially the same, binding characteristics to those of the whole antibody. Such fragments may contain one or both Fab fragments or the F(ab')2 fragment. The antibody fragments contain all six complement determining regions of the whole antibody, although fragments containing fewer than all of such regions, such as three, four or five complement determining regions, are also functional. The functional equivalents are members of the IgG immunoglobulin class and subclasses thereof, but may be or may combine with any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Exemplary constant regions are gamma 1 (IgG1), gamma 2 (IgG2), gamma 3 (IgG3), and gamma 4 (IgG4). The light chain constant region can be of the kappa or lambda type.

The immunoglobulins of the present invention can be monovalent, divalent or polyvalent. Monovalent immunoglobulins are dimers (HL) formed of a hybrid heavy chain associated through disulfide bridges with a hybrid light chain. Divalent immunoglobulins are tetramers ($H_2L_2$) formed of two dimers associated through at least one disulfide bridge.

Methods of the Invention

In one aspect, the invention relates to methods of modulating various metabolic processes in a subject, such as for example modulating tryptophan metabolism, modulating kynurenine to tryptophan ratio, regulating a kynurenine pathway in a subject, regulating a methoxyindole pathway in a subject, and regulating a NAD salvage pathway in a subject. In one aspect, the invention relates to methods of modulating the level or activity of proteins involved in tryptophan metabolism, for example regulating the activity of IDO. In yet another aspect, the invention relates to methods of modulating the level of metabolites of tryptophan, for example regulating the level of NAD+ or serotonin. In one embodiment, the invention relates to method of modulating expression of a gene or gene product that is dependent on NAD+ levels, e.g. increasing Sirtuin activation or decreasing CD16 expression.

In certain embodiments, the methods comprise administering to the subject a therapeutically effective amount of a modulator of the invention, or a salt or solvate thereof. In another aspect, the invention relates to methods of treating diseases or disorders associated with metabolic processes in a subject, such as for example diseases or disorders associated with high levels of tryptophan catabolism, diseases or disorders associated with an elevated kynurenine to tryptophan ratio, and diseases or disorders associated with decreased serotonin in a subject, diseases or disorders associated with elevated CD16 expression, diseases or disorders associated with decreased Sirtuin activation, the methods including administering to the subject a therapeutically effective amount of a modulator of the invention, or a salt or solvate thereof.

In other aspects, the invention relates to methods of increasing biosynthesis of chemical entities in a subject, for example serotonin and/or melatonin, the methods comprising administering to the subject a therapeutically effective amount of a modulator of the invention, or a salt or solvate thereof. By increasing the biosynthesis of serotonin, the modulator can be used for treating mood disorders, for example depression. By increasing the biosynthesis of melatonin on the other hand, the modulator can be used for treating sleep disorders, for example insomnia.

In other aspects, the invention relates to methods of decreasing biosynthesis, and/or the levels, of chemical entities in a subject, for example kynurenine metabolites, the methods comprising administering to the subject a therapeutically effective amount of a modulator of the invention, or a salt or solvate thereof. By decreasing the biosynthesis of kynurenine metabolites, a modulator of the invention can be used for treating various diseases and disorders. In some embodiments, the diseases or disorders can be depressive disorders, and bipolar disorders.

In one aspect, the invention also relates to using a modulator in a method of increasing immunogenicity of an immunogenic agent in a subject, the method comprising administering to the subject a therapeutically effective amount of a modulator of the invention, or a salt or solvate thereof, where the modulator is administered either before, after, or concomitantly with the immunogenic agent. In some embodiments, the immunogenic agent can be a vaccine, a genetically modified T cells, or a therapeutic antibody. For example, in certain embodiments, the immunogenic agent comprises a T cell that has been modified to express a chimeric antigen receptor. Exemplary antigens to which the immune response is directed include, but are not limited to, a viral antigen, a bacterial antigen, a parasitic antigen, a cancer antigen, a tumor-associated antigen, and a tumor-specific antigen.

In another aspect, the invention relates to using the kynurenine to tryptophan ratio in a subject for designing personalized medicine approaches for various diseases or disorders, for example diseases or disorders associated with modulating kynurenine to tryptophan ratio. Personalized medicine approaches include for example a method of determining whether the kynurenine to tryptophan ratio is elevated in a subject, comprising: measuring the kynurenine to tryptophan ratio in the subject; and comparing the kynurenine to tryptophan ratio in the subject with a predetermined kynurenine to tryptophan ratio. In one embodiment, the method further comprises: administering to the subject a therapeutically effective amount of a modulator of the invention, or a salt or solvate thereof.

The methods of the invention are designed to be used in various subjects, in particular in human subjects. While the methods of the invention seek to address a variety of diseases and disorders, in some embodiments, the disease or disorder has an immunosuppressive character. In other embodiments, the diseases or disorders include viral infections, bacterial infections, parasitic infections, comorbidities of viral infections, cancers, neurodegenerative diseases or disorders, immune-mediated disorders, inflammatory diseases, cardiovascular diseases, kidney diseases, autoimmune diseases, lupus, systemic lupus erythematosus, age-related disorders, diabetes, obesity, insulin resistance, eating disorders, metabolic syndrome, pain, migraine, rheumatoid arthritis, osteoporosis, sleep disorders, mood disorders, psychiatric diseases or disorders, neurologic diseases or disorders, depression and schizophrenia. In one embodiment, a viral infection is malaria. In one embodiment, a viral infection is Hepatitis C virus (HCV). In one embodiment, a viral infection is human immunodeficiency virus (HIV) infection. In one embodiment, a disease is a virus-associated co-morbidity. In one embodiment, a disease is an HCV-associated co-morbidity. In one embodiment, a disease is an HIV-associated co-morbidity. In one embodiment, a comorbidity of a viral infection is HIV-associated neurocognitive disorders (HAND), HIV-associated viral infections, cardiovascular disease, kidney disease, obesity, autoimmune diseases, Crohn's disease, rheumatoid arthritis, cancer, atherosclerosis, and central nervous system diseases. In another embodiment, the mood disorder is depression. In one embodiment, the cancer is selected from the group consisting of multiple myeloma, leukemia, lymphoma, breast cancer, lung cancer, stomach cancer, liver cancer, blood cancer, bone cancer, pancreatic cancer, skin cancer, head or neck cancer, skin or eye melanoma, sarcoma of the uterus, ovarian cancer, rectal cancer, anal cancer, colorectal cancer, fallopian tube carcinoma, endometrium carcinoma, cervical cancer, small intestine cancer, endocrine gland cancer, thyroid cancer, parathyroid gland cancer, renal cell carcinoma, soft tissue sarcoma, urethra cancer, prostate cancer, bronchial cancer, myeloma, neuroma, and cutaneous squamous cell carcinoma. In one embodiment, the cardiovascular disease is selected from the group consisting of stroke, myocardial infarction and sudden cardiac death. In another embodiment, the neurodegenerative disease or disorder is selected from the group consisting of Alzheimer's disease (AD), Parkinson's disease (PD), Huntington's disease (HD), frontotemporal dementia (FTLD), amyotrophic lateral sclerosis (ALS), epilepsy and Charcot-Marie-Tooth disease (CMT).

Prodrug Therapy

The invention includes methods comprising administration of prodrugs. "Prodrug," as used herein, means a compound which is convertible in vivo by metabolic means (e.g., by hydrolysis) to a compound useful in the present invention, i.e., a nicotinamide riboside prodrug. Various forms of prodrugs are known in the art, for example, as discussed in Bundgaard, (ed.), Design of Prodrugs, Elsevier (1985); Widder et al. (ed.), Methods in Enzymology, vol. 4, Academic Press (1985); Krogsgaard-Larsen et al. (ed). "Design and Application of Prodrugs," Textbook of Drug Design and Development, Chapter 5, 113-191 (1991), Bundgaard et al., 1992, J. Drug Deliv. Rev. 8:1-38, Bundgaard, 1988, J. Pharm. Sci. 77:285 et seq.; and Higuchi and Stella (eds.), Prodrugs as Novel Drug Delivery Systems, American Chemical Society (1975). In one non-limiting example, the esters and amides of a-carboxylic acid are prepared as prodrugs to improve oral bioavailability, whereby the ester or amide is stable in the stomach and gastrointestinal tract, is optimally transported across the lining of the gastrointestinal tract into the bloodstream, and is then converted by the ubiquitous esterases or amidases in the blood to the carboxylic acid moiety. In another non-limiting example, the ester prodrug is the methyl, ethyl, n-propyl or i-propyl ester. In another non-limiting example, the amide prodrug is the isopropyl amide or the 2,2,2-trifluoroethyl amide.

Salts

The compound useful in the invention may form salts with acids or bases, and the use of such salts is included in the present invention. In one embodiment, the salts are pharmaceutically-acceptable salts. The term "salts" embraces addition salts of free acids or free bases that are compounds useful within the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared from the corresponding compound by reacting, for example, the appropriate acid or base with the compound.

Combination Therapy

In one embodiment, the invention relates to a combination therapy wherein a NAD precursor is used in combination with one or more additional therapeutic agent. In various embodiments, an additional therapeutic agent may be one or more of a CD38 inhibitor, a Sirtuin activator, an IDO antagonist, a modulator of the kynurenine pathway, or a therapeutic agent for treatment of a disease.

In one embodiment, a first therapeutic agent is administered in combination with one or more additional therapeutic agent for the treatment of a disease or disorder. In another embodiment, one or more additional therapeutic agent is administered simultaneously, prior to, or after administration a first therapeutic agent. In yet another embodiment, one or more additional therapeutic agent is co-administered with a first therapeutic agent. In yet another embodiment, one or more additional therapeutic agent is co-administered and co-formulated with a first therapeutic agent of the invention.

In some embodiments, one or more additional modulator of NAD+, a gene or gene product dependent on NAD+ levels or tryptophan catabolism can be used, such as, for example, an antagonist of the kynurenine pathway, a Sirtuin agonist, an immune checkpoint blocker, a CD38 antagonist.

In some embodiments, one or more additional pharmaceutical agents can be used, such as, for example, immunomodulatory or immunotherapeutic drugs, such as immune checkpoint inhibitor monoclonal antibodies, thalidomide, lenalidomide (Len) and pomalidomide, steroids, such as dexamethasone, anticancer antibodies, such as nivolumab and ipilimumab, proteasome inhibitors, such as bortezomib, salinosporamide, anticancer drugs, such as romidepsin, and taxanes, oncolytic viral therapy agents, such as adenovirus, reovirus, or herpes simplex.

In some embodiments, the second therapeutic agent is an antiretroviral drug. In other embodiments, the second therapeutic agent is a reverse-transcriptase inhibitor. In other embodiments, the second therapeutic agent can be lamivudine, zidovudine, lopinavir, ritonavir, abacavir, tenofovir, emtricitabine, rilpivirine, efavirenz, elvitegravir, cobicistat, dolutegravir, darunavir, atazanavir, and raltegravir.

In certain embodiments, a modulator of the invention may be administered to a subject in conjunction with (e.g., before, simultaneously, or following) any number of relevant treatment modalities including chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, a modulator of the invention, is administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, a modulator of the invention is administered following B-cell ablative therapy with agents that react with CD20, e.g., Rituxan.

Dosing

A modulator of the invention, alone or in combination with another therapeutic agent, can be administered to a cell, a tissue, or a subject, to provide a therapeutic effect related to NAD+ concentration, expression and/or activity of a gene or gene product dependent of NAD+ concentration (e.g. CD16 expression and Sirtuin activation), tryptophan metabolism, or kynurenine to tryptophan ratio. Methods for the safe and effective administration of therapeutic agents are known to those skilled in the art. For instance, the administration of nicotinamide riboside (e.g. Niagen®, Nia-Cell®), is described in the literature. Dosages of modulators of the invention may range from about 0.1 µg/day to 10,000 mg/day, from about 1 µg/day to 1000 mg/day, and from about 10 µg/day to 100 mg/day, and any and all whole or partial increments there between.

Stated in terms of subject body weight, dosages may range from about 0.1 µg/kg/day to about 1000 mg/kg/day, from about 10 µg/kg/day to about 500 mg/kg/day, from about 20 µg/kg/day to about 100 mg/kg/day, from about 50 µg/kg/day to about 50 mg/kg/day, and from about 0.10 mg/kg/day to about 5 mg/kg/day, and any and all whole or partial increments there between.

Oral dosages may range from about 0.1 µg/day to about 10,000 mg/day, from about 1 µg/day to about 1000 mg/day, from about 10 µg/day to about 100 mg/day, and from about 8 mg/day to about 80 mg/day, and any and all whole or partial increments there between.

Stated in terms of subject body weight, oral dosages may range from about 0.1 µg/kg/day to about 1000 mg/kg/day, from about 10 µg/kg/day to about 500 mg/kg/day, from about 20 µg/kg/day to about 100 mg/kg/day, from about 50 µg/kg/day to about 50 mg/kg/day, and from about 0.10 mg/kg/day to about 5 mg/kg/day, and any and all whole or partial increments there between.

Modulators of the invention can be administered in a dose range of from about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, and any and all whole or partial increments there between.

In some embodiments, the dose of a modulator of the invention is from about 0.0001 mg to about 1000 mg. In some embodiments, a dose of a modulator used in compositions and methods described herein is less than about 1000 mg, or less than about 800 mg, or less than about 600 mg, or less than about 500 mg, or less than about 300 mg, or less than about 200 mg, or less than about 100 mg, or less than about 80 mg, or less than about 60 mg, or less than about 50 mg, or less than about 30 mg, or less than about 20 mg, or less than about 10 mg, or less than about 5 mg, or less than about 2 mg, or less than about 0.5 mg, and any and all whole or partial increments there between. Similarly, in some embodiments, a dose of a second compound as described herein is less than about 1000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments there between.

Pharmaceutical Composition

For administration of a modulator of the invention, for example nicotinamide riboside, alone or in conjunction with an additional therapeutic agent, to a subject, the modulator and any additional therapeutic agent can be suspended in any pharmaceutically acceptable carrier, for example, sterile water or buffered aqueous carriers, such as glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey), the disclosure of which is incorporated by reference as if set forth in its entirety herein.

The pharmaceutical compositions comprising a modulator of the invention, alone or in combination with an additional therapeutic agent, may be prepared, packaged, or sold in the form of a sterile injectable aqueous or oily suspension or solution. This suspension or solution may be formulated according to the known art, and may comprise, in addition to the active ingredient, additional ingredients such as dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

The compositions used in the methods of the invention are preferably administered to the subject as a pharmaceutical or veterinary composition, which includes systemic and topical formulations. Among these, preferred are formulations suitable for inhalation, or for respirable, buccal, oral, rectal, vaginal, nasal, intrapulmonary, ophthalmic, optical, intracavitary, intratracheal, intraorgan, topical (including buccal, sublingual, dermal and intraocular), parenteral (including subcutaneous, intradermal, intramuscular, intravenous and intraarticular) and transdermal administration, among others. The route(s) of administration will be readily apparent to the skilled artisan and will depend upon any number of factors including the type and severity of the disease being treated, the type and age of the veterinary or human subject being treated.

The compositions used in the methods of the invention may be administered to the lungs of a subject by any suitable means, but are preferably administered by generating an aerosol or spray comprised of respirable, inhalable, nasal or intrapulmonarily delivered particles comprising the active compound, which particles the subject inhales, i.e., by inhalation administration. The respirable particles may be liquid or solid. Particles comprising the active compound for practicing the present invention should include particles of respirable or inhalable size; that is, particles of a size sufficiently small to pass through the mouth and larynx upon inhalation and into the bronchi and alveoli of the lungs. In general, particles ranging from about 0.05, about 0.1, about 0.5, about 1, about 1.5 to about 5, about 6, about 7, about 8, about 10 microns in size, more particularly particles about 0.5 to less than about 5 microns in size, are respirable or inhalable. When particles of non-respirable size are included in the aerosol or spray, they tend to deposit in the throat and be swallowed. Thus, the quantity of non-respirable particles in the aerosol or spray is preferably minimized when intended for respirable administration or by inhalation. For nasal or intrapulmonary administration, a particle size in the range of about 10, about 11, about 15, about 20 to about 25, about 30, about 40, about 50, and sometimes even up to about 100 and about 500 microns is preferred to ensure retention in the nasal or pulmonary cavity. Pulmonary instillation is particularly useful in treating newborns.

Liquid pharmaceutical compositions used in the methods of the invention for producing an aerosol or spray may be prepared by combining the active compound with a stable vehicle, such as sterile pyrogen free water. Solid particulate compositions containing respirable dry particles of micronized active compound may be prepared by grinding dry active compound with a mortar and pestle, and then passing the micronized composition through a 400 mesh screen to break up or separate out large agglomerates. A solid particulate composition comprised of the active compound may optionally contain a dispersant which serves to facilitate the formation of an aerosol. A suitable dispersant is lactose, which may be blended with the active compound in any suitable ratio, e.g., a 1 to 1 ratio by weight. Other therapeutic and formulation compounds may also be included, such as a surfactant to improve the state of surfactant in the lung and to help with the absorption of the active agent.

Aerosols of liquid particles may be produced by any suitable means, such as with a nebulizer. See, e.g., U.S. Pat. No. 4,501,729. Nebulizers are commercially available devices which transform solutions or suspensions of the active ingredient into a therapeutic aerosol mist either by means of acceleration of a compressed gas, typically air or oxygen, through a narrow venturi orifice or by means of ultrasonic agitation. Suitable compositions for use in nebulizer consist of the active ingredient in liquid carrier, the active ingredient comprising up to 40% w/w of the compositions, but preferably less than 20% w/w, and the carrier is typically water or a dilute aqueous alcoholic solution, preferably made isotonic with body fluids by the addition of, for example sodium chloride. Optional additives include preservatives if the composition is not prepared sterile, for example, methyl hydroxybenzoate, antioxidants, flavoring agents, volatile oils, buffering agents and surfactants.

Aerosols of solid particles may likewise be produced with any solid particulate medicament aerosol generator. Aerosol generators for administering solid particulate medicaments to a subject produce particles which are respirable, as explained above, and they generate a volume of aerosol containing a predetermined metered dose of a medicament at a rate suitable for human administration. Examples of such aerosol generators include metered dose inhalers and insufflators.

Pharmaceutical compositions that are useful in the methods of the invention may be administered systemically in oral solid formulations, ophthalmic, suppository, aerosol, topical or other similar formulations. In addition to the compounds of the invention, or a biological equivalent thereof, such pharmaceutical compositions may contain pharmaceutically-acceptable carriers and other ingredients known to enhance and facilitate drug administration.

The pharmaceutical compositions described herein can be prepared alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

A pharmaceutical composition used in the methods of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition used in the methods of the invention will vary, depending upon the identity, size, and condition of the subject treated and further depending upon the route by which the composition is to be administered. By way of example, the composition may comprise between 0.1% and 100% (w/w) active ingredient. In addition to the active ingredient, a pharmaceutical composition of the invention may further comprise one or more additional pharmaceutically active agents.

Controlled- or sustained-release formulations may be made using conventional technology.

A formulation of a pharmaceutical composition used in the methods of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition used in the methods of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

In yet another embodiment, compositions used in the methods of the invention may be administered to the desired location of a subject by a transdermal patch. A transdermal patch is meant a system capable of delivery of a compound to a subject via the skin, or any suitable external surface, including mucosal membranes, such as those found inside the mouth. Such delivery systems generally comprise a flexible backing, an adhesive and a compound retaining matrix, the backing protecting the adhesive and matrix and the adhesive holding the whole on the skin of the subject. On contact with the skin, the compound-retaining matrix delivers the compound to the skin, the compound then passing through the skin into the subject's system.

Certain embodiments of the invention provide a pharmaceutical preparation/dosage formulation provided in the form of a transdermal patch and formulated for sustained release formulation, in a therapeutically effective amount sufficient to treat a disease associated with activation of an immune cell (e.g., rheumatoid arthritis) in a patient, wherein the dosage formulation, when administered (provided as a patch) to the patient, provides a substantially sustained dose over at least about 2 hours, 4 hours, 6 hours, 8, hours, 12 hours, 20 hours, or at least about 24 hours.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, subcutaneous, intraperitoneal, intramuscular, intrasternal injection, bolus injections, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

A pharmaceutical composition used in the methods of the invention may be prepared, packaged, or sold in a formulation suitable for pulmonary administration via the buccal cavity. Such a formulation may comprise dry particles that comprise the active ingredient and that have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions used in the methods of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful in pulmonary delivery are also useful in intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition used in the methods of the invention may be prepared, packaged, or sold in a formulation suitable for buccal administration. Such formulations may, for example, be in the form of tablets or lozenges made using conventional methods, and may, for example, contain 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Typically, dosages of the compound of the invention which may be administered to a subject, preferably a human, will vary depending upon any number of factors, including but not limited to, the type of animal and type of disease state being treated, the age of the subject and the route of administration.

The compound can be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the subject, and the like.

Kits

In some embodiments, the present invention also includes pharmaceutical kits and/or research probes useful, for example, in the treatment or prevention of diseases or disorders associated with one or more of NAD+ concentration, an activity of a gene or gene product affected by NAD+ concentration (e.g. CD16 expression and Sirtuin activation), tryptophan metabolism, or kynurenine to tryptophan ratio. In one aspect, the invention relates to a kit for conducting a method of the invention, comprising: an amount of a modulator of the invention, or a salt or solvate thereof, and an instruction manual for the use thereof. Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

In some embodiments, the present invention also includes probes useful, for example, in the treatment or prevention of, or in the imaging or theranostic approaches to tryptophan metabolism associated diseases or disorders. In another aspect, the invention relates to a probe for imaging or diagnosing a disease or disorder associated with any of tryptophan metabolism, kynurenine to tryptophan ratio, a kynurenine pathway, biosynthesis of serotonin, or biosynthesis of melatonin in a subject.

In one aspect, the invention provides methods comprising the use of theranostics. Theranostics are compounds, formulations and compositions, capable of functioning as both therapeutic agents and diagnostic agents. For example, a probe of the invention can modulate tryptophan metabolism, kynurenine to tryptophan ratio, and/or a kynurenine pathway, and at the same time provide for the possibility of imaging the distribution of various parts of a kynurenine pathway distribution in a cell, tissue, organ, or entire body. Modern approaches to theranostics have been described by Xie et al., 2010, Adv Drug Deliv Rev, 62(11): 1064-1079, and Pene et al., 2009, Crit Care Med., 37(1 Suppl):S50-8, descriptions incorporated herein in their entirety.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

Mouse Model

In one embodiment, the invention provides a Tg26$^{+/-}$ ApoE$^{-/-}$ mouse model without HIV replication, despite the integration of HIV provirus into all cells. In one embodiment, this model may be used to determine the effects of HIV infection, when the virus is fully suppressed, but not eradicated as in a latent and/or persistent infection, fully suppressed under antiretroviral therapy.

In one embodiment, this model can be used to model cardiovascular diseases, which can be used to interrogate and treat the contribution of HIV as well as HIV-1-associated co-morbidities such as cardiovascular diseases and vascular dementia. In one embodiment, this model can be used to test targets such as CD38, NAD+ precursors, IDO antagonists, as well as other targets for treatment of HIV-1-associated co-morbidities such as atherosclerosis/CVD and vascular dementia in the setting of HIV infection. In one embodiment, the animal model can be used to test targets including, but not limited to, targets involving the kynurenine pathway, IDO, CD38, NAD+ precursors, and activation of Sirtuin 1 as well as targets involved in other cellular and molecular mechanisms underlying HIV-1-associated cardiovascular diseases and vascular dementia. In one embodiment, this model may also be used to determine the ability of various treatments to function as latency reversing agents by determining the activation of HIV gene expression in various mouse tissues upon treatment with various compounds. In one embodiment, the model can be used to evaluate the compounds described here for the treatment of atherosclerosis, cardiovascular disease and vascular dementia.

EXPERIMENTAL EXAMPLES

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: HIV Eradicating NAD Metabolism

NAD+ metabolism is centric to chronic immune activation, immune suppression, latency, as well as co-morbidities in HIV infection associated with accelerated aging. Without being bound by a particular theory, it is hypothesized that tryptophan catabolism, a known mediator or immune suppression, is driven by NAD+ turnover, as a consequence of virus induced NADase activity. Further, without being bound by a particular theory, it is hypothesized that HIV latency as well as chronic inflammation are driven by the loss of NAD+ via reduced Sirtuin-1 deacetlyase activity. Therefore, this study presents a method for the use of NAD+ precursors and NAD+ glycohydrolase antagonists for the treatment and eradication of latent HIV infection.

A Metabolism Based, NAD+ Centric Hypothesis for HIV Eradication

Without being bound by a particular theory, it is hypothesized that eradication of HIV in the context of cART, will require addressing unique mechanisms whereby HIV induces chronic inflammation, immune suppression, and the establishment of latent virus pools. Studies have demonstrated the potential importance of the NK-1R/SP and M-CSF/cFMS pathway in monocyte macrophage activation/differentiation, HIV replication, and likely function in the pathogenesis of HIV infection (FIG. 1). These pathways both contribute to alternative macrophage activation/M2 polarization via Substance P and M-CSF production induced in HIV infection. Additionally, studies demonstrate accumulation of CD163+/CD16+ monocytes in HIV and SIV infection, likely precursors of M2 macrophages (Smith et al., AIDS Res Hum Retroviruses. 2008, 24:417-421; Smith et al., J Neurovirol. 2008, 14:318-326). Accumulation of macrophages in lymphoid and other tissues in the setting of HIV infection likely provides a setting for additional immune suppression by M2 macrophages in HIV/AIDS (Fischer et al., Cur HIV Res. 2014, 12:201-212). An additional pathway, which is a major focus here, is the action of IDO. IDO, like M-CSF, exhibits a highly potent immunosuppressive action, actually required in pregnancy in order to maintain the survival of an allogeneic conceptus (Chaouat et al., J Assist Reprod Genet. 2007, 24:494-505). IDO not only modulates cytokine production in macrophages in vitro, but the degradation of tryptophan and resulting kynurenine pathway metabolites contribute to T cell anergy, apoptosis, and immune suppression. The mechanisms contributing to M2 polarization by substance P, M-CSF, TNFα, IFNγ, and IDO are illustrated in FIG. 1. IDO is most likely a central mediator of immune polarization.

There is clear evidence for the excess catabolism of tryptophan and increased kynurenine/tryptophan (K/T) ratios in the setting of cART treatment (Tenorio et al., J Infect Dis. 2014 Oct. 15; 210(8):1248-59; Bipath et al, BMC Infect Dis. 2015 Aug. 19; 15:346; Drewes et al., J Neurovirol. 2015 August; 21(4):449-63; Gaardbo et al., J Acquir Immune Defic Syndr. 2015 Jul. 11), and this pathway plays an important role in viral persistence in chronic viral infections, in addition to HIV (Mehraj and Routy, Int J Tryptophan Res. 2015 Aug. 4; 8:41-8). Altered K/T ratio correlated with impaired neurocognition in HIV patients (Cassol et al., Aids. 2014; 28(11):1579-91). Therefore, this pathway is critical to address in order to fully reconstitute immune function in HIV infection and clear reservoirs of HIV infection. Without being bound by a particular theory, as the ultimate catabolism of tryptophan leads to NAD+ production, the turnover and reduction in cellular NAD+ is believed to contribute to immune suppression, chronic immune activation, and latency. Without being bound by a particular theory, it is hypothesized that the catabolism of NAD+ is carried out by the ecto-enzyme CD38, where expression is increased on CD4+ and CD8+ T cells during HIV infection. NAD+ is cofactor for the deacetylase Sirtuin-1, a key player in metabolic control from yeast to man, as well as protection from aging. Without being bound by a particular theory, it is believed that NAD+ deficiency reduces Sirtuin-1 function, in turn, promoting chronic immune activation, accelerated aging and HIV co-morbidities, as well as latency in memory T cells. Therefore, combination therapeutic strategies are presented to ameliorate these defects in immunity, aging, reverse latency and contribute to the eradication of HIV infection in latent and persistent virus reservoirs through immune reconstitution. The contributions of individual components of these pathways are discussed in detail below.

Figure 2A:
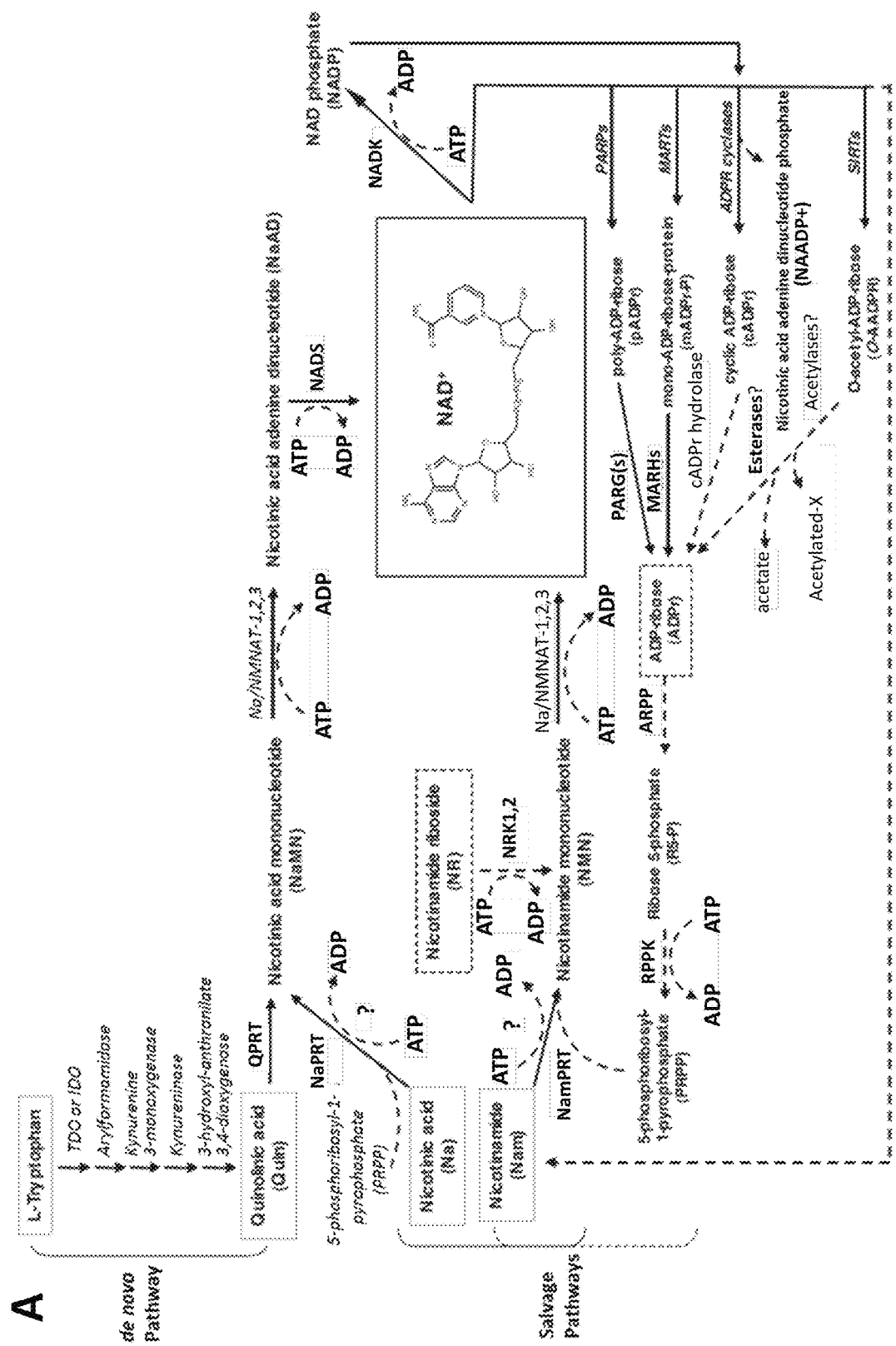
FIG. 2A and FIG. 2B, depicts schematic illustrations of NAD+ metabolic pathways.
Figure 2B:
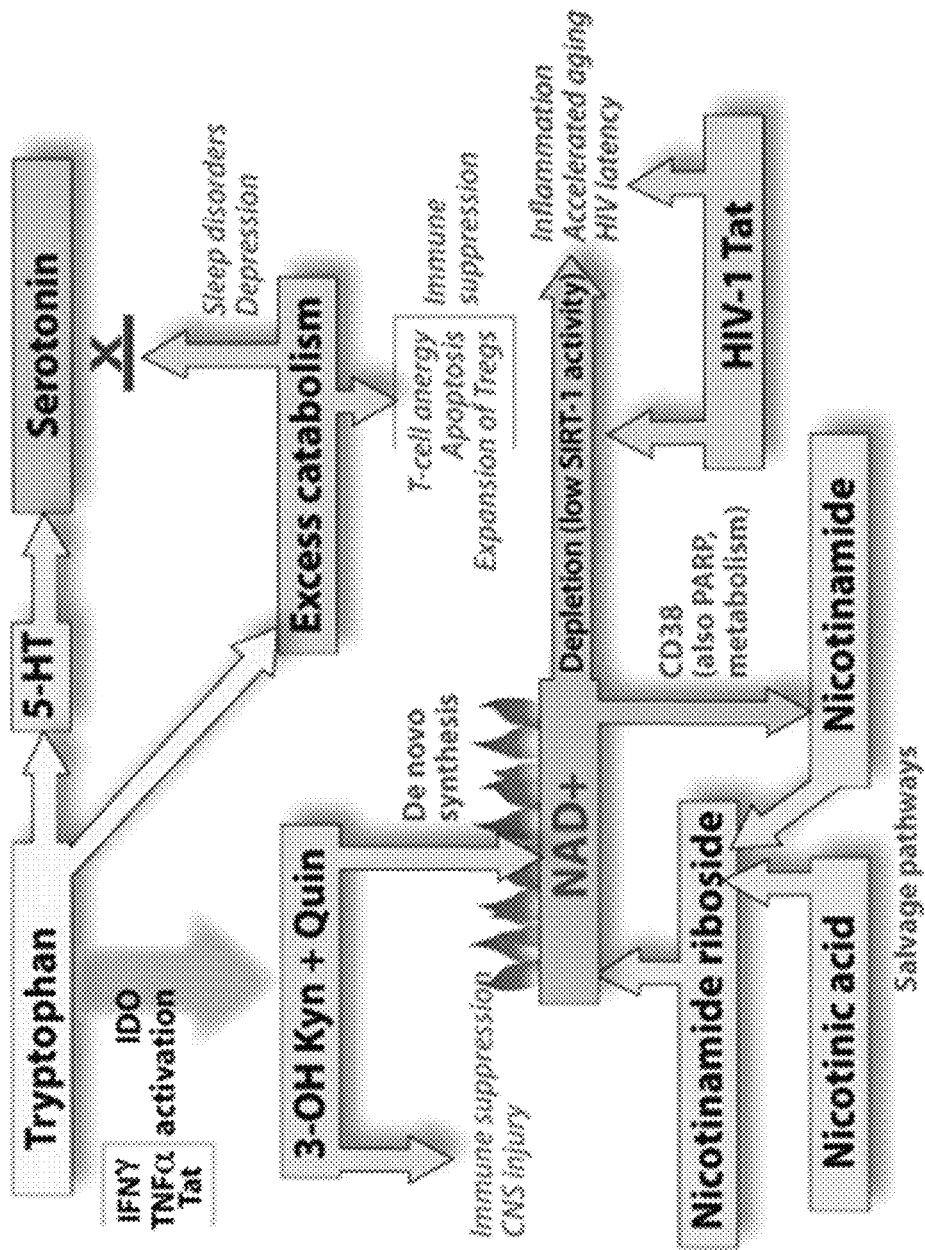

Tryptophan Metabolism (IDO and the Kynurenine Pathway):

Tryptophan is an essential amino acid that is involved, not only in production or proteins by incorporation during protein synthesis, but also in the production or key regulators of metabolism, nutrition, and sleep (e.g. serotonin and melatonin). With relevance to HIV infection and AIDS, the catabolism of tryptophan via the kynurenine pathway is a major mechanism for immune tolerance, with critical relevance in pregnancy (survival of the allogeneic conceptus/fetus), transplant biology, cancer therapeutics, as well as normal immunologic control (Mellor and Munn, Immunol Today. 1999 October; 20(10):469-73; Grohmann et al., Trends Immunol. 2003 May; 24(5):242-8.). Increased production of the enzyme IDO (indoleamine 2,3,-dioxygenase) is exhibited in cancers, as a consequence of inflammatory signals such as interferons, NFkB activation, and TNF alpha, as well as the combined stimulus of LPS. With IDO promoting the rate limiting step in tryptophan breakdown, this process leads to reduced local levels of tryptophan as well as increased kynurenine metabolites (Prodinger et al., J Leukoc Biol. 2016 April; 99(4):583-94) that both contribute to immune suppression and HIV associated pathogenesis. The mechanism whereby regulatory myeloid cells degrade tryptophan as well as arginine (via arginase 1 in M2 macrophages) results in the accumulation of uncharged tRNAs in T cells, activation of GCN2 kinase in naïve and regulatory T cells, resulting in immune suppression via inhibition of effector T cell function (Boasso and Shearer, Curr Drug Metab. 2007 April; 8(3):217-23; Mellor and Munn, Nat Rev Immunol. 2008 January; 8(1):74-80; Barth and Raghuraman, Crit Rev Microbiol. 2014 November; 40(4):360-8; Schmidt and Schultze, Front Immunol. 2014 Aug. 11; 5:384). The inhibition of tryptophan catabolism is therefore and important target for immune modulation; IDO is the subject of intense investigation in clinical trials for cancer (Vacchelli et al., Oncoimmunology. 2014 Dec. 15; 3(10): e957994). The pathways involving tryptophan degradation initiated by IDO, and leading to the formation of NAD+, as well as salvage NAD+ synthetic and catabolic pathways are shown in FIG. 2A and FIG. 2B (Hassa et al., Microbiol Mol Biol Rev. 2006 September; 70(3):789-829). Without being bound by a particular theory, it is believed that the catabolism of tryptophan is driven by the need to produce NAD+, as a result of NAD+ destruction (primarily by CD38), leading to immune activation and, and HIV latency as discussed in the following sections.

HIV, NAD+, and Pellagra:

NAD+(nicotinamide adenine dinucleotide) is a molecule involved in all biological processes, including energy transfer, and is the active subject of investigation for therapeutics in many diseases which include Parkinson's disease, Alzheimer's disease, cardiovascular disease as well as aging (Mouchiroud et al., Crit Rev Biochem Mol Biol. 2013 July-August; 48(4):397-408). NAD+ is required for the action of Sirtuin deacetylases, where their action is limited by the availability of NAD+. Strategies that either increase NAD+ production via niacin related salvage pathways and/or strategies that prevent NAD+ consumption/degradation by downstream pathways are the subject of intense interest as therapeutic strategies for age related diseases.

Tryptophan catabolism is required for the de novo synthesis of NAD+, through the further metabolism of Qunolinic acid (Hassa et al., Microbiol Mol Biol Rev. 2006 September; 70(3):789-829). As shown in FIG. 2A, NAD+ is also formed from salvage pathways from dietary niacin (vitamin B3, containing nicotinic acid and nicotinamide). HIV infection induces NAD+ depletion in stimulated lymphocytes in symptomatic individuals (Bofill et al., J Biol Chem. 1995; 270(50):29690-7). As NAD+ is replace from salvage pathways and tryptophan, the drain on NAD+ may be more evident based on reduced tryptophan levels, or increased KYN metabolites. From the above discussion it is easy to see how tryptophan depletion could result in NAD+ deficiency, which would increase demands for niacin. Indeed, niacin deficiency is associated with pellagra, a disease involving dementia, diarrhea, and dermatologic disorders, with similarity to clinical findings in HIV infection (Murray, Med Hypotheses. 1999 November; 53(5):375-9). HIV infection in vitro decreases intracellular NAD+(Murray et al., Biochem Biophys Res Commun. 1995 Jul. 6; 212(1): 126-31). It has been proposed that niacin is a potential AIDS preventive factor (Murray, Med Hypotheses. 1999 November; 53(5):375-9), and niacin has been claimed to have some benefit in delaying the progression of HIV/AIDS prior to the advent of cART (32, 33). The hypothesis that HIV/AIDS results from a state of intracellular pellagra has been considered (Murray, Med Hypotheses. 1999 November; 53(5): 375-9). Although incompletely understood, these data taken together suggest the "metabolic shunting" of tryptophan and niacin toward the production of NAD+(Murray, Med Hypotheses. 1999 November; 53(5):375-9). The demonstration that nicotinamide supplementation increases plasma tryptophan levels in HIV infected subjects (Murray et al., Nutrition. 2001; 17(7-8):654-6) suggests that salvage pathway precursors of NAD+ are rate limiting for available tryptophan in HIV infection and supports our proposed utilization and treatment with nicotinamide riboside in the context of our proposed studies.

The hypothesis presented herein regarding increased tryptophan metabolism is different from those of other investigators primarily focusing on the inhibition of IDO to prevent tryptophan breakdown. While IDO is activated by inflammatory signals, this is likely due to NAD+ degradation, utilization, and increased turnover in HIV infection, and as a consequence, defective SIRT-1 acetylase activity leading increased inflammation (including increased IDO) in a vicious cycle. Inhibiting IDO alone, in the model presented herein, would not solve this problem therapeutically, particularly in the context of systemic HIV/SIV infection with downstream NAD+ demand. While preclinical studies in the SIV/rhesus macaques model demonstrated increased tryptophan metabolism and altered kynurenine to tryptophan Ratio (K/T) is predictive of neurological disease in the context of cART (Drewes et al., J Neurovirol. 2015 August; 21(4):449-63), IDO blockade with 1-methyl tryptophan was incapable of affecting tryptophan depletion or alterations in the kynurenine pathway (Dunham et al., AIDS Res Hum Retroviruses. 2013 February; 29(2):207-14). In fact, treatment actually increased the disturbance in K/T over-time in infected animals but not in controls. These results suggest a feedback mechanism involved, whereby additional IDO synthesis was stimulated. The outcome of this study, supports our interpretation that the altered K/T and resulting immune suppression is not simply due to the induction of IDO and tryptophan catabolism, but a more downstream depletion of NAD+. Blockade of IDO in this setting would be expected to actually further impair NAD+ levels, likely resulting in increases in IDO expression through feedback mechanisms, or increased immune activation as (see the discussion below related to SIRT-1 action).

CD38 as a NAD+ Degrading Enzyme, Biomarker for HIV Pathogenesis (CD8+/CD38+ T Cells) and Use of Quercetin and Small Molecules or Antibody Drugs, as a Therapeutic Agent Targeting CD38 NAD+ Glycohydrolase Activity:

Without being bound by a particular theory, it is believed that HIV induced CD38 expression, which remains elevated on CD8+ T cells under cART, is responsible for increased NAD+ turnover in HIV infection. CD38 is a type II transmembrane glycoprotein that functions as an NAD+ hydrolase with additional activity as an ADPR cyclase. The fact that only 1 molecule of cyclic ADPR is formed for every 100 molecules of NAD+ hydrolyzed has suggested that the major catalytic function of CD38 is NAD+ catabolism (Aksoy et al., Biochem Biophys Res Commun. 2006 Oct. 13; 349(1):353-9; Chini, Curr Pharm Des. 2009; 15(1):57-63). This is supported by CD38 knockout studies showing substantial increases in intracellular NAD+ levels (Aksoy et al., Biochem Biophys Res Commun. 2006 Oct. 13; 349(1): 353-9). CD38 expression on CD8+ T cells appears to be an important biomarker in HIV infection as expression increases in HIV infection/AIDS and furthermore, is a more reliable predictor of disease progression and subsequent CD4+ T cell decline than CD4+ T cell count (Liu et al., J Acquir Immune Defic Syndr Hum Retrovirol. 1997 Oct. 1; 16(2):83-92). CD38 expression on CD8+ T cells declines very slowly after the initiation of cART, even in patients with undetectable plasma viremia and is increased during "blips" of virus replication (Benito et al., AIDS Res Hum Retroviruses. 2004 February; 20(2):227-33). It has therefore been suggested that CD38 could be a marker of residual virus replication under cART (Benito et al., AIDS Res Hum Retroviruses. 2004 February; 20(2):227-33). While CD38 had been initially considered as a potential clue to explain niacin/tryptophan depletion in HIV infection, it has also been conceptually dismissed based on the notion that the purpose of extracellular NAD+ degradation would enable cellular uptake of NAD+/− generating metabolites such as niacinamide, thereby permitting the increased intracellular NAD+ production and thus protect cells. This notion was based on the concept that NAD+ could not be taken up by cells. This hypothesis, that CD38 protects intracellular NAD+ pools (Murray, Med Hypotheses. 1999 November; 53(5):375-9; Mehta et al., FASEB J. 1996 October; 10(12): 1408-17; Deterre et al., J Immunol. 1996 Aug. 15; 157(4): 1381-8) needs to be revisited in light of more recent evidence demonstrating 1) that NAD+ can be taken up intracellularly (Billington et al., J Biol Chem. 2008 Mar. 7; 283(10):6367-74), 2) that knockout of CD38 gene in mice increases NAD+ levels 10 to 20-fold with little detectable NAD hydrolase activity in tissues of these animals (Aksoy et al., Biochem Biophys Res Commun. 2006 Oct. 13; 349(1):353-9) and 3) that ectopically expressed CD38 in vitro results in lower intracellular NAD+ levels (Hu et al., J Proteome Res. 2014 Feb. 7; 13(2):786-95). Without being bound by a particular theory, it is hypothesized that NAD+ catabolism by CD38 is pivotal to upstream tryptophan catabolism, increased IDO synthesis, altered K/T ratios, and resulting immune dysfunction in HIV infection. As such, therapeutic targeting of CD38 using pharmacologic inhibitors is predicted to have major impact on the reservoir of HIV infection, likely in combination with NAD+ precursors (i.e. nicotinamide riboside). In addition, the use of IDO antagonists (1-Methyl Tryptophan) would be useful in the setting where NAD+ levels and NAD+ turnover were already stabilized by the aforementioned strategies.

CD38 antagonists include flavonoids quercetin and apigenin, two plant derived compounds with the ability to inhibit CD38 enzyme activity and increase intracellular NAD+ at micromolar concentrations (Escande et al., Diabetes. 2013 April; 62(4):1084-93; Kellenberger et al., Bioorg Med Chem Lett. 2011 Jul. 1; 21(13):3939-42), small molecules (Becherer et al., J Med Chem. 2015 Sep. 10; 58(17): 7021-56), and isatuximab (Sanofi), a drug under development for multiple myeloma that inhibits CD38 NAD glycohydrolase activity. There is considerable evidence demonstrating the efficacy of quercetin treatment in animal models of diabetes (Kim et al., Nutr Res Pract. 2011 April; 5(2): 107-11), spinal chord injury (Schultke et al., J Neurotrauma. 2003 June; 20(6):583-91; Schultke et al., Spinal Cord. 2010 February; 48(2):112-7), lung inflammation (Yang et al., Int Immunopharmacol. 2012 May; 13(1):73-81), as well as obesity (Dong et al., J Lipid Res. 2014 March; 55(3):363-74). The action of quercetin and apigenin flavinoids as CD38 NAD+ hydrolase antagonists has recently been established (Escande et al., Diabetes. 2013 April; 62(4): 1084-93; Kellenberger et al., Bioorg Med Chem Lett.

2011 Jul. 1; 21(13):3939-42). Comparison of CD38 knockout and wild-type mice revealed that CD38 is required for high fat diet induced obesity in mice (Dong et al., J Lipid Res. 2014 March; 55(3):363-74). Furthermore, the resistance of CD38 knockouts to obesity was mediated by increased NAD+ dependent SIRT-1 activity. With NAD+ dependent SIRT-1, quercetin has been demonstrated to reduce obesity associated adipose tissue macrophage infiltration in mice and this effect involves increased SIRT-1 activity, and reduced inflammatory cytokine levels in tissue and sera including TNFα, MCP-1, and IL-6 expression (Dong et al., J Lipid Res. 2014 March; 55(3):363-74). Quercetin is available as a supplement for human use, is not associated with side effects, and is easily administered orally as well as intravenously in animal studies. The connection between CD38, NAD+, and SIRT-1 (requiring NAD+) in inflammation and HIV latency is discussed in the following section.

Sirtuin-1 Deficiency, Due to NAD+ Depletion, Promotes Chronic Immune Activation, and Likely HIV Latency:

The Sirtuins represent a family of proteins (Silent Information Regulator Two) that is highly conserved from yeast (Sir2) to man. These proteins are class III histone deacetylases critically dependent on NAD+ for activity (Pinzone et al., Curr Drug Targets. 2013 Jun. 1; 14(6):648-52). The action of the evolutionarily conserved SIRT-1 is a pivotal control point in metabolism, antioxidant activity, inflammation, aging, and acts as a cellular control through protein de-acetylation. Without being bound by a particular theory, it is proposed that in HIV infection, NAD+ depletion via tryptophan catabolism as well as CD38 mediated hydrolysis, impairs SIRT-1 function. SIRT-1 negatively regulates NFkB activity via p65 acetylation (Yeung et al., EMBO J. 2004 Jun. 16; 23(12):2369-80) and SIRT-1 activators/agonists suppress TNFα stimulated NFkB activation (Yang et al., PLoS One. 2012; 7(9):e46364) NAD+ deficiency likely contributes to chronic inflammation via the action of TNFα and other inflammatory cytokines. Since NFkB signaling is also involved in survival pathways (Luo et al., J Clin Invest. 2005 October; 115(10):2625-32) the impaired action of Sirtuin-1 could promote the survival of persistently infected and/or latent cellular reservoirs of HIV infection. These effects on the other hand may also contribute to T-cell apoptosis. A balance exists between SIRT-1 and HIV-1 gene transcription and Tat (Zhang et al., J Cell Biochem. 2010 Aug. 15; 110(6):1464-70). Tat can contribute to NAD+ depletion and reduction of SIRT-1 activity (requiring NAD+) by inhibition of Nicotinamide phosphoribosyltransferase (NAMT), the rate-limiting enzyme in NAD+ production (Zhang et al., J Cell Biochem. 2010 Aug. 15; 110(6): 1464-70). By contrast, SIRT-1 is also involved in Tat mediated transactivation of the viral LTR. Tat is acetylated by PCAF and p300 resulting in enhanced recruitment of CDK9/P-TEFb cellular factors required for Tat mediated transactivation of the HIV-1 LTR (Kiernan et al., EMBO J. 1999 Nov. 1; 18(21):6106-18). Indeed, CDK9/P-TEFb can also be regulated by acetylation (Sabo et al., Mol Cell Biol. 2008 April; 28(7):2201-12). Since deacetylation is required for new rounds of HIV transcription, SIRT-1 activity is required for recycling of Tat and continued viral transcription (Blazek and Peterlin, Mol Cell. 2008; 29(5):539-40). NAD+ depletion therefore, in the context of this overall model, would contribute to latency as well as chronic immune activation via inhibition of SIRT-1 regulatory function. Tat can further participate and promote this process via inhibition of nicotinamide phosphoribosyltransferase, NAMT, further inhibiting SIRT-1 and contributing to NAD+ depletion via inhibition of salvage pathway NAD+ synthesis. The majority of HIV genome integrations are not activated by current latency reversing strategies (ie. HDAC inhibitors). Studies suggest HDAC activation is limited to a percentage of competent virus; studies with repeated dosages of vorinostat show diminishing returns over time in vitro and in patients (Archin et al., Nat Rev Microbiol. 2014 November; 12(11):750-64; Archin et al., J Infect Dis. 2014 Sep. 1; 210(5):728-35). Not surprisingly, these integrations reside primarily in transcriptionally active chromatin (Schroder et al., Cell. 2002; 110(4):521-9; Shan et al., J Virol. 2011 June; 85(11):5384-93). In addition to the active versus inactive sites, multiple mechanisms have been proposed, including epigenetic control of transcription factors within cells and at the viral promoter as well as transcriptional interference (Archin et al., Nat Rev Microbiol. 2014 November; 12(11):750-64; Lusic and Giacca, J Mol Biol. 2015 Feb. 13; 427(3):688-94) to explain the resistance of HIV to latency reversing strategies. Without being bound by a particular theory, it is proposed that in areas of active chromatin, and specifically with respect to SIRT-1, a specific agonist, rather than inhibitor/antagonist, will be required to reverse latency. It is proposed that strategies designed to increase NAD+ levels, possibly with additional treatment with SIRT-1 agonists, may be effective alone or in combination with current HDAC strategies.

In the context of the invention presented herein, latency can be reversed by increasing NAD+ levels, using a combined strategy of increasing NAD+ synthesis (salvage pathway precursors) and inhibiting CD38 mediated NAD+ degradation. This approach alone or in combination with SIRT-1 agonists, should permit Tat recycling at the promoter and reversal of latency. It may be necessary to combine this approach, possibly sequentially, with the utilization of more conventional HDAC inhibitors. At the same time, stabilization of NAD+ pools via nicotinamide-ribose supplementation and/or preventing NAD+ breakdown via CD38 inhibition, together should obviate ongoing tryptophan catabolism and IDO induction, restoring immune function.

Without being bound by a particular theory, it is believed that CD38 contributes directly to latency via NAD+ depletion, the consequent inactivation or SIRT-1, and the accumulation of acetylated Tat at the HIV-1 promoter, requiting SIRT-1/NAD+ for reversal of latency.

Experimental Design

Experiments are designed to demonstrate that combination treatments (1) stabilize intracellular NAD+ levels and kynurenine pathways in vitro in HIV/SIV infected PBMCs, (2) reduced inflammatory cytokines and increased SIRT activity in vitro in infected PBMCs, (3) exhibit favorable bioavailability by route of administration and PK data for drug candidates in rhesus macaques treated with cART. modulation of NAD+ metabolism in HIV-1/SIV infected cells is able to restore normal typtophan metabolism, reduce IDO, increase SIRT-1 activity and reverse latency in vitro.

In Vitro Metabolic Studies:

HIV-1 (ADA, Bal) and SIV (SIVmac251, SIVmac239) infected human and macaque peripheral blood mononuclear cells (PBMC), respectively, are treated with NAD+ salvage pathway precursors niacin (nicotinic acid, nicotinamine) or nicotinamine-riboside, CD38 antagonists (quercetin, apigenin, small molecules, and isatuximab), or IDO antagonist (1-methyl Tryptophan). Levels of kynurenine, quinolinic acid and tryptophan are measured by ELISA assay or by LC/MS/MS (Comprehensive NeuroAIDS Center Proteomics Core, Kamel Khalili, Center Director).

The ability of combining salvage pathway precursors and CD38 antagonists alone and in combination to prevent tryptophan catabolism is evaluated. KYN metabolites as well as NAD+ levels in cells and culture supernatants are determined using a NAD/NADH quantification kit (Sigma Aldrich). Endogenous SIRT-1 activity as well as NAD+ stimulation of recombinant SIRT-1 are measured in nuclear extracts from cultured cells using SIRT-1 Fluorimetric Kit (Sigma and Biomol International, LP, Plymouth Meeting, Pa.) using Flour de Lys-SIRT1 substrate. Flow cytometry of immunostained/fixed cells is performed with analysis for monocyte and T cell markers, as well as intracellular IDO staining.

In Vitro Latency Studies:

NAD+ stabilizing strategies including salvage pathway metabolites and CD38 inhibition are evaluated for the potential to serve as a latency reversing agents using latently infected human (HIV-1 ADA and BaL) and macaque (SIVmac251) PBMC. HIV-1 ADA and BaL infection are performed to parallel metabolic studies, above.

Experiments are designed to demonstrate that modulation of NAD+ metabolism in HIV-1/SIV infected cells is able to restore normal typtophan metabolism, reduce IDO, increase SIRT-1 activity and reverse latency ex vivo.

Ex Vivo Metabolic, and Immunologic Studies:

Using plasma, CSF and PBMC from infected (with and without cART) and uninfected rhesus macaques, the levels of tryptophan, KYN metabolites, and NAD+ are determined by methods described above and the effects of HIV infection and cART treatment are evaluated. Similar studies are performed on plasma and PBMC in human adolescents. In rhesus, the expression of IDO is determined in CD4+ T cells (Th1, Th2, Th17) and monocyte subsets (CD14+/CD163+/CD16+/−) in uninfected, SIV infected and cART treated SIV infected macaques in the presence and absence of PHA stimulation. Similar studies are performed using single cell suspensions from lymph node and spleen biopsy specimens to examine IDO expressing cell subsets. For tissues, immunohistochemical studies are performed using additional macrophage markers including CD68, CD206, and CD11c, to identify macrophage suppressor cells and dendritic cells.

Using PBMC from infected, uninfected and SIV infected macaques, the effects of ex vivo drug treatments (i.e. nicotinamide riboside as an NAD+ precursor, and quercetin, apigenin small molecules, and isatuximab as a CD38 inhibitors) are evaluated for the ability to restore normal NAD+, K/T ratios, and SIRT-1 activity in cultures with and without PHA stimulation. Flow cytometry is used to determine the phenotypic effects of treatments as well as intracellular IDO levels.

The ability of combination treatments to enhance SIV specific immune responses is evaluated by Enzyme-Linked Immune Spot assay (ELISpot), T cell proliferation and CD8+ T cell mediated cytotoxicity.

Ex Vivo Latency Studies:

The potential for NAD+ stabilizing strategies including salvage pathway metabolites and CD38 inhibition to serve as a latency reducing strategy are evaluated using PBMC derived from cART treated adolescents and SIVmac251 infected rhesus macaques under treatment with cART PBMC.

Experiments are designed to determine the effects of pharmacologic NAD+ stabilization in vivo, alone and in combination with M2 polarizing agents, to contribute to viral eradication in cART treated SIV infected rhesus macaques.

This study utilizes a well-established model of SIVmac251 infection in rhesus macaques. In order to parallel human studies and provide for the best potential for restoring immunity in the setting of infection, these studies are performed in juvenile rhesus macaques, age 3-5 years of age. In rhesus macaques, females reach puberty at approximately the age of three while males are sexually mature by age four. As a result, in most rhesus studies animals are characterized as adolescent during age 3-5. Within this age bracket, animals are characterized by higher counts (vs. adults) of total lymphocytes and lymphocyte subsets including B-cells, T-cells, CD4+, CD8+ and higher CD4:CD8 ratio. Adolescent animals also exhibit increased frequency of naïve CD4+ and lower memory T-cell populations. Furthermore, adolescent animals demonstrate increased CCR5 on CD4+ T cells (potentially making them more susceptible to SIV infection) and produce reduced cytokine (both pro- and anti-inflammatory) and chemokine levels upon stimulation.

Figure 3:
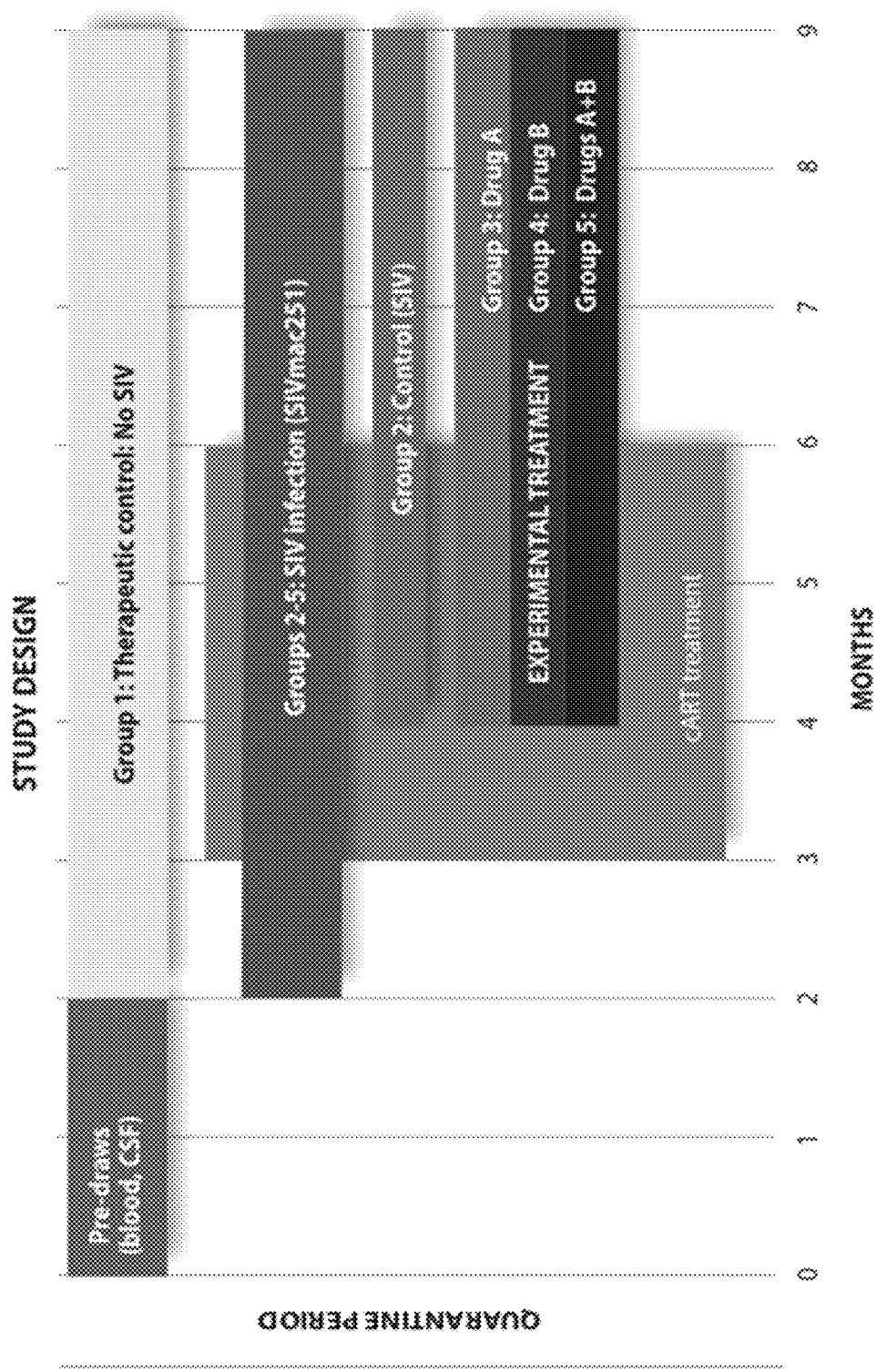
FIG. 3 depicts the Rhesus macaque experimental study design. A 5-group study design is employed to test different drugs, alone and in combination. Group 1, is an uninfected control. Group 2 is infected with SIV. In the initial design for year 1 (pilot study), there will be 15 animals including 3 uninfected and 12 infected animals. After one month of infection, all 12 animals are put on cART treatment for a period of three months. One month after cART initiation, the infected animals are split into 4 sub-groups randomized by viral load pre and post cART, including 3 animals with no additional drug (remaining in group 2), 3 animals with treatment A (Group 3), 3 animals with treatment B (Group 4), and three animals with both treatment A plus treatment B. Treatment A and B, and A plus B, continue for 2 months during cART and 3 months after cART is suspended.

Animal Study Design:

Five groups of animals, with 3 animals/group (subsequent years studies 6/group). Animals are procured for this study based on age 3-5 years (adolescents) and prescreened to eliminate rapid progressor via MHC Class I haplotyping (Sauermann et al., Genes Immun. 2008 January; 9(1):69-80). After a 2-month quarantine period, animals are housed for two months, during which time, three monthly collections for blood (15 ml) and two CSF (0.5 ml) collections (at the start and end of this period) will be performed. Animals are divided into two groups initially, an Uninfected Group (with 3 uninfected animals) and an Infected Group (with 12 animals to be infected by intravenous challenge with a pathogenic stock of SIVmac251)(50 MID50). Prior to beginning the treatment phase of the study (1 months post-infection) infected animals are randomized by viral load into groups 2,3,4, and 5 such that the viral load distribution is similar. Group 2 is a control and does not receive an additional treatment beyond the cART phase of the study. Groups 3, 4, and 5, receive additional treatments developed within this Collaboratory. Groups 3 and 4 are single strategies (i.e. targeting NK-1R/Aprepitant or NAD+ stabilization) and group 5 is a combination of the group 3 and 4 treatments. Experimental compounds are initially administered to the infected animals in a dose escalation format over the week. After 2 months of experimental drug treatment (or 3 months post infection), the cART regimen will be suspended leaving the experimental treatments in place. cART consists of PMPA, FTC, and Raltegravir in all animals. If control cannot be attained adequately, darunavir/ritonivir is added. If this is insufficient, Miraviroc treatment is added. PMPA and FTC are given subcutaneously. All other doses are oral. Doses are as follows: tenofovir (PMPA; 30 mg/kg/day), emtricitabine (FTC; 50 mg/kg/day) and raltegravir (100 mg bid), DRV (375 mg bid) boosted with ritonavir (50 mg bid), maraviroc, (100 mg bid). The animals are followed for immunologic and virologic responses until the end of the study with monthly blood draws and a CSF draw at the end of each segment of the timeline shown in FIG. 3. After three months of cART treatment, cART is interrupted, with groups 3, 4, and 5, continuing treatment with experimental compounds.

NAD+ and Tryptophan Catabolism:

Studies in rhesus macaques measuring KYN metabolites, K/T ratios, NAD+, and endogenous SIRT-1 activity are determined using PBMC extracts and plasma (K/T ratios, NAD+) from animals analyzed at intervals during baseline (pre-infection), 2 weeks, 4 weeks, and monthly intervals, including viral infection, cART treatment, drug+cART, and release from cART/drug alone phases of animal studies described below. Analysis will also be performed using lymphoid tissues, and CSF (K/T ratios, NAD+) collected during each phase of infection and or treatment.

Virologic and Biologic Endpoint Measures:

Control of plasma viremia is considered the primary endpoint, with immunologic control of virus replication suppressing the virus to a lower set point and delaying the return to set point viral load.

Evaluation and Quantitation of Plasma Virus, and Latent Versus Persistent Reservoirs:

Quantitation of virus in plasma and CSF will be performed by a highly sensitive single copy PCR assay capable of detecting single copy/μl of plasma/CSF virus RNA. Additional studies will be performed by quantitation of CD4+ cells containing multiply spliced HIV mRNA with (latent virus) and without (persistent virus) stimulation with PMA plus ionomycin. While it is possible to perform quantitative virus outgrowth assays (qVOA), there is a limitation in feasibility of these assays based on the blood volume of these animals in the macaque model, even with the potential for cell elutriation. For lymphoid tissues (spleen and lymph node biopsies) the persistent reservoir can be defined by performing these assays by flow cytometry on isolated cells without culture and/or stimulation, using flow cytometry based detection of multiply spliced transcripts in combination with T cell and monocyte/macrophage subset markers. Flow based assays are used to normalize HIV RNAs with 18sRNA as well as CD4+ T cell counts should provide effective quantitative measures going forward of latent and persistently infected cells by multicolor flow cytometry using cell suspensions from lymphoid and spleen biopsy material as well as CNS and peripheral tissue specimens and tissue based assays taking advantage of this technology are also employed. For tissue based assays, the frequency of staining for multiply spliced messages is evaluated with the expression of cell-type specific markers identifying CD4+ T cells and macrophages.

Targeting of NAD+ turnover in SIV infected cART treated rhesus macaques normalizes inflammatory markers and kynurenine metabolites, increases SIRT activity, and decreases latent HIV reservoirs.

Treated macaques show increased virologic control, reduced set point, reduced time to return to set point, and increases immune responses, decreases latent and/or persistent HIV reservoirs.

Example 2: Modulation of Tryptophan Degradation Via the Kynurenine Pathway During HIV and SIV Infection The status of monocyte activation appears to play a role in a variety of disease states. It has been previously demonstrated that the non-classical CD16+ (Fc gamma-receptor III) monocyte is increased in frequency in HIV infection, correlating with HIV plasma viremia and inversely with CD4+ T cell count in humans and rhesus macaques with HIV and SIV infection, respectively. This monocyte subset is correlated with the HIV DNA reservoirs, as well as neurocognitive impairment in HIV infection. CD16+ monocytes appear also to be involved in the pathogenesis of cardiovascular disease, kidney disease, obesity, Crohn's disease and rheumatoid arthritis. In vivo, the monocyte subset that expresses CD16 and best correlates with HIV viral load, also expresses CD163, a hemoglobin/haptoglobin receptor. This monocyte subset likely represents a precursor to inflammatory tissue macrophages implicated in these diseases as well as in certain cancers where tumor macrophages expressing CD16 and CD163 appear to play a role in tumor progression. Thus, it is contemplated herein that nicotinamide riboside can be used to treat or prevent HIV associated comorbid conditions, cardiovascular disease, atherosclerosis, renal disease, and CNS disease (with and without infection) as well as autoimmune diseases.

Tryptophan (TRP) is an essential amino acid and precursor for the de novo synthesis of nicotinamide adenine dinucleotide (NAD), as well as serotonin and melatonin, by two different pathways (FIG. 2). TRP is metabolized by the kynurenine pathway (FIG. 2A) to produce NAD and the methoxyindole pathway to generate serotonin and melatonin. Increased kynurenine to tryptophan ratios have been associated with the progression of acquired immune deficiency syndrome (AIDS) as determined by association with lower CD4/CD8 ratios, reduced T cell recovery after initiation or cART, and increased mortality risk. Activation of the kynurenine pathway as well as the neurotoxic metabolite quinolinic acid has been implicated in the pathogenesis of HIV associated neurocognitive disorders (HAND).

As described herein, an increase in the kynurenine to tryptophan ratios in the SIV macaque model was identified, with a positive correlation with viral load and soluble CD163 in plasma. The latter suggests the role of macrophage activation in this process. In an effort to modulate the kynurenine pathway, and decrease tryptophan metabolism, a dose escalation study was performed with the NAD salvage pathway precursor, nicotinamide riboside (NR), in SIV infected macaques. NR treatment significantly reduced the mean fluorescence intensity and percent frequency of CD14+/CD16+ monocytes as determined by flow cytometry, in both SIV infected and uninfected animals. This monocyte subset has been implicated in the pathogenesis of HIV infection, HAND, as well as other HIV associated comorbidities. In uninfected animals NR treatment had no significant impact on the kynurenine to tryptophan ratio relative to pretreatment values. In infected animals, however, NR treatment appeared to increase kynurenine to tryptophan ratio at 100 mg/kg dose, and decrease CD4/CD8 ratio at the highest dose (400 mg/kg). The regulation of the kynurenine pathway appears to be complex, yet an attractive target for HIV therapeutics. Understanding the mechanism by which HIV modulates the kynurenine pathway could provide new therapeutic targets for the treatment of HIV and HAND.

The results of the experiments are now described.

As presented herein, experiments were conducted to investigate tryptophan metabolism as well as the effect of an NAD precursor on the percent frequency of CD16$^+$ monocytes in SIV infected rhesus macaques. It is demonstrated herein that manipulating the kynurenine and NAD salvage pathways/metabolism could provide therapeutic avenues for the treatment of HIV and other inflammatory diseases.

Figures 4A, 4B, 4C:
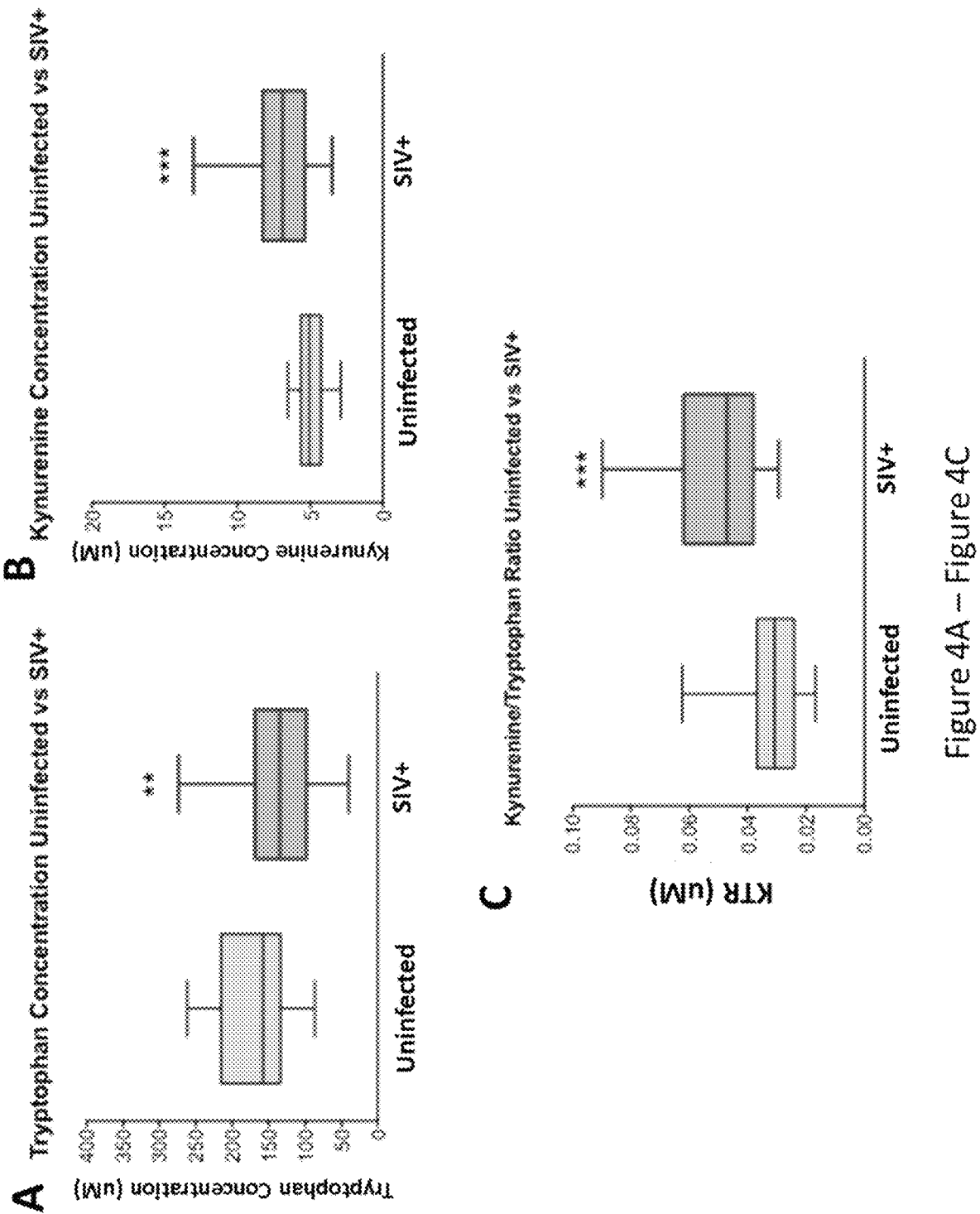
FIG. 4A through FIG. 4C, depicts the results of experiments demonstrating that $SIV^+$ macaques exhibit elevated Kyn and Trp (K/T) ratios.

Experiments were first conducted to examine the kynurenine to tryptophan ratio in SIV+ macaques. kynurenine to tryptophan ratio for uninfected and SIV infected macaques were calculated based on plasma concentrations of kynurenine and tryptophan, analyzing data across 3 time points, with 5 seronegatives and 10 SIV infected animals. The results indicate a decrease in Tryptophan concentration and an increase in Kynurenine concentration in SIV positive animals when compared to uninfected controls (FIG. 4A-FIG. 4B). Further, an increase in kynurenine to tryptophan ratio in animals infected with SIV when compared to uninfected controls was observed (FIG. 4C). Together, this data demonstrates that SIV+ macaques exhibit elevated kynurenine to tryptophan ratios.

Figures 5A, 5B, 5C:
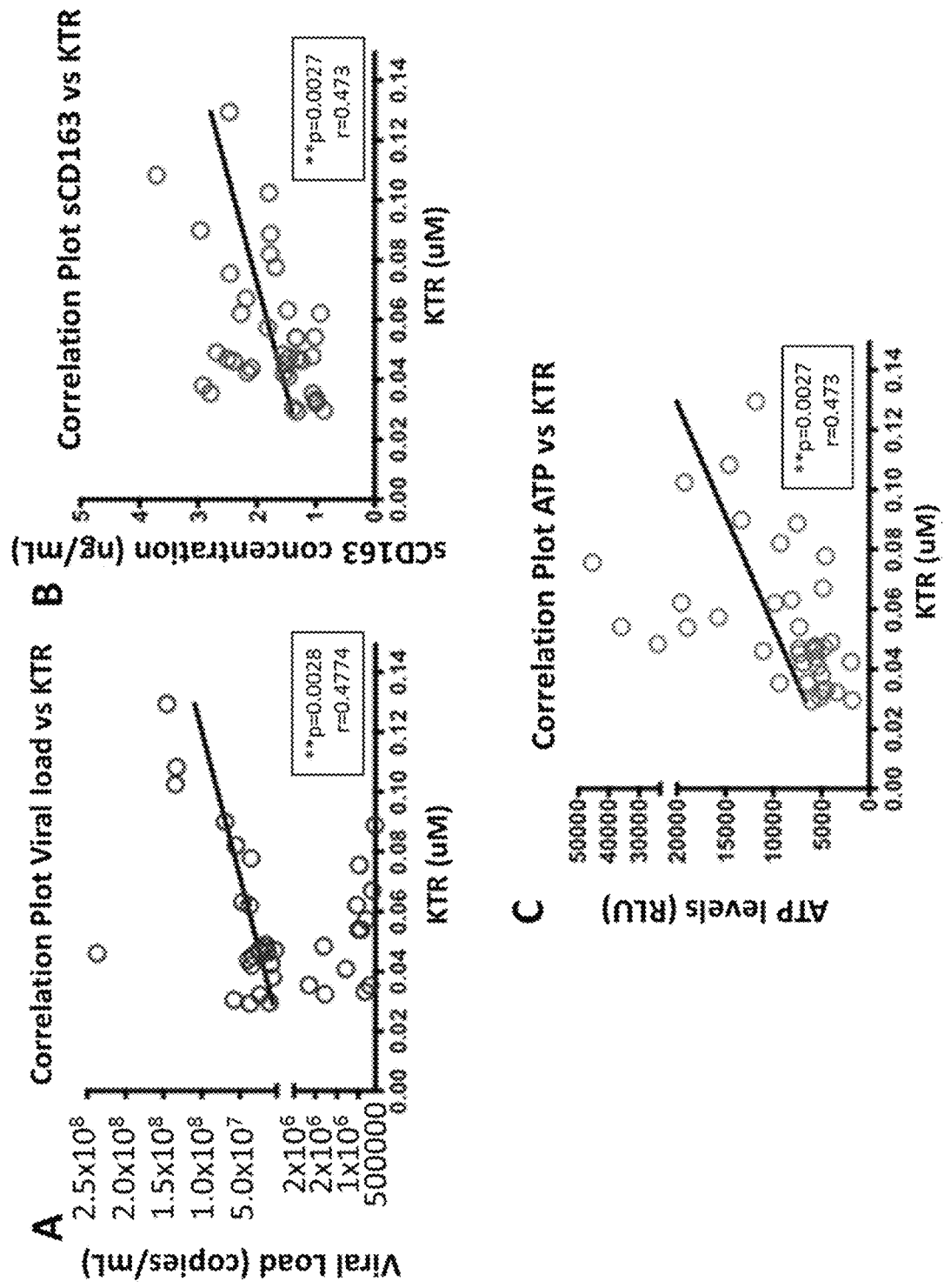
FIG. 5A through FIG. 5C, depicts the results of experiments demonstrating that kynurenine to tryptophan ratios of SIV infected macaques positively correlate with sCD163 plasma levels, ATP plasma levels and viral loads. ELISA kits were used according to the manufactures' directions to determine plasma concentrations of sCD163, kynurenine and tryptophan. Plasma ATP levels were analyzed using ATPLite assay.

Experiments were then conducted to examine if kynurenine to tryptophan ratios of SIV infected macaques correlate with sCD163 plasma level, ATP plasma level, and viral load. ELISA kits were used according to the manufacturer's directions to determine plasma concentrations of sCD163, kynurenine and tryptophan. Plasma ATP levels were analyzed using ATPLite assay. It was determined that kynurenine to tryptophan ratios increased in relations to higher viral loads (r=0.4774; p=0.0028) (FIG. 5A). Further, a positive correlation between kynurenine to tryptophan ratio and sCD163 plasma concentration was observed (r=0.473; p=0.0027) (FIG. 5B). Further, kynurenine to tryptophan ratios also exhibited a positive correlation with plasma ATP levels (r=0.3514; p=0.0305) (FIG. 5C). Together, this data demonstrates that kynurenine to tryptophan ratios of SIV infected macaques positively correlate with sCD163 plasma levels, ATP plasma levels and viral loads.

Figures 6A, 6B, 6C, 6D:
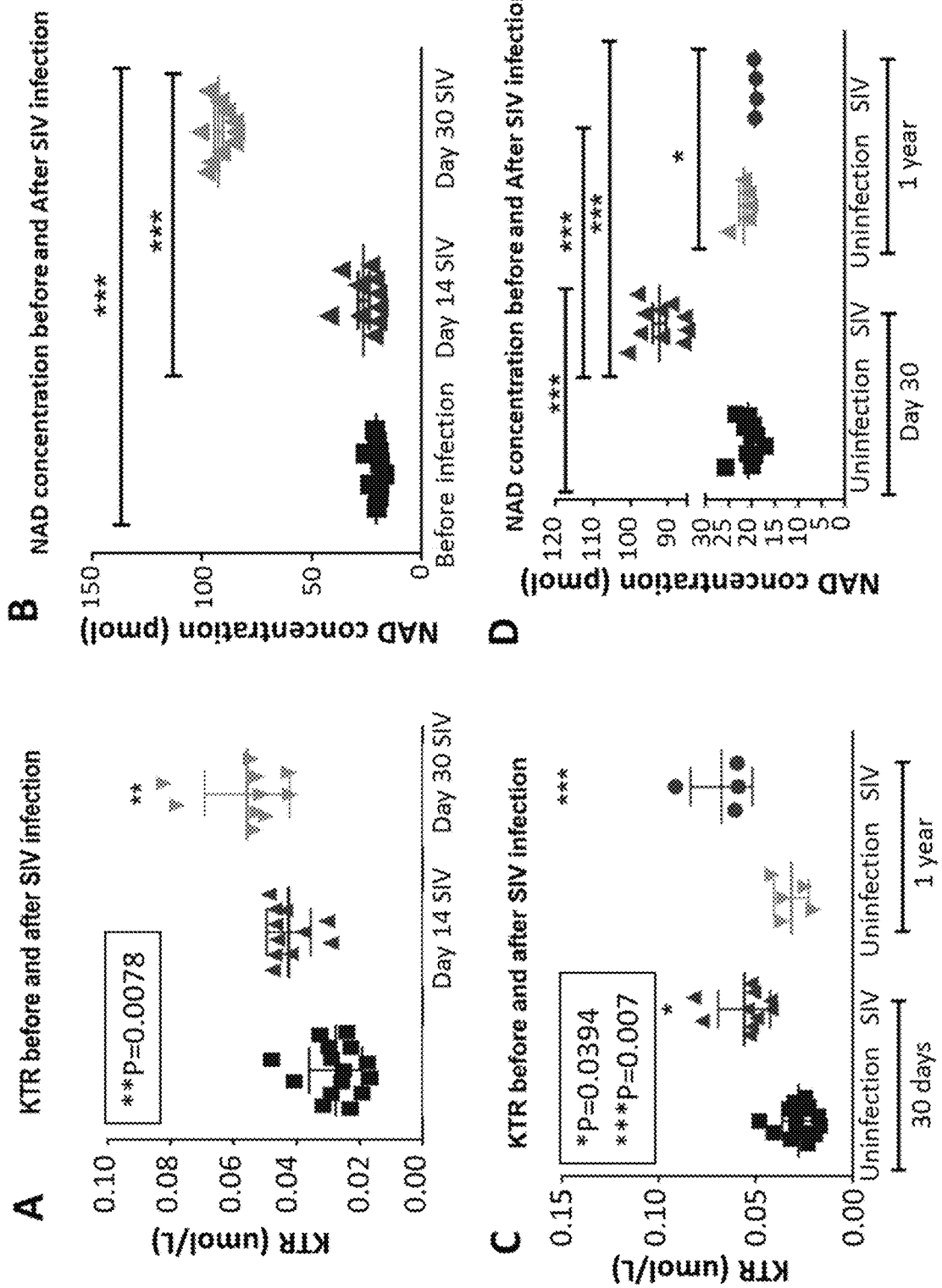
FIG. 6A through FIG. 6D, depicts data demonstrating the effects of SIV infection on NAD and kynurenine to tryptophan ratio (KTR), early during SIV infection.

Evaluation of the kynurenine to tryptophan ratios and NAD concentration over time showed a significant increase in both 30 days after SIV infection (FIG. 6A and FIG. 6B). However, 1 year after infection NAD concentration had decreased, but the kynurenine to tryptophan ratio remained elevated (FIG. 6C and FIG. 6D).

Figure 7A:
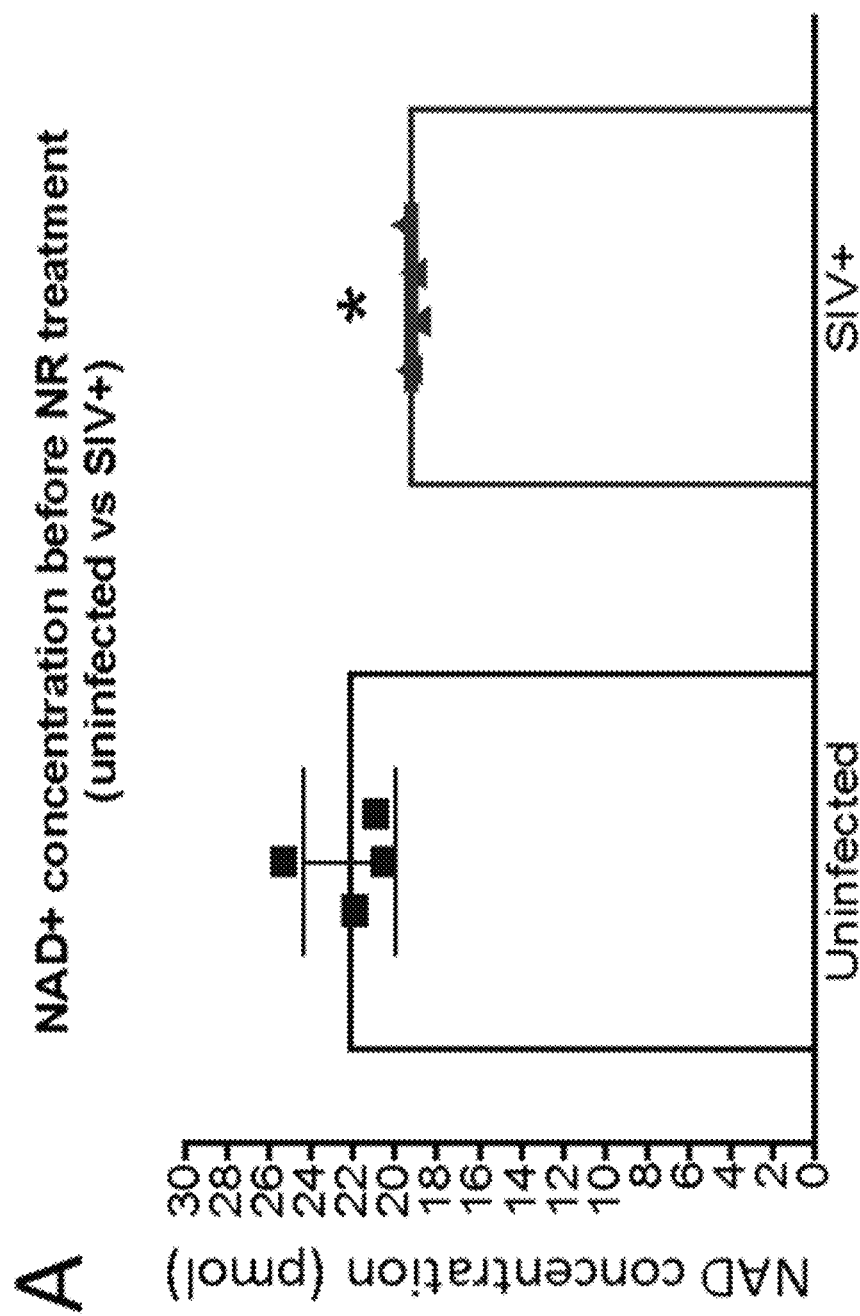
FIG. 7A through FIG. 7C, depicts the results of experiments demonstrating that nicotinamide riboside treatment increases NAD+ levels in SIV infected animals. Peripheral blood mononuclear cells (PBMC) from five seronegative and four seropositive rhesus macaques were lysed and assayed for NAD+ concentration after treatment with increasing concentrations of nicotinamide riboside (NR) over a 5 week period.
Figure 7B:
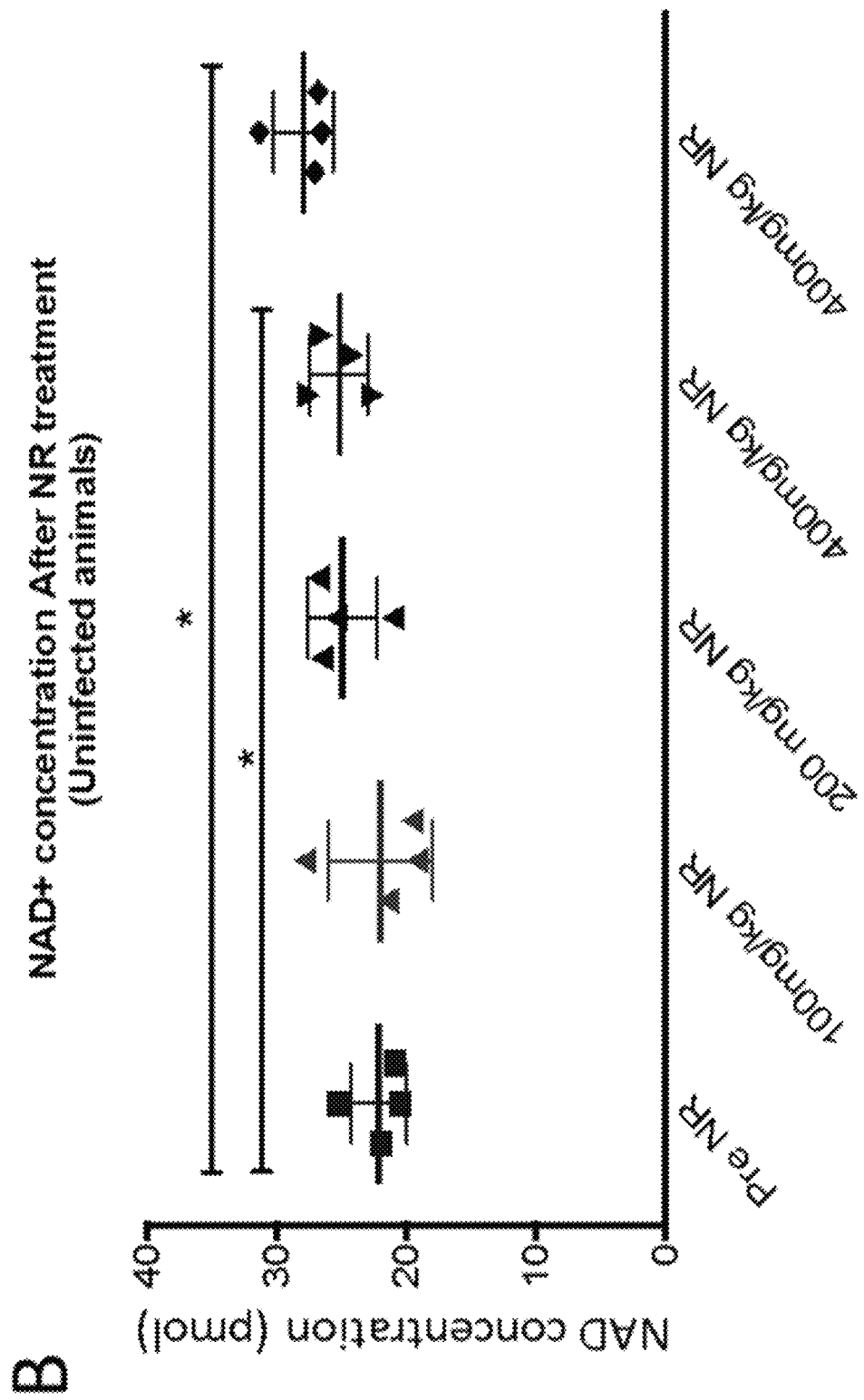
Figure 7C:
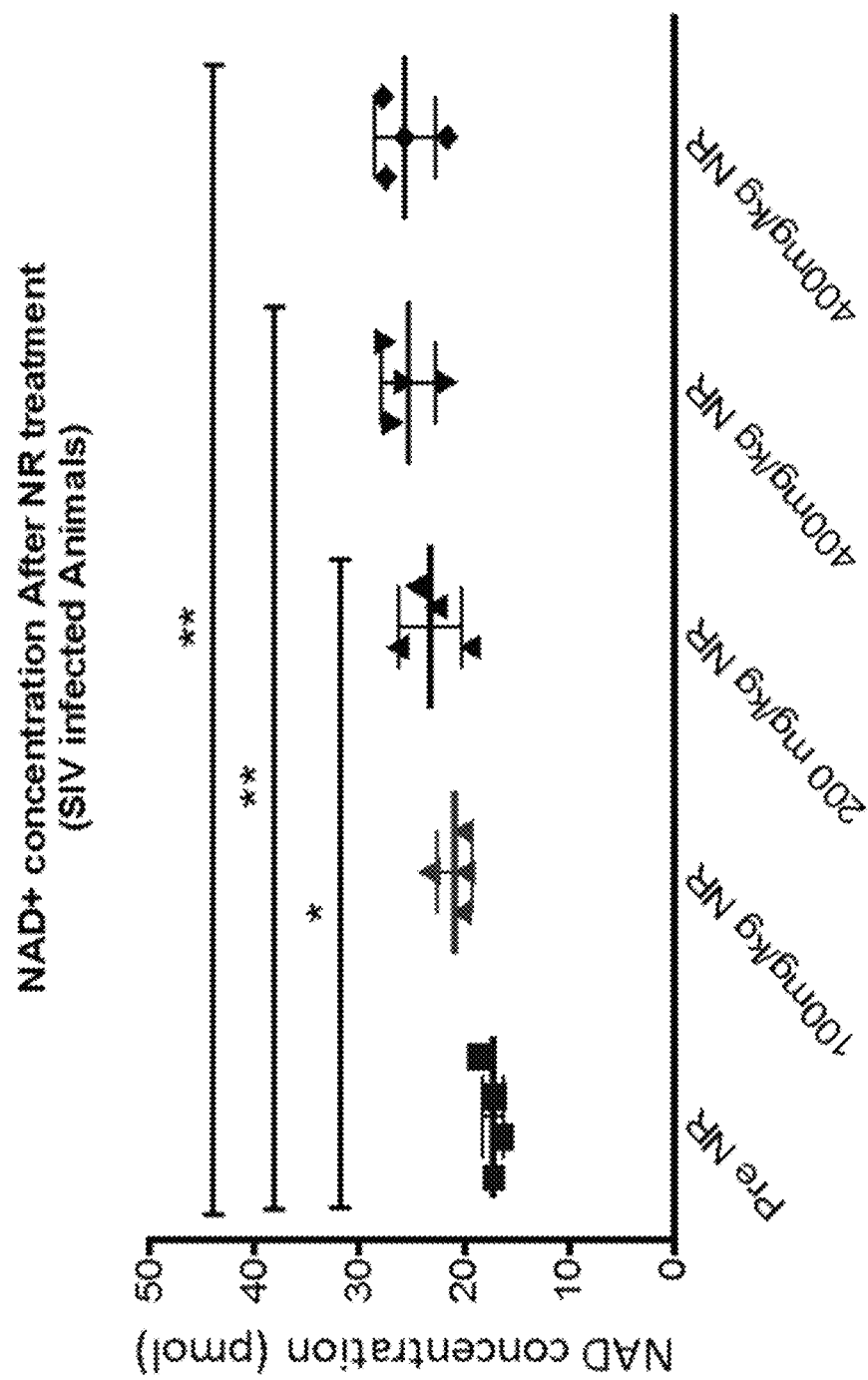

Experiments were then conducted to examine the effect of nicotinamide riboside treatment on NAD+ levels in SIV infected animals. Peripheral blood mononuclear cells (PBMC) from five seronegative and four seropositive rhesus macaques were lysed and assayed for NAD+ concentration after treatment with increasing concentrations of nicotinamide riboside (NR) over a 5 week period. NAD+ concentrations before NR treatment demonstrate significantly lower NAD+ concentrations in SIV infected macaques (FIG. 7A). Treatment with NR significantly increased NAD+ concentration in both uninfected (FIG. 7B) and SIV infected rhesus macaques (FIG. 7C).

Figure 8A:
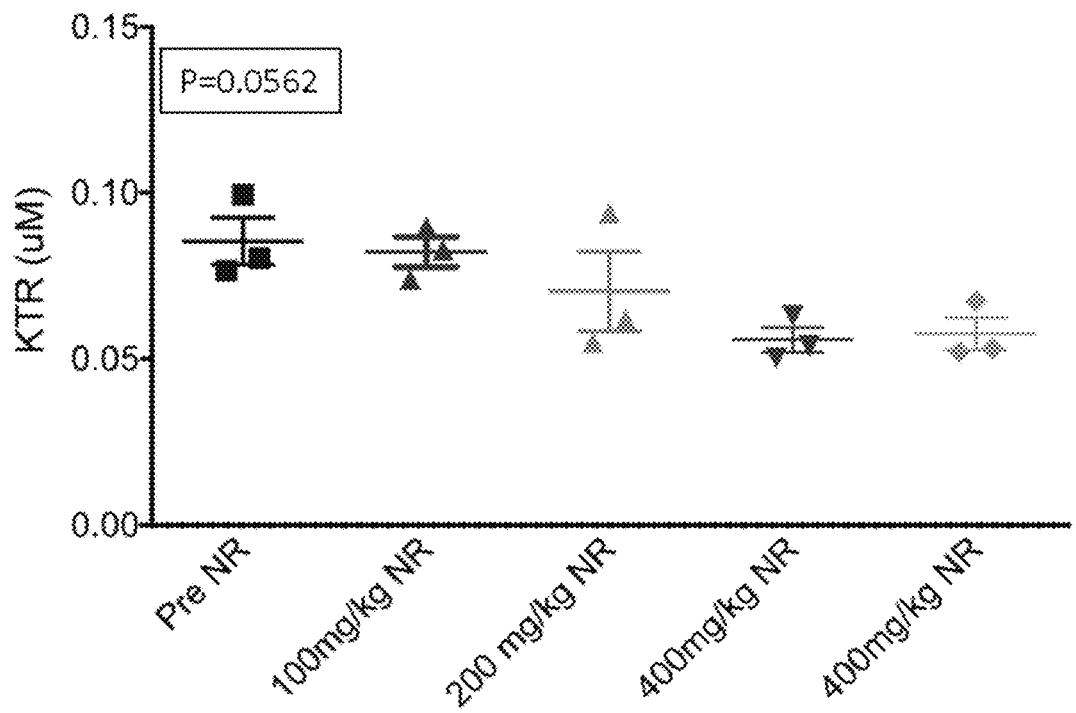
FIG. 8A and FIG. 8B, depicts experimental results demonstrating that NR treatment decreases KTR in SIV but not seronegatives in vivo.
Figure 8B:
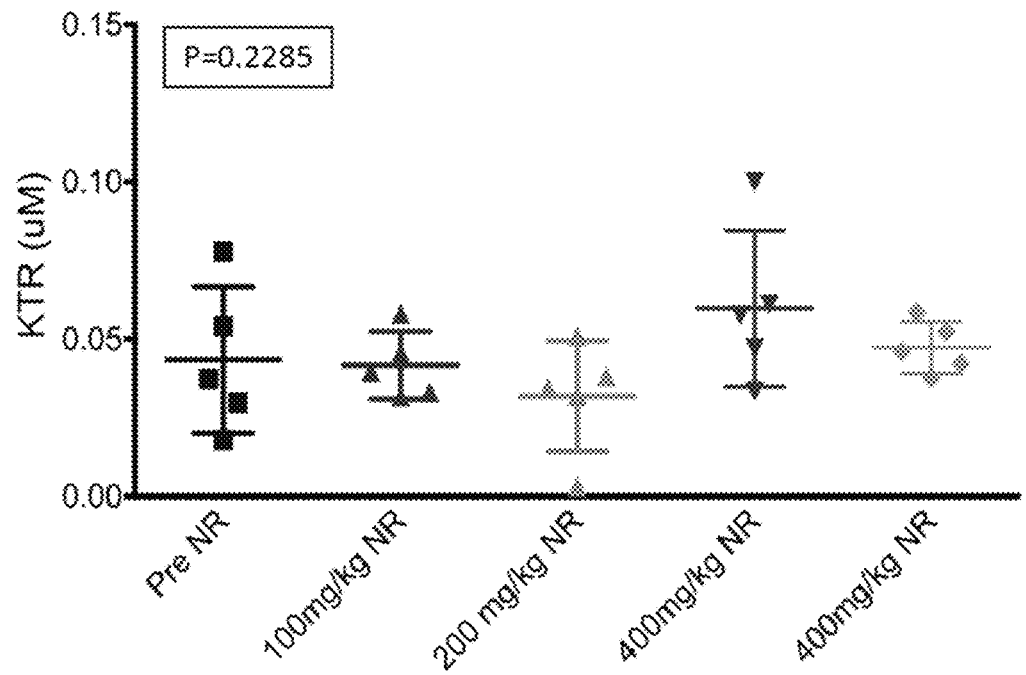

FIG. 8 demonstrates that the kynurenine to tryptophan ratios of SIV infected animals decreased in response to NR treatment, however the same was not seen for untreated animals. Together this data demonstrates that nicotinamide riboside treatment both increases NAD+ levels and decreases the kynurenine to tryptophan ratios in SIV infected animals.

Figure 9A:
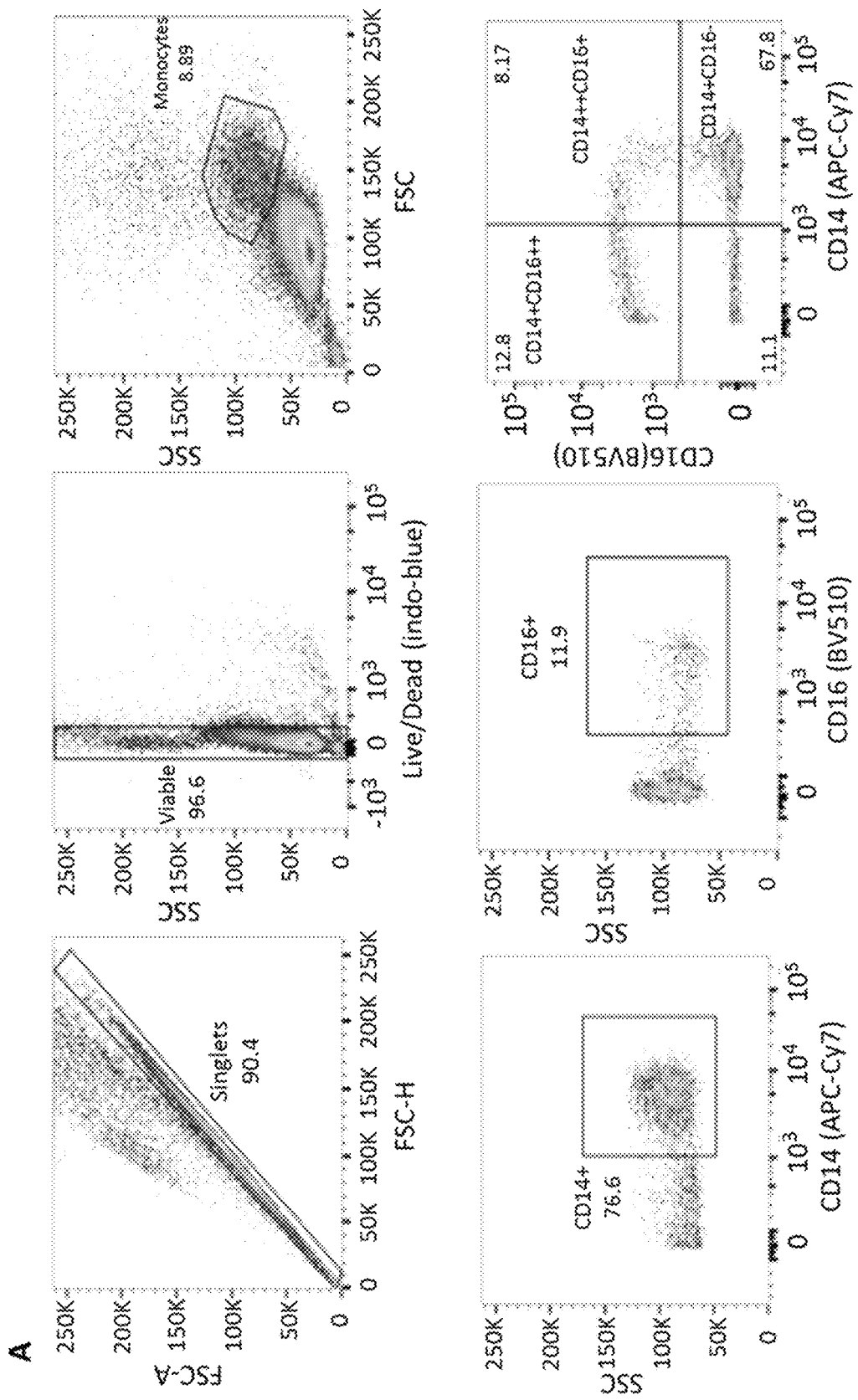
FIG. 9A and FIG. 9B, depicts the results of experiments demonstrating that nicotinamide riboside treatment significantly decreases CD16 expression on CD14+ Monocytes. PBMC from five seronegative and four seropositive rhesus macaques were analyzed after treatment with increasing concentrations of nicotinamide riboside (NR) over a 5-week period. Fluorescence-activated cell sorting data represented as dot plots demonstrate the monocyte populations present before NR treatment and following NR treatment.
Figure 9B:
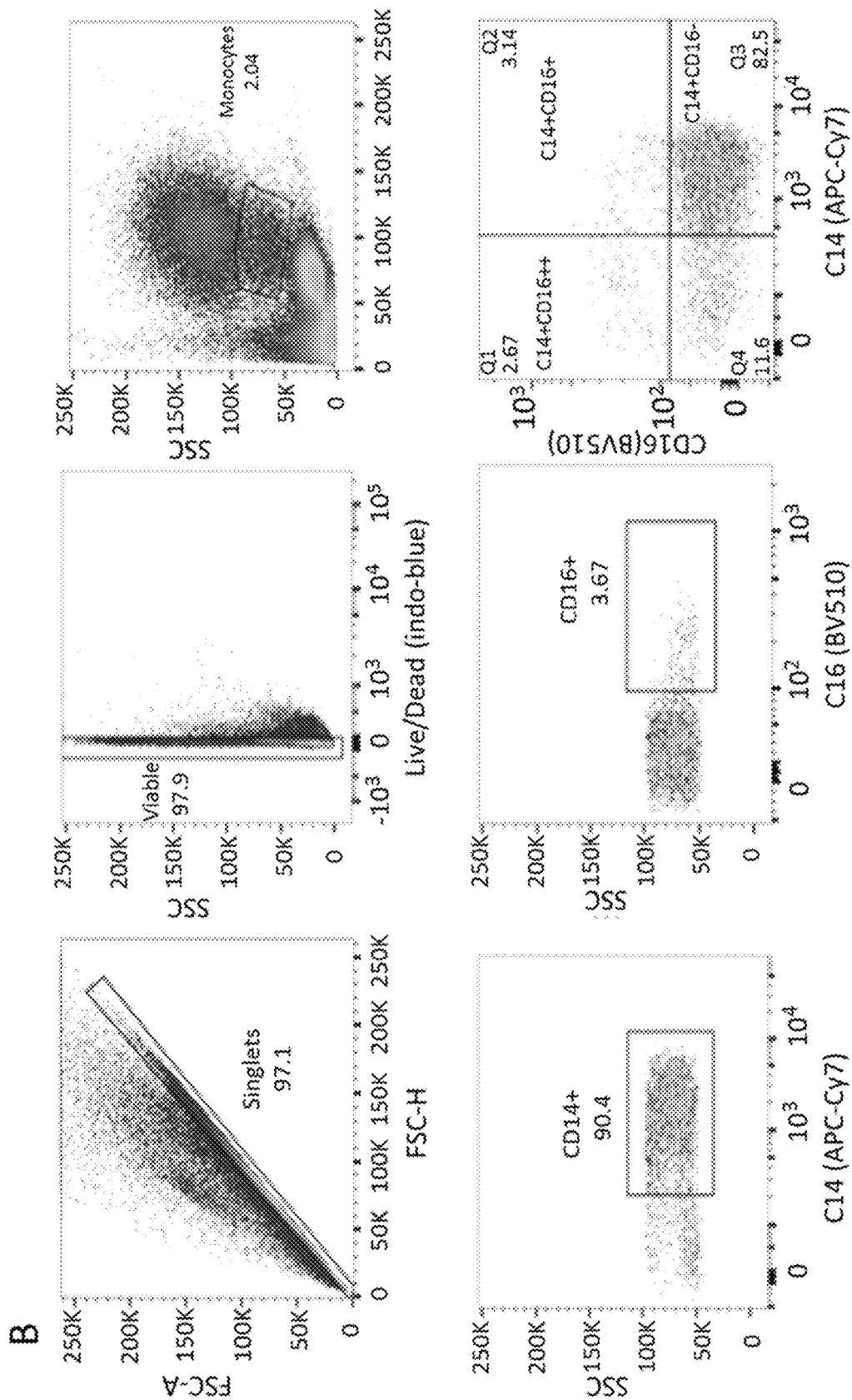

Experiments were then conducted to examine whether nicotinamide riboside treatment effects CD16 expression on CD14+ monocytes. PBMC from five seronegative and four seropositive rhesus macaques were analyzed after treatment with increasing concentrations of nicotinamide riboside (NR) over a 5-week period. Fluorescence-activated cell sorting data represented as dot plots demonstrate the monocyte populations present before NR treatment and following NR treatment. Prior to treatment with NR monocyte populations demonstrate normal CD16 expression (FIG. 9A). After treatment with NR CD16 expression decreased in all animals examined (FIG. 9B). Together, this data demonstrates that nicotinamide riboside treatment significantly decreases CD16 expression on CD14+ monocytes.

Figure 10A:
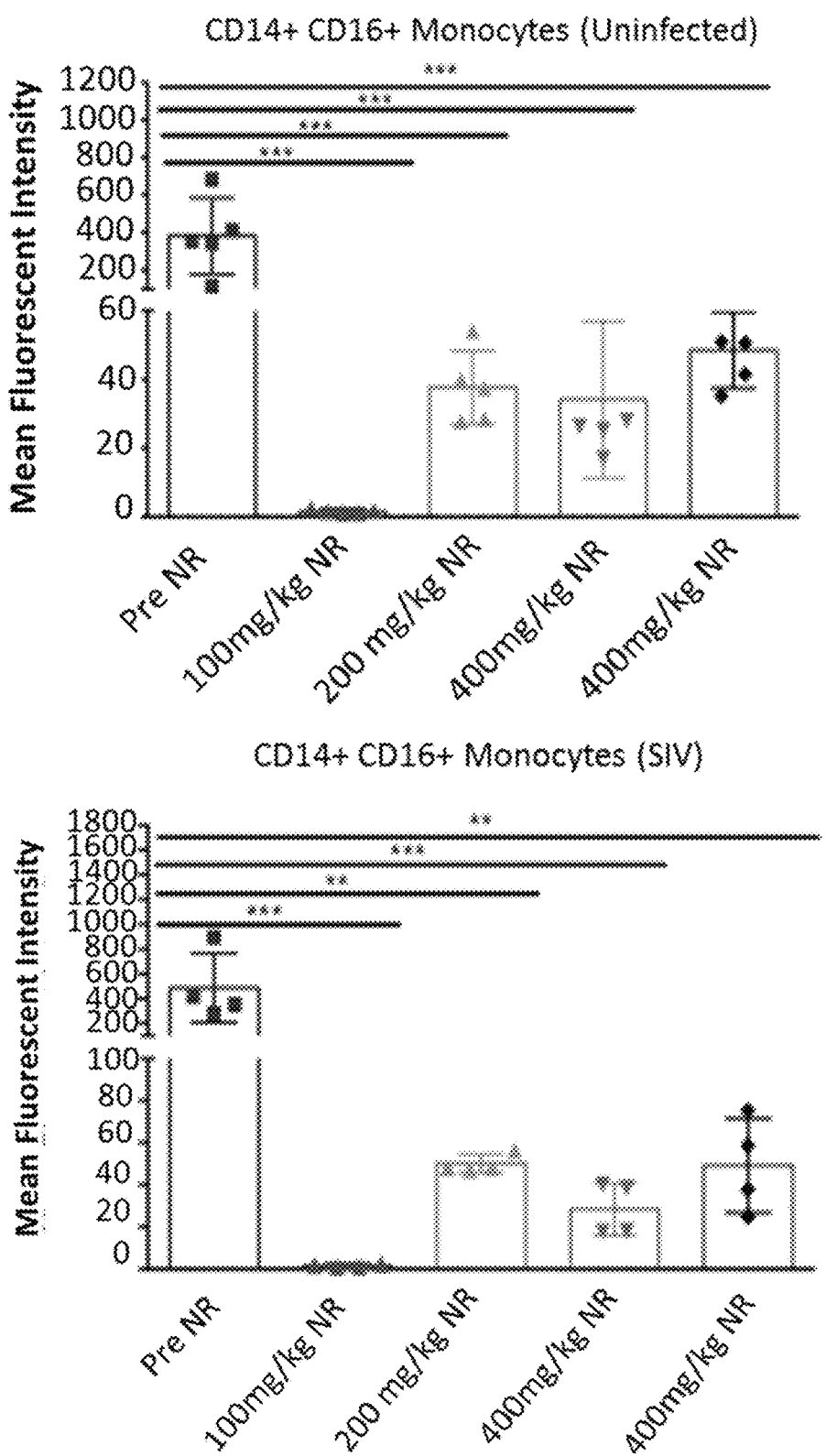
FIG. 10A and FIG. 10B, depicts the results of experiments demonstrating that NR treatment significantly reduced the mean fluorescence intensity and percent frequency of CD14+/CD16+ monocytes. PBMC from five seronegative and four seropositive rhesus macaques were stained with antibodies to CD14 and CD16 and analyzed by flow cytometry after treatment with increasing concentrations of NR over a 5-week period. The mean fluorescence intensity (MFI) and percent frequency (% Freq) of CD16 was determined for each animal.
Figure 10B:
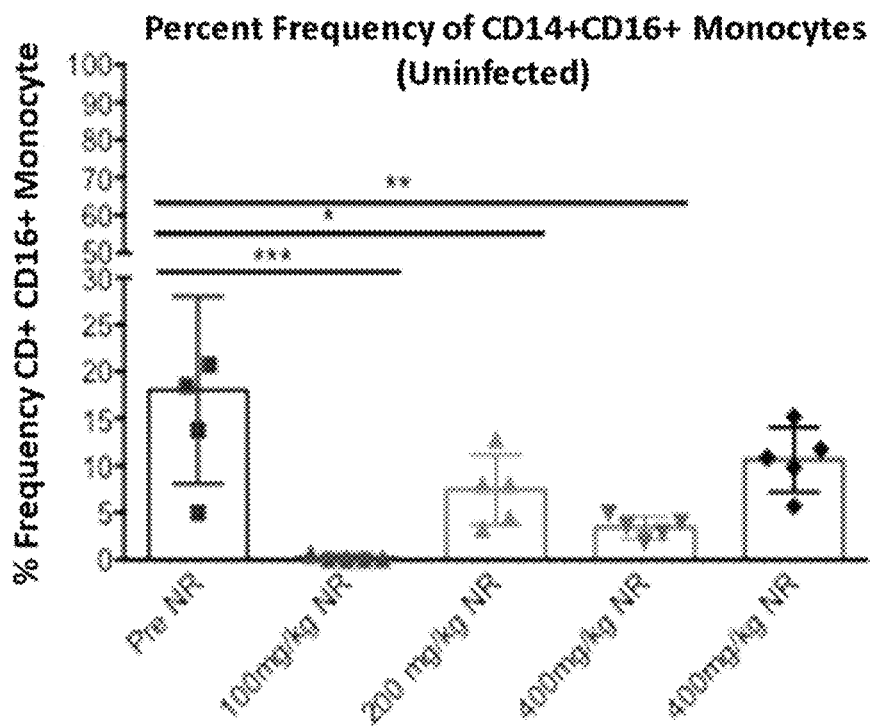
Figure 10B:
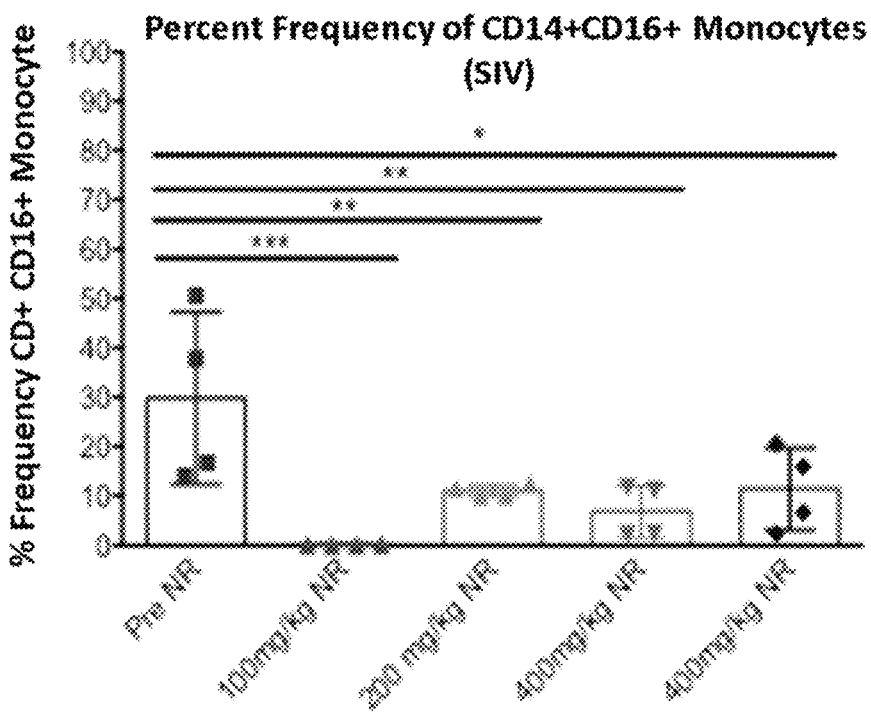

Experiments were then conducted to examine the effects of NR treatment on CD14 and CD16 expression. PBMC from five seronegative and four seropositive rhesus macaques were stained with antibodies to CD14 and CD16 and analyzed by flow cytometry after treatment with increasing concentrations of NR over a 5-week period. The mean fluorescence intensity (MFI) and percent frequency (% Freq) of CD16 was determined for each animal. CD16 MFI before NR treatment was significantly higher than after treatment in all animals (FIG. 10A). Percent frequency of CD16 was significantly decreased after treatment with NR in uninfected and SIV infected macaques (FIG. 10B). Together this data demonstrates that NR treatment significantly reduced the mean fluorescence intensity and percent frequency of CD14+/CD16+ monocytes.

Figure 11:
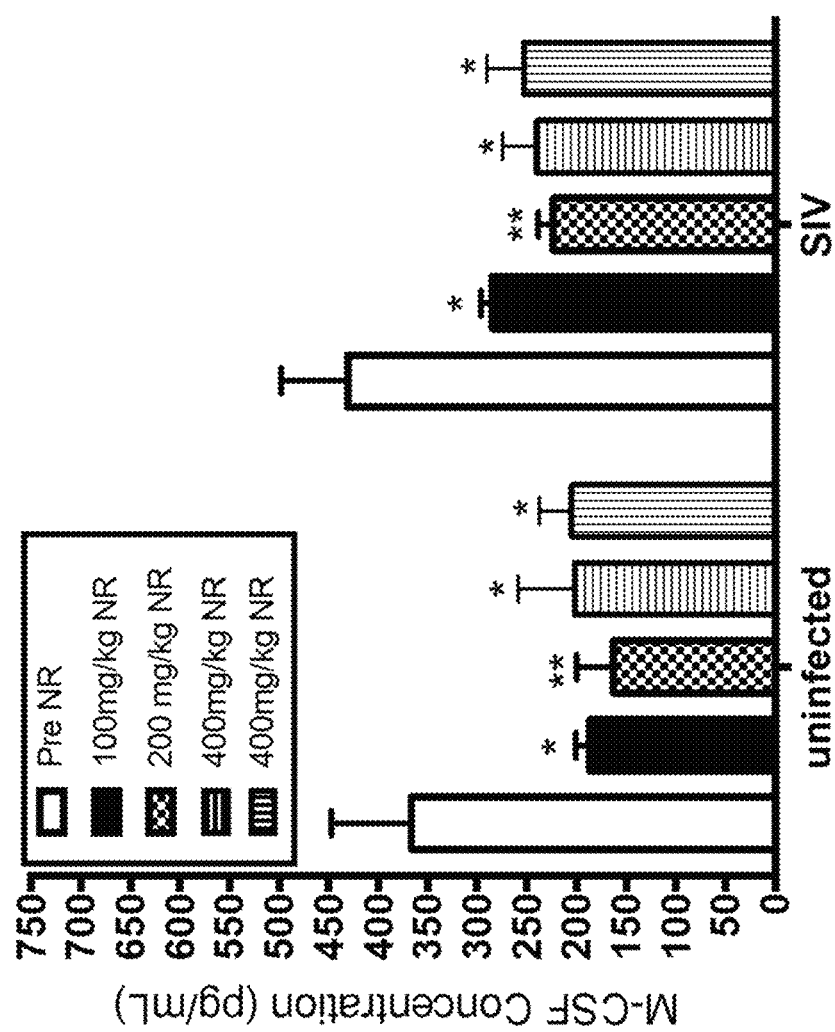
FIG. 11 depicts experimental results showing that macrophage colony-stimulating factor (M-CSF) is reduced in NR treated macaques.
Figure 12:
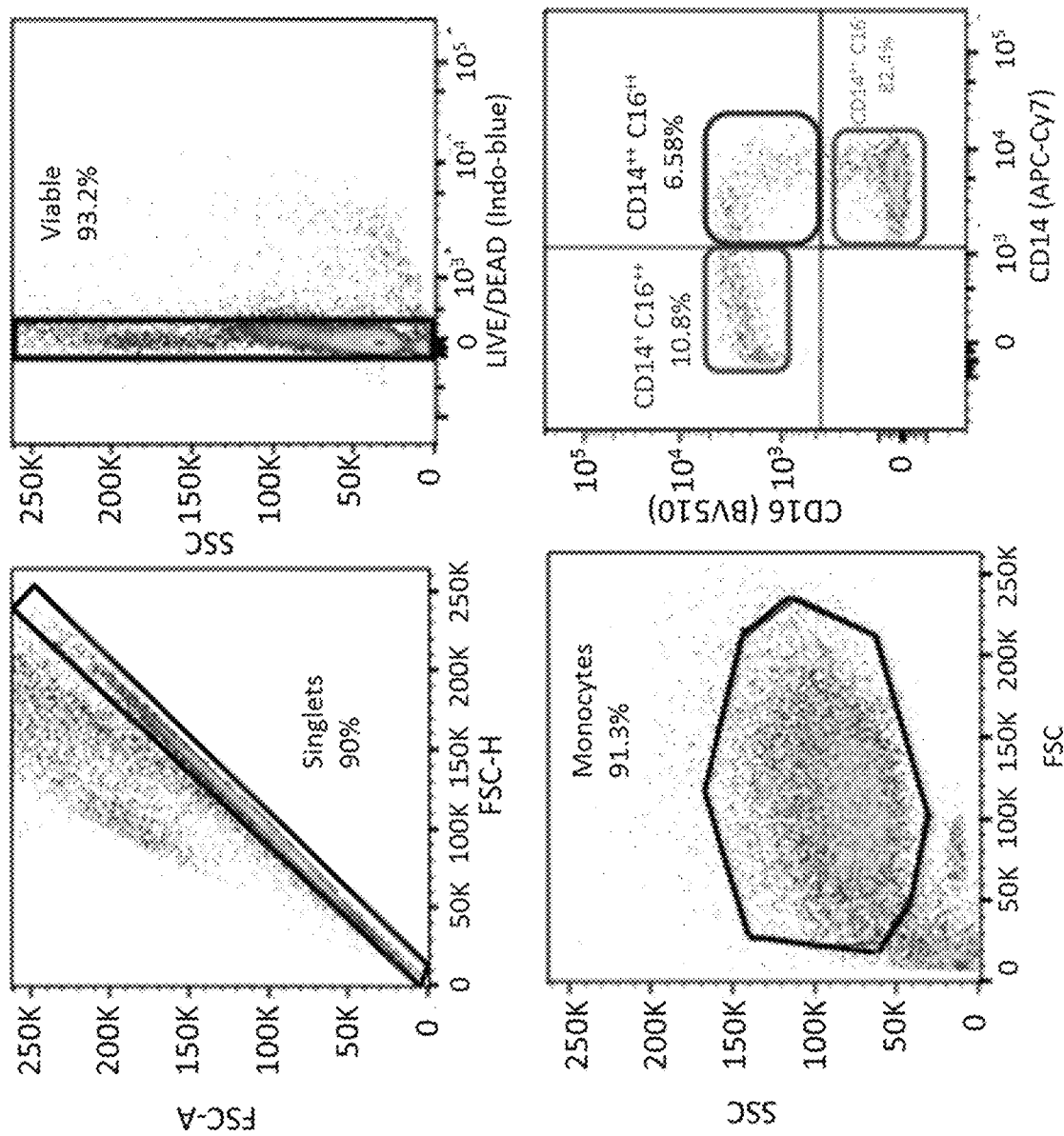
FIG. 12 depicts the flow cytometry gating strategy used to separate two CD16 positive monocyte subsets.
Figure 13:
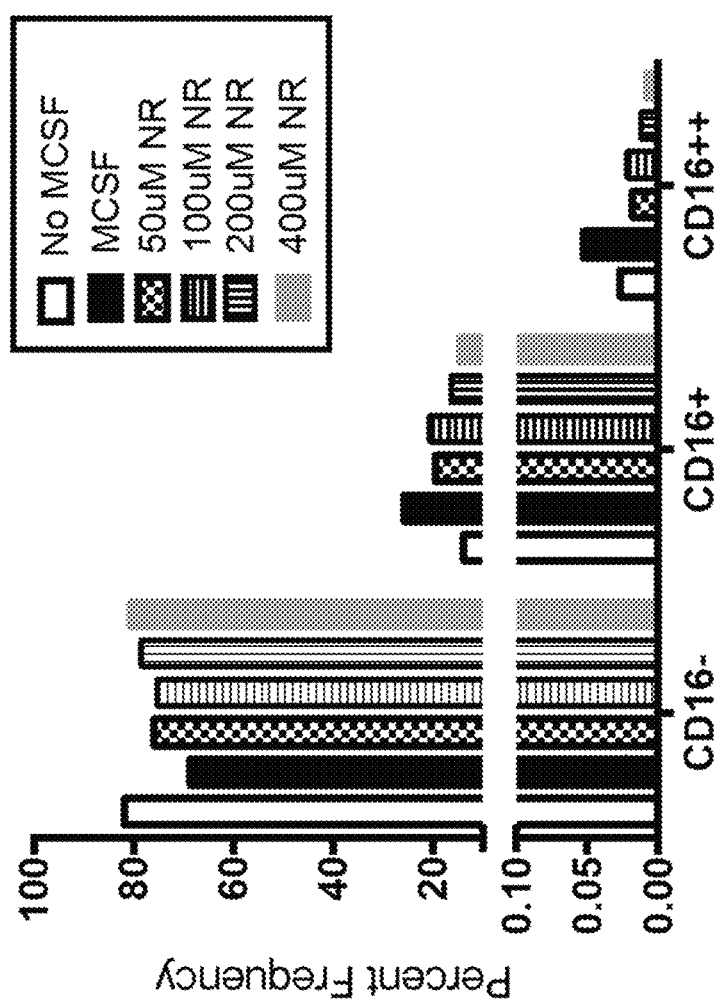
FIG. 13 depicts experimental results demonstrating that NR treatment reduces CD16 monocyte subset expression in human monocytes isolated from donor PBMCs in the presence of M-CSF treatment.
Figure 14:
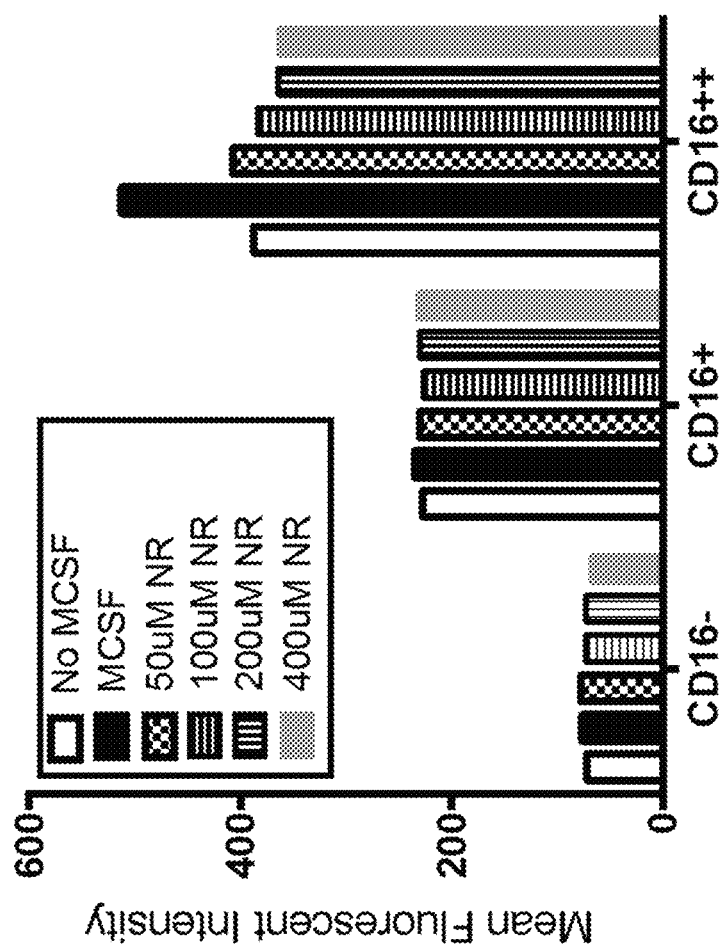
FIG. 14 depicts the mean fluorescent intensity for CD16 expression in human monocytes isolated from donor PBMCs in the presence of M-CSF treatment.

FIG. 11 demonstrates that NR reduces M-CSF, which is known to activate CD16 monocyte subsets in vivo, which are implicated in CNS and cardiovascular disease. This effect can be modeled in vitro using monocytes isolated from human donors, where NR inhibits CD16 monocyte expression induced by M-CSF (FIG. 12 through FIG. 14).

Figure 15:
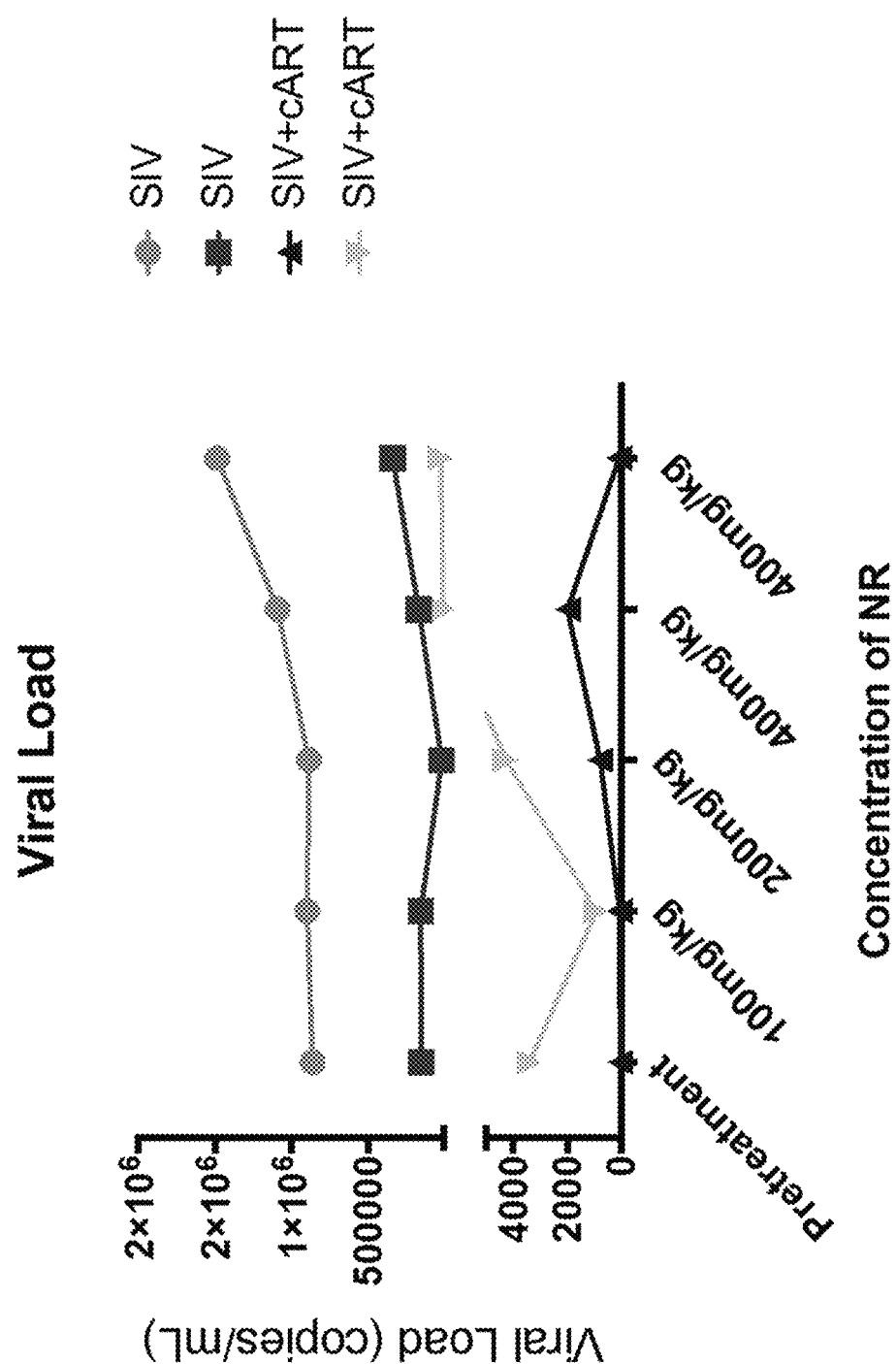
FIG. 15 depicts experimental results showing that NR may function as a latency reversing agent for SIV infection. Four SIV infected macaques were followed over time during chronic infection, two treated with combination anti-retroviral therapy (cART), and two non-treated. All 4 were treated with NR and effects on viral load are shown. While there is evidence for viral load increase in all animals, the animal on cART with the lowest viral showed an increase in viral load and then decrease over time. Such a pattern would be desirable for a latency reversing agent treatment during fully suppressed antiretroviral therapy.

FIG. 15 demonstrates the potential for NR to function as a latency reversing agent in rhesus macaques infected with SIV.

The experiments presented herein demonstrate that during SIV infection Tryptophan levels decrease and Kynurenine levels increase when compared to uninfected controls. Further, it was demonstrated that kynurenine to tryptophan ratios increase in SIV infected macaques. It is also shown that there is a positive correlation between kynurenine to tryptophan ratio and elevated viral load, sCD163 and ATP. Finally, it was demonstrated that NR treatment given to rhesus macaques significantly decreases the mean fluorescent intensity and percent frequency of CD14+CD16+ monocytes. Together this data demonstrates that NR treatment can be used to treat HIV infection and related comorbidities.

Example 3: Treatment of HIV Associated Atherosclerosis

HIV infected individuals are an aging population, and since the introduction of combination anti-retroviral therapy (cART) the lifespan has increased several decades. There are currently more than 35 million individuals living with HIV world wide and 10% of this population is estimated to be over the age of 50%, however in regions with higher income this percentage can be as high as 33%. With the introduction of cART less patients are now dying from AIDS and it has decreased from 94% to 47%.

Cardiovascular disease (CVD) is the second leading cause of death in this population. HIV-1 infection is associated with a two to four fold higher incidence in CVD which includes, stroke, myocardial infarction and sudden cardiac death. And after correcting for traditional risk factors HIV-1 infection alone is associated with a 50% increased risk of myocardial infarction (MI). however in HIV-1 infected individuals treated on cART there is an increase in hypertension, diabetes and renal dysfunction and dyslipidemia which are all know causes of atherosclerosis and lead to CVD being an even bigger problem in this population.

Atherosclerosis is a driving force in CVD and is the focus of this study. Stroke, MI and sudden cardiac death are all well-known complications of atherosclerosis and, in patients with HIV, there are increased clinical findings of atherosclerosis. Development of the advanced plaques from atherosclerosis may lead to stroke from plaque rupture, MI from occlusion and/or thrombus formation.

Carotid, femoral, or iliac intima-media thickness are constantly greater and progress earlier among the HIV-positive population (Periard, et al. Clin Infect Dis. 2008 Mar. 1; 46(5):761-7). Carotid artery thickening was up to 24% higher in HIV-1 infected patients with both cART treatment and cART naivety. Even patients with tightly controlled viremia on cART have more subclinical coronary atherosclerosis. HIV elite controllers have degrees of atherosclerosis that are similar, if not greater than that of chronic HIV-1 infection receiving long-term cART (Pereyra et al.

AIDS. 2012 Nov. 28; 26(18):2409-12). HIV infection is associated with an increase in systemic inflammation and damage to the vascular endothelium. Inflammatory plaques are more likely to rupture. An increase in IL-6 levels has been associated with an increase in cardiovascular mortality in HIV-infected individuals. These increased signs of atherosclerosis can be due to an increase in risk factors.

Not only are HIV patients susceptible to traditional risk factors (e.g. age, male gender, greater body mass index, family history, smoking), but additional HIV specific factors as well such as increased HIV-1 latency in infected T-cell and macrophage reservoirs after cART treatment, lipodystrophy syndrome, co-infection with hepatitis C, metabolic syndrome, end-stage renal disease, and antiretroviral therapy.

In determining the mechanism for HIV associated atherosclerosis it is important to know the pathogenesis of atherosclerosis. The current understanding of the pathogenesis in HIV infected individuals is limited to human observational studies or in vitro studies, due in part to a lack of animal models for HIV-1 associated atherosclerosis. A better understanding the mechanism can help in finding therapeutic targets for HIV-1 associated comorbidities.

The current Human Clinical evidence strongly indicates immune activation and inflammation as a driving force. Such evidence includes (1) soluble CD163, a novel marker of activated macrophages, is elevated and associated with noncalcified coronary plaque in HIV-infected patients (Burdo et al. J Infect Dis. 2011 Oct. 15; 204(8):1227-36); (2) T cell activation and senescence predict subclinical carotid artery disease in HIV-infected women (Kaplan et al. 2011); (3) coronary atherosclerosis and immune activation are increased in HIV-1 elite controllers (Pereyra et al. AIDS. 2012 Nov. 28; 26(18):2409-12); (4) oxidized LDL levels are increased in HIV infection and may drive monocyte activation (Zidar et al., J Acquir Immune Defic Syndr. 2015 Jun. 1; 69(2): 154-60); and (5) elevated levels of monocyte activation markers are associated with subclinical atherosclerosis in men with and those without HIV infection (McKibben et al. J Infect Dis. 2015 Apr. 15; 211(8):1219-28).

Studies conducted to investigate HIV-1 mediated atherosclerosis have revealed that (1) HIV-derived ssRNA binds to TLR8 to induce inflammation-driven macrophage foam cell formation (Bernard et al. PLoS One. 2014 Aug. 4; 9(8): e104039); (2) monocytes from HIV-infected individuals show impaired cholesterol efflux and increased foam cell formation after transendothelial migration (Maisa et al., AIDS. 2015 Jul. 31; 29(12):1445-57); and (3) HIV protein Nef causes dyslipidemia and formation of foam cells in mouse models of atherosclerosis (Cui et al., FASEB J. 2014 July; 28(7):2828-39).

A mouse model system has now been developed. This is a model system without HIV replication, despite the integration of HIV provirus into all cells. This may be a useful model to determine the effects of HIV infection, when the virus is fully suppressed, but not eradicated as in a latent and/or persistent infection, fully suppressed under antiretroviral therapy.

This is the first model of HIV infection in mice that can be used to model cardiovascular diseases, which can be used to interrogate and treat the contribution of HIV as well as HIV-1-associated co-morbidities such as cardiovascular diseases and vascular dementia. There are other models of cardiovascular diseases and atherosclerosis in several species, including rabbits, pigs, mice, and non-human primates. There are publications which show the alterations of the kynurenine pathway in HIV/SIV infection, and under antiretroviral treatment. This model demonstrates altered KTR in the absence of antiretroviral therapy and in the total absence of virus replication. This model can be used to test targets such as CD38, NAD+ precursors, IDO antagonists, as well as other targets for treatment of HIV-1-associated co-morbidities such as atherosclerosis/CVD and vascular dementia in the setting of HIV infection.

In this study the animal model is used to test targets involving the kynurenine pathway, IDO, CD38, NAD+ precursors, and activation of Sirtuin 1 as well as other novel cellular and molecular mechanisms underlying HIV-1-associated cardiovascular diseases and vascular dementia. This model may also be used to determine the role of increasing NAD+ and Sirtuin agonists to function as latency reversing agents by determining the activation of HIV gene expression in various mouse tissues upon treatment with various compounds. Probably measurement of K/T ratio would be an indication of the effectiveness of therapy that can be demonstrated in this model. Soluble CD163 (sCD163) is a marker for cardiovascular disease in humans and SIV infected rhesus macaques and has been shown to correlate with K/T ration in SIV infection. This is an excellent model to evaluate the compounds described here for the treatment of atherosclerosis, cardiovascular disease and vascular dementia.

The Materials and Methods are now described.

Generation of TG26$^{+/-}$ Apoe$^{-/-}$ Mice

Figure 16:
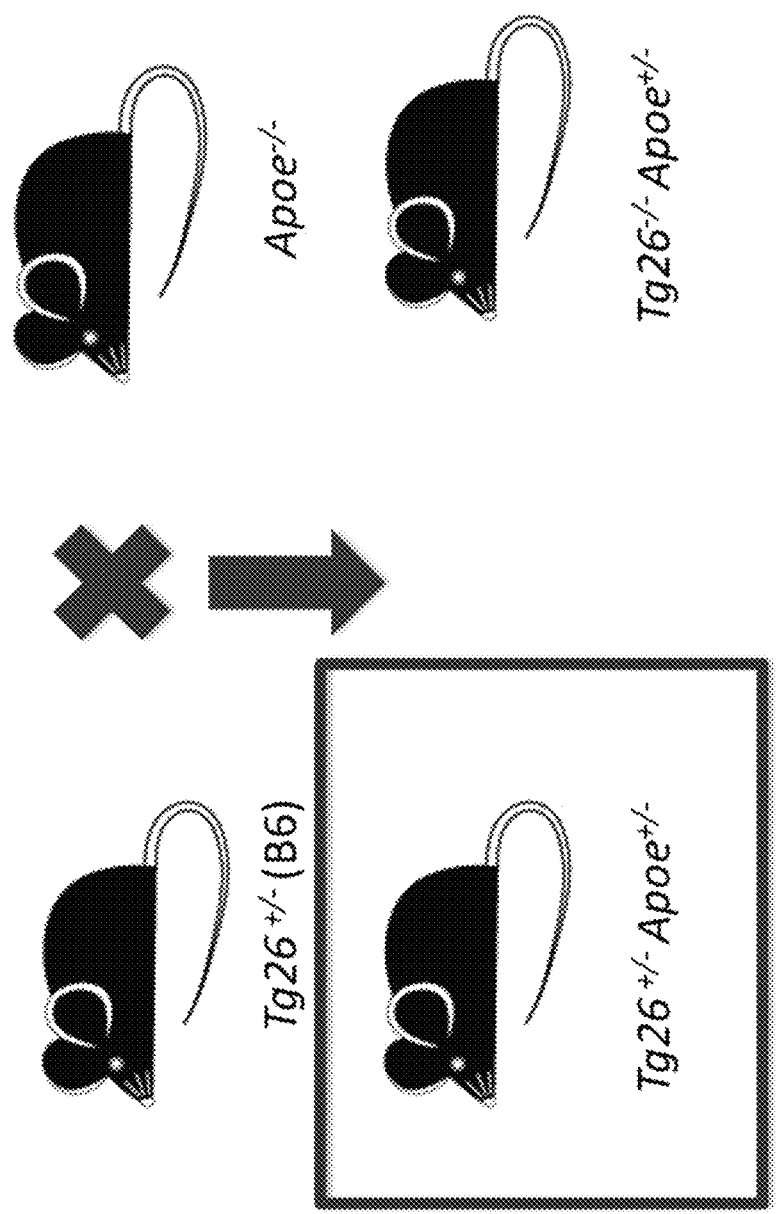
FIG. 16 depicts a diagram of the first step of the crossing strategy used to generate Tg26$^{+/-}$ Apoe$^{-/-}$ mice. Tg26$^{+/-}$ mice were crossed with Apoe$^{-/-}$ mice to generate Tg26$^{+/-}$ Apoe$^{+/-}$ mice.
Figure 17:
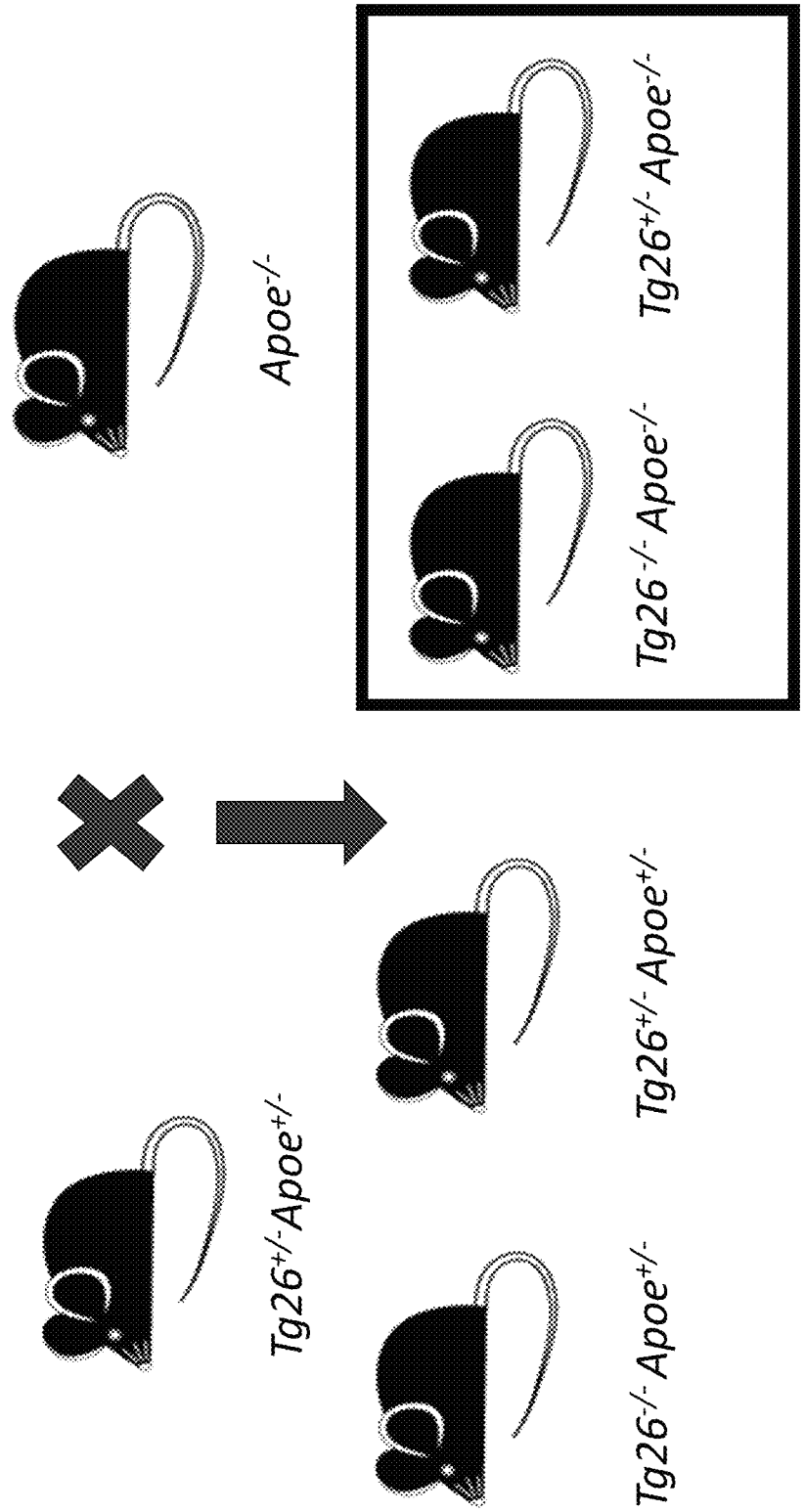
FIG. 17 depicts a diagram of the second step of the crossing strategy used to generate Tg26$^{+/-}$ Apoe$^{-/-}$ mice. Tg26$^{+/-}$ Apoe$^{+/-}$ mice were back crossed with Apoe$^{-/-}$ mice to generate Tg26$^{-/-}$ Apoe$^{-/-}$ and Tg26$^{+/-}$ Apoe$^{-/-}$ mice.
Figure 18:
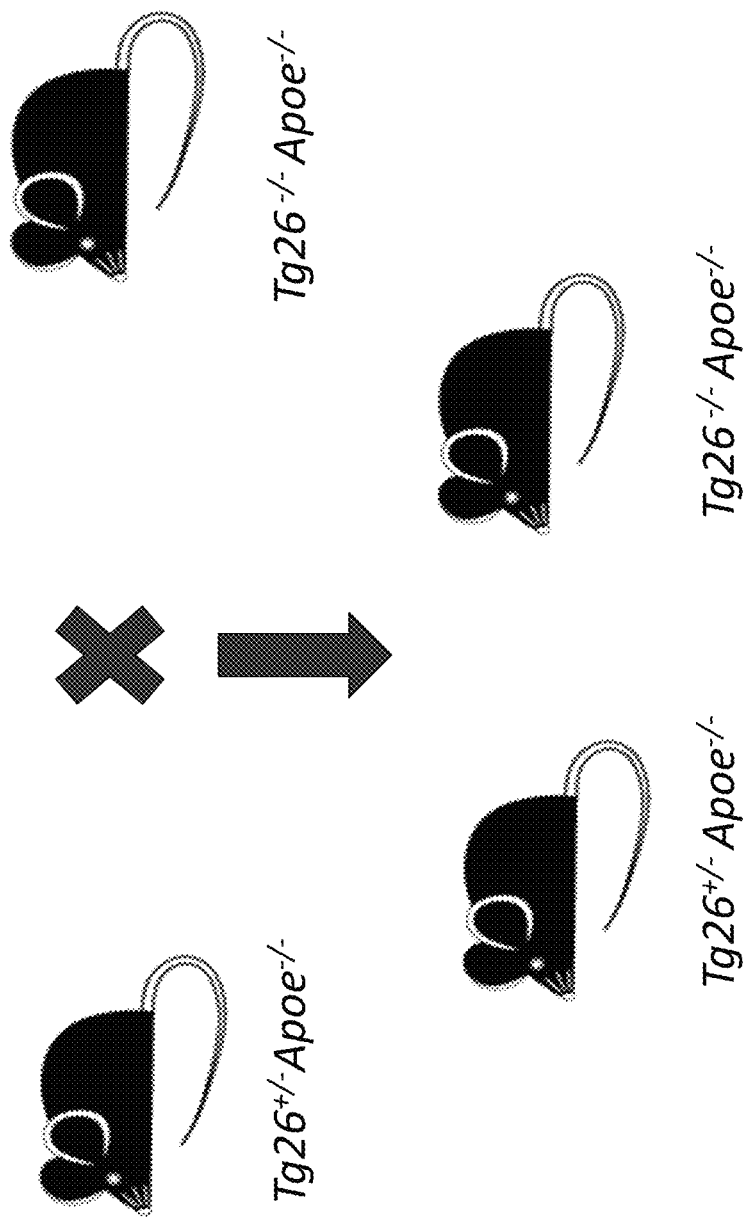
FIG. 18 depicts a diagram of the final step of the crossing strategy used to generate Tg26$^{+/-}$ Apoe$^{-/-}$ mice. A littermate comparison was performed to identify each mouse as Tg26$^{+/-}$ Apoe$^{-/-}$ or Tg26$^{-/-}$ Apoe$^{-/-}$.

Tg26$^{+/-}$ mice are from an infectious clone of an integrated virus pNL4-3 with in frame deletions of gag and pol sequences. Tg26$^{+/-}$ mice were first crossed with Apoe$^{-/-}$ mice according to the crossing strategy in FIG. 16 to generate Tg26$^{+/-}$ Apoe$^{+/-}$ mice. They were then back crossed with Apoe$^{-/-}$ mice according to the crossing strategy in FIG. 17 to generate Tg26$^{-/-}$ Apoe$^{-/-}$ and Tg26$^{+/-}$ Apoe$^{-/-}$ mice. A littermate comparison according to the crossing strategy in FIG. 18 was then performed to identify each mouse as Tg26$^{+/-}$ Apoe$^{-/-}$ or Tg26$^{-/-}$ Apoe$^{-/-}$.

Diet

Mice were fed a high fat diet having 20.1% saturated fat, 1.37% cholesterol, and 0% sodium cholate or a chow diet having 4-6% saturated fat and <0.2% cholesterol.

The Results of the Experiments are Now Described.

Figure 19:
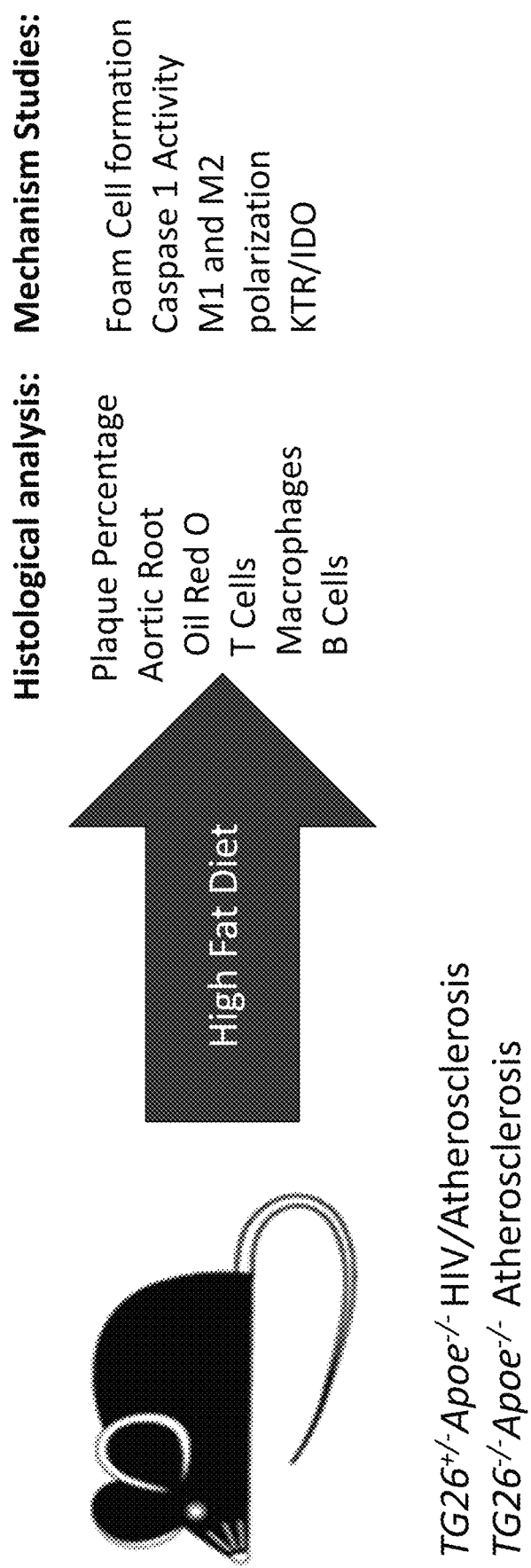
FIG. 19 depicts the experimental design used for the histological and mechanistic studies.

Tg26$^{-/-}$ Apoe$^{-/-}$ and Tg26$^{+/-}$ Apoe$^{-/-}$ mice fed a high fat were evaluated for using both histological analysis and mechanism studies (FIG. 19).

Figure 20:
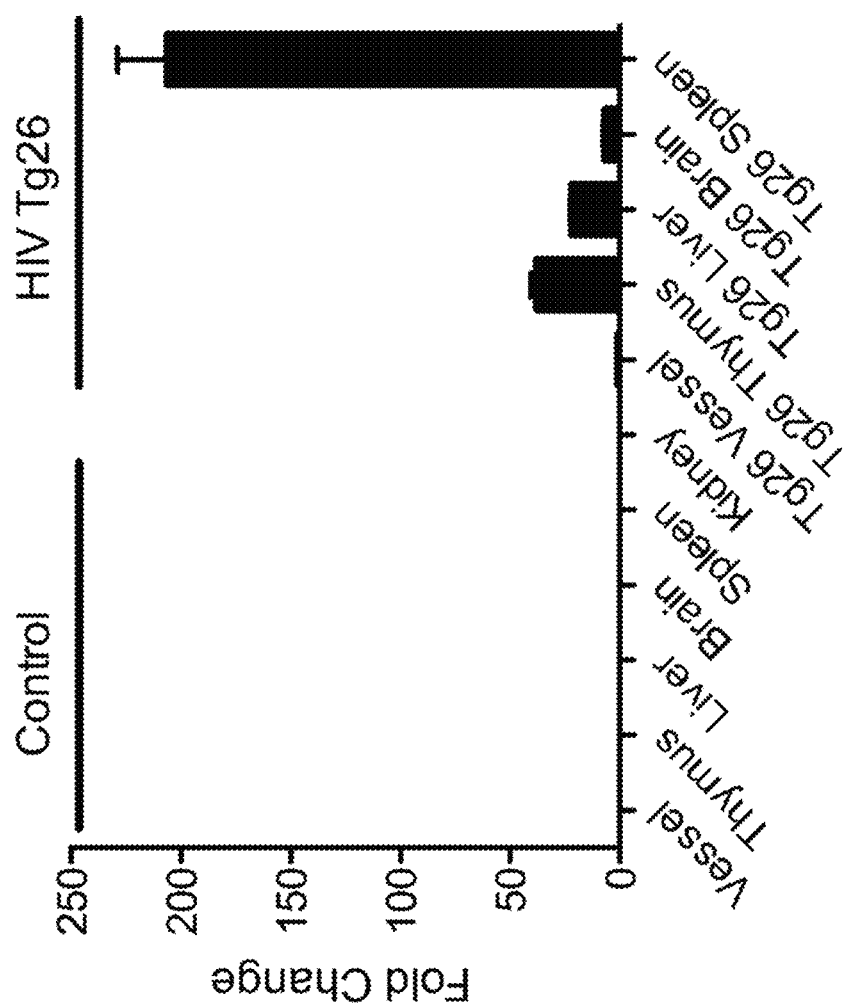
FIG. 20 depicts rt-PCR data for Tg26 mRNA expression in different tissues.
Figure 21:
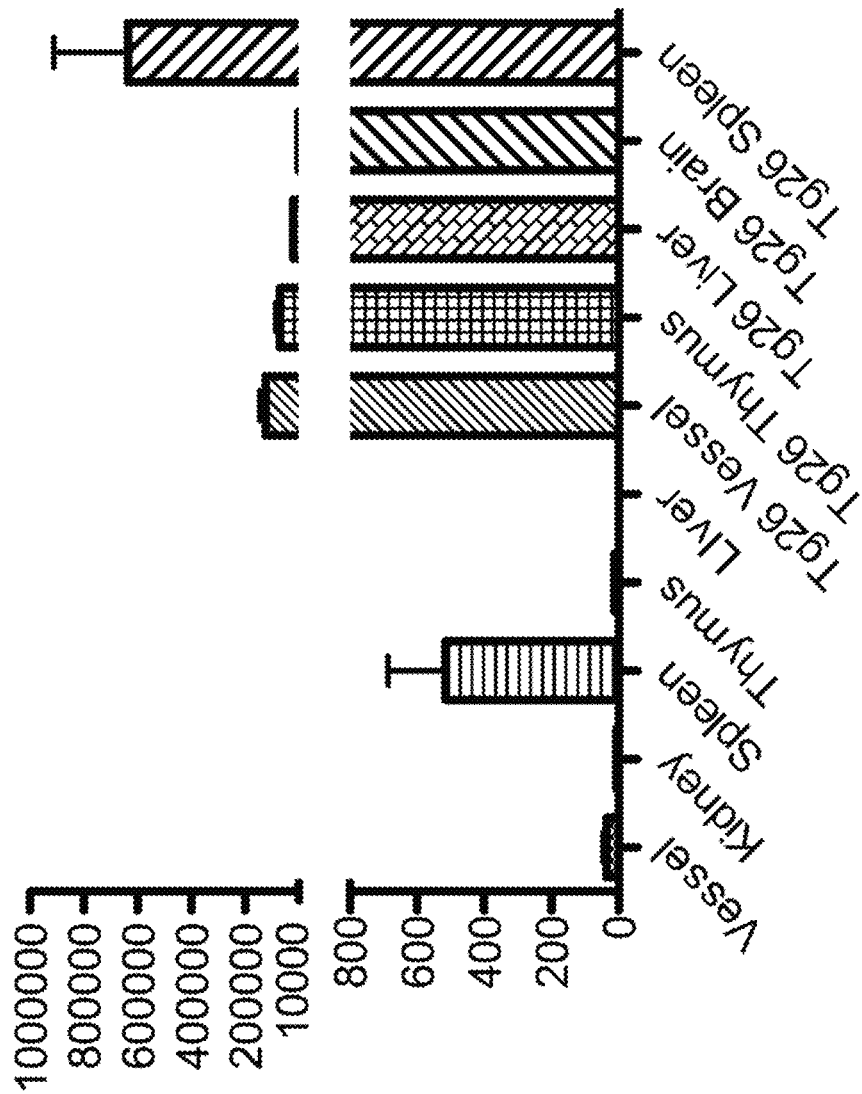
FIG. 21 depicts an evaluation of background expression in q-rt-pcr.

FIGS. 20 and 21 demonstrate the levels of HIV-1 mRNA in tissues from control and HIV Tg26 mice. Increased Tg26 mRNA was identified in all tissues from the HIV Tg26 mice, with the highest expression in the spleen. This models the expression patterns seen in HIV patients with tightly controlled viremia or HIV elite controllers.

Figures 22A, 22B:
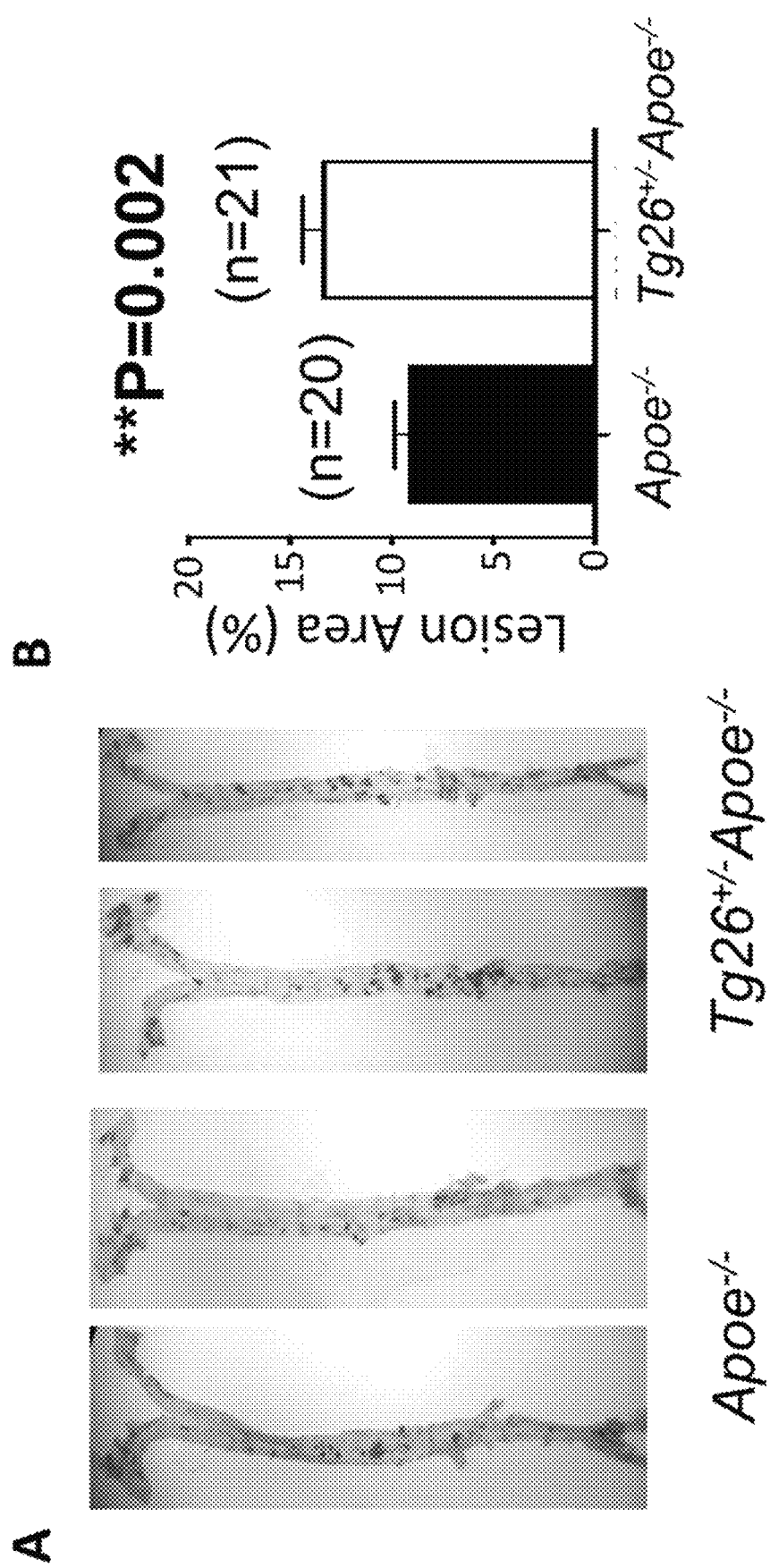
FIG. 22A and FIG. 22B, depicts an analysis of atherosclerotic lesion formation and size in Tg26$^{+/-}$ Apoe$^{-/-}$ and Tg26$^{-/-}$ Apoe$^{-/-}$ mice.

FIG. 22 demonstrates HIV-1 accelerates atherosclerosis in Tg26$^{+/-}$ Apoe$^{-/-}$ mice. Tg26$^{+/-}$ Apoe$^{-/-}$ mice showed a significant increase in lesion area as compared to Apoe$^{-/-}$ mice.

Figure 23:
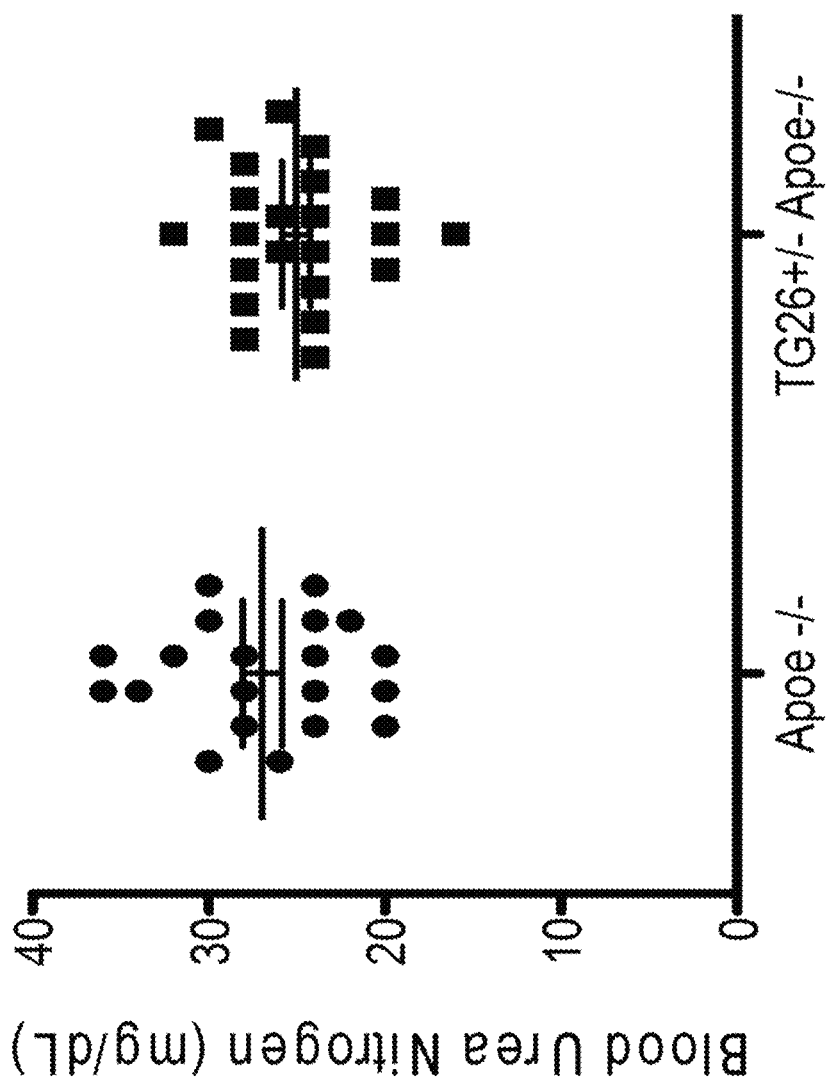
FIG. 23 depicts an analysis of blood urea nitrogen levels in Tg26$^{+/-}$ Apoe$^{-/-}$ and Tg26$^{-/-}$ Apoe$^{-/-}$ mice.
Figures 24A, 24B:
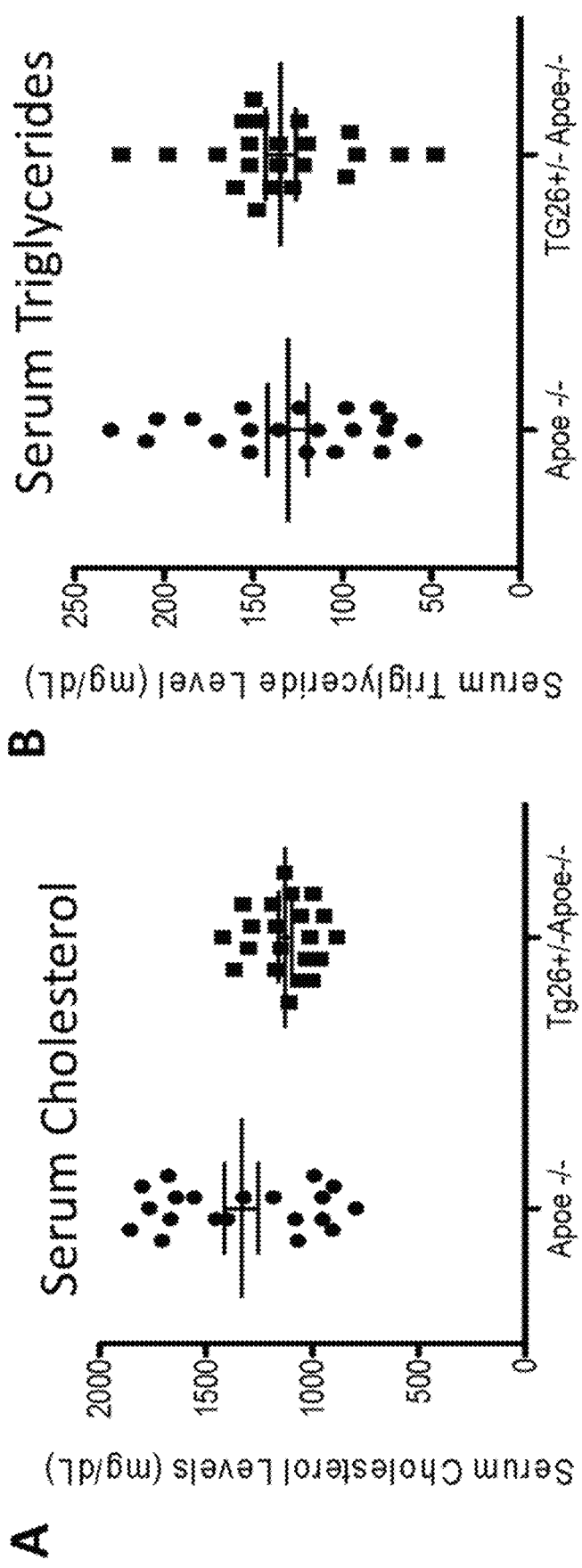
FIG. 24A and FIG. 24B, depicts an analysis of serum lipid content in Tg26$^{+/-}$ Apoe$^{-/-}$ and Tg26$^{-/-}$ Apoe$^{-/-}$ mice.

FIG. 23 demonstrates that there is no renal failure on B6 background. The blood urea nitrogen level of Tg26$^{+/-}$ Apoe$^{-/-}$ mice was not significantly different from the levels of Apoe$^{-/-}$ mice. Similarly, the lipid profiles of serum cholesterol (FIG. 24A) and serum triglycerides (FIG. 24B) Tg26$^{+/-}$ Apoe$^{-/-}$ mice was not significantly different from that of Apoe$^{-/-}$ mice.

Indoleamine-Pyrrole 2,3-Dioxygenase (IDO) and Tryptophan Metabolism

IDO is a key player in the pathogenesis of several inflammatory diseases including autoimmune disease, chronic infection, granulomatous disease, cancer and even atherosclerosis. The kynurenine to tryptophan ratio is augmented in patients with coronary artery disease (Wirleitner et al., Eur J Clin Invest. 2003 July; 33(7):550-4). The kynurenine to tryptophan ratio positively correlates with levels of the inflammation marker C-reactive protein and negatively with protective markers such as high-density lipoprotein cholesterol levels (Niinisalo et al., Scand J Clin Lab Invest. 2008; 68(8):767-70 and Pertovaara et al., Clin Exp Immunol. 2007 April; 148(1): 106-11). Kynurenine levels are associated with increased risk of acute myocardial infarction (Pedersen et al. Arterioscler Thromb Vasc Biol. 2015 February; 35(2):455-62). Increased IDO expression was also observed in the macrophage-rich cores of human atherosclerotic plaques (Niinisalo et al. Ann Med. 2010; 42(1):55-63) plaque percentage.

The kynurenine to tryptophan ratio is elevated in HIV-1 infected individuals (Huengsberg et al., Clin Chem. 1998 April; 44(4):858-62). HIV proteins Tat, nef, and gp41 have been reported to activate the kynurenine pathway in macrophages (Smith et al., J Neurovirol. 2001 February; 7(1): 56-60). Further, the kynurenine to tryptophan ratio is elevated in SIV models.

Figures 25A, 25B:
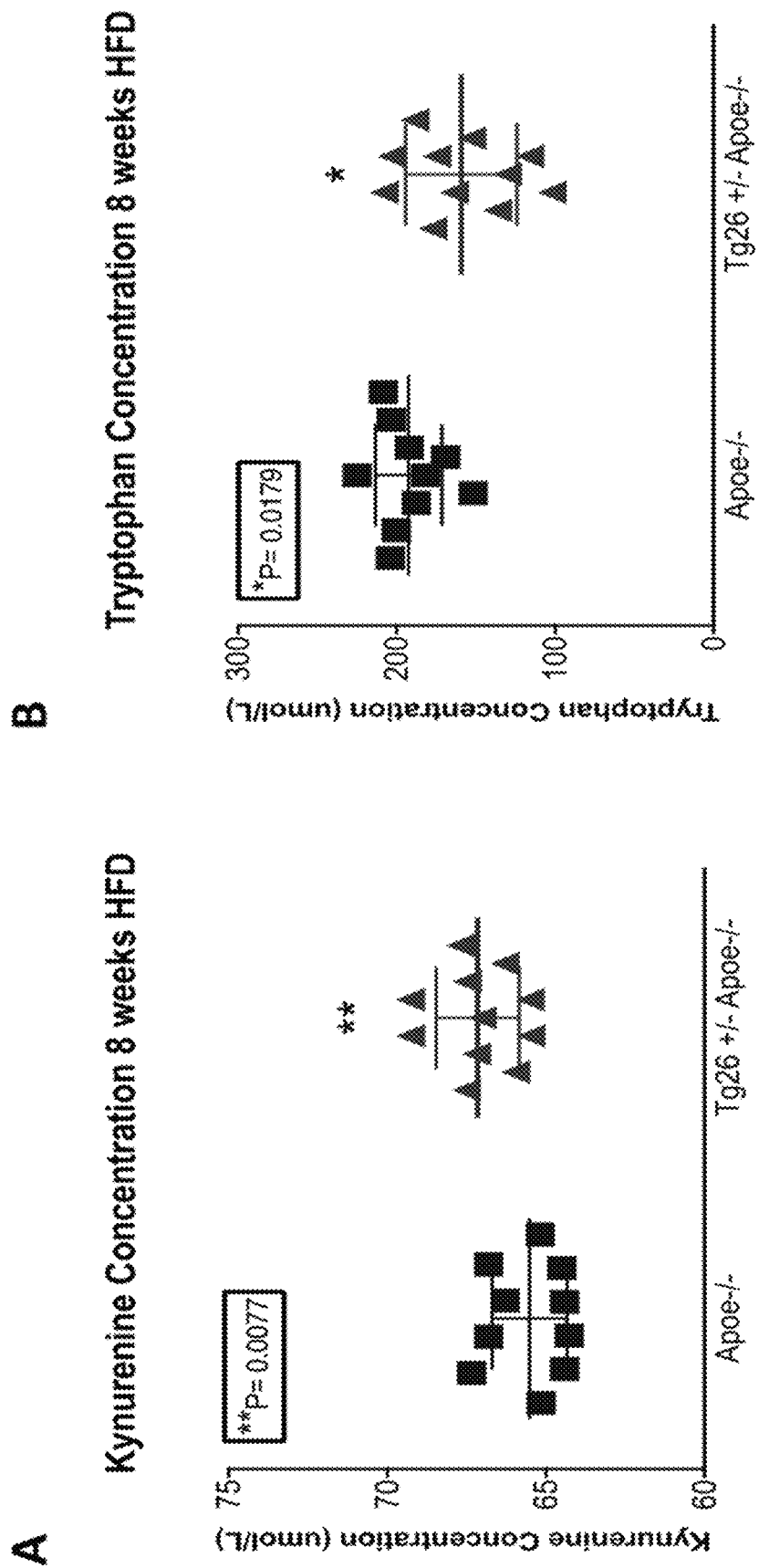
FIG. 25A and FIG. 25B, depicts an analysis of kynurenine and tryptophan concentrations after 8 weeks of high fat diet (HFD) in Tg26$^{+/-}$ Apoe$^{-/-}$ and Tg26$^{-/-}$ Apoe$^{-/-}$ mice.
Figure 26:
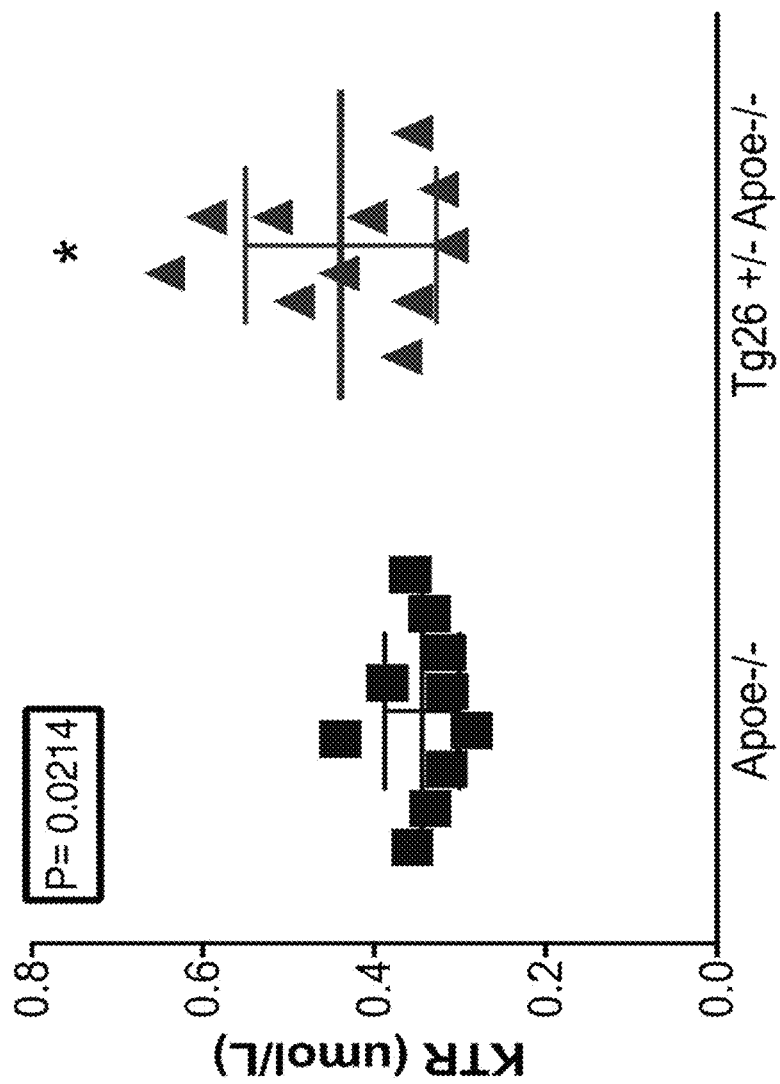
FIG. 26 depicts the kynurenine to tryptophan ratio in Tg26$^{+/-}$ Apoe$^{-/-}$ and Tg26$^{-/-}$ Apoe$^{-/-}$ mice.

$Tg26^{+/-}$ $Apoe^{-/-}$ mice showed a significant increase in kynurenine (FIG. 25A) and a significant decrease in tryptophan concentrations (FIG. 25B) as compared to $Apoe^{-/-}$ mice after 8 weeks of high fat diet (HFD). $Tg26^{+/-}$ $Apoe^{-/-}$ mice showed a significant increase in kynurenine to tryptophan ratio as compared to $Apoe^{-/-}$ mice (FIG. 26).

Figure 27:
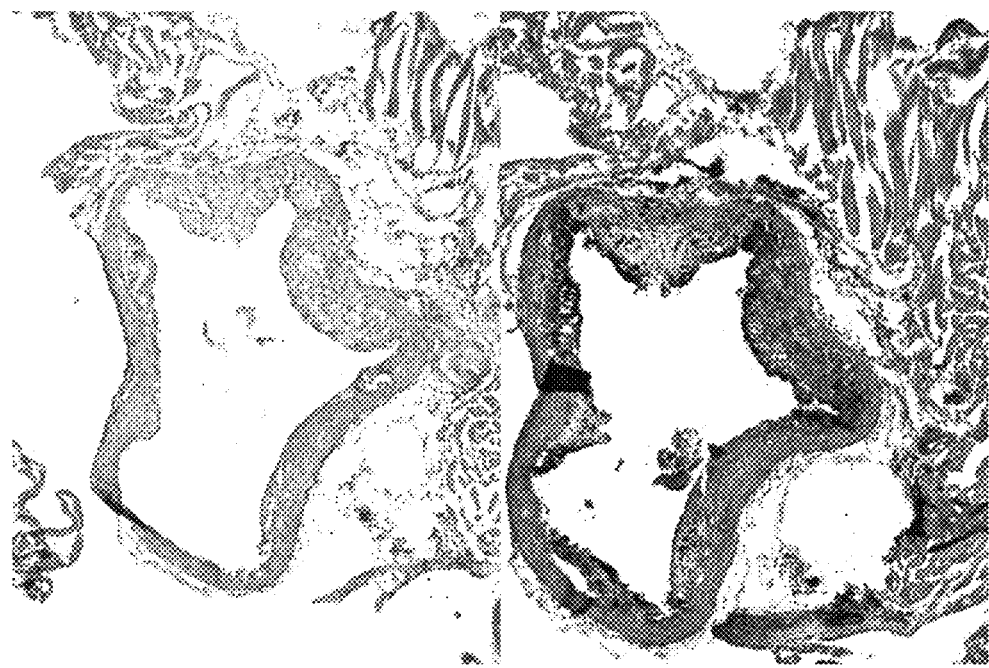
FIG. 27 depicts representative histological images of atherosclerotic lesions in Tg26$^{+/-}$ Apoe$^{-/-}$ and Tg26$^{-/-}$ Apoe$^{-/-}$ mice.
Figure 27:
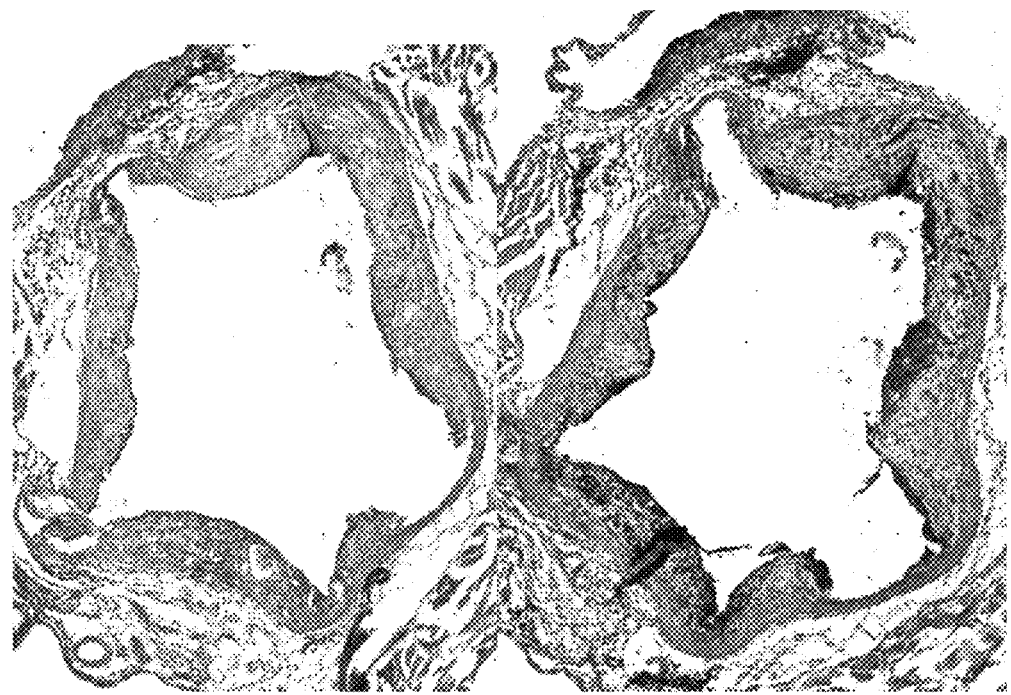
Figures 28A, 28B:
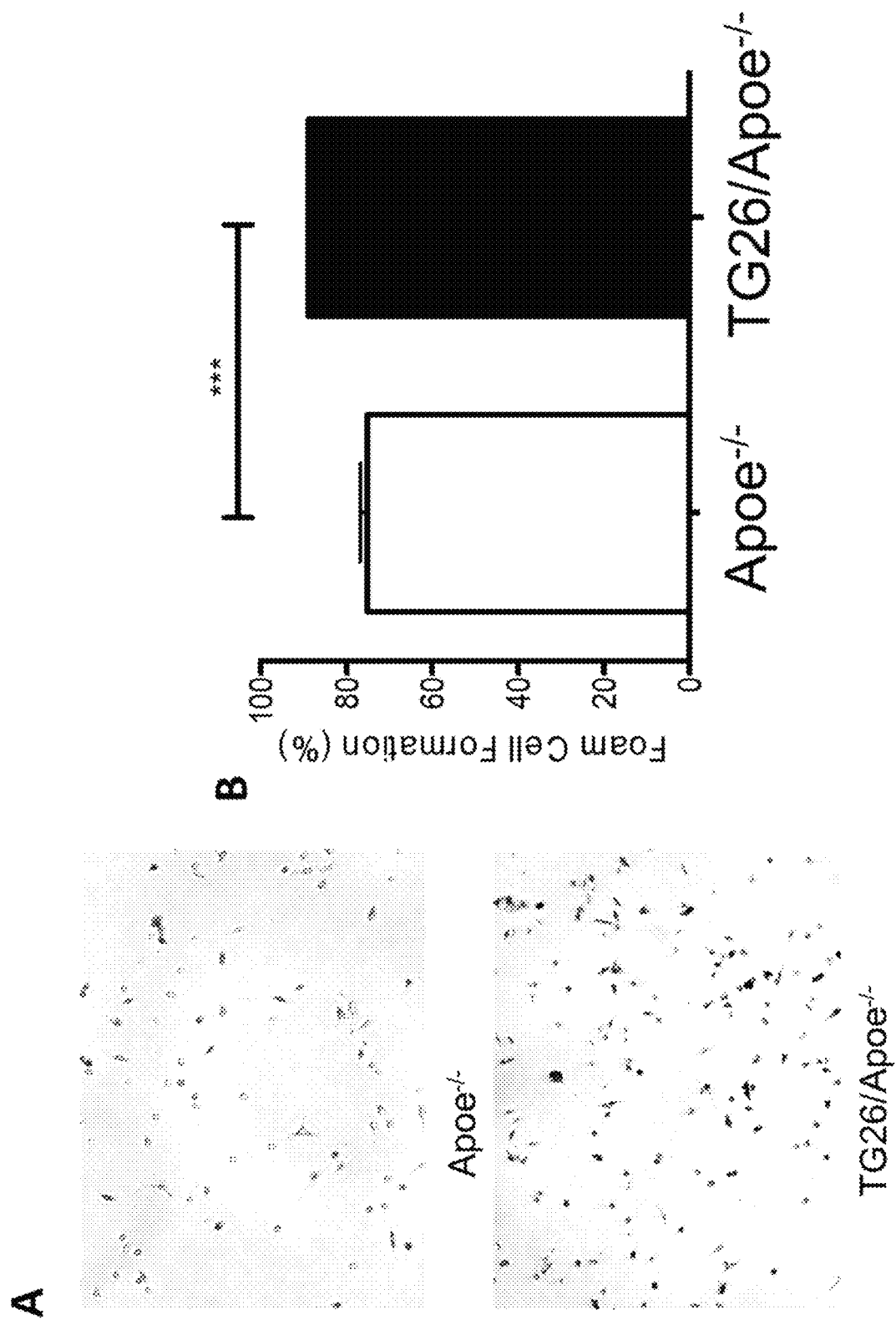
FIG. 28A and FIG. 28B, depicts an analysis of foam cell formation in Tg26$^{+/-}$ Apoe$^{-/-}$ and Tg26$^{-/-}$ Apoe$^{-/-}$ mice.

Histological analysis of atherosclerotic lesions revealed that the level of inflammatory infiltration was greater in $Tg26^{+/-}$ $Apoe^{-/-}$ mice as compared to $Apoe^{-/-}$ mice (FIG. 27). $Tg26^{+/-}$ $Apoe^{-/-}$ mice showed a significant increase in foam cell formation as compared to $Apoe^{-/-}$ mice (FIG. 28), indicating an increased level of plaque build-up, or atherosclerosis in the $Tg26^{+/-}$ $Apoe^{-/-}$ mice.

The experiments presented herein demonstrate that, similarly to what was seen in SIV infection, in a mouse model of HIV infection, tryptophan levels decrease and kynurenine levels increase. Further, it was demonstrated that the kynurenine to tryptophan ratio is increased in a mouse model of HIV infection. The similarities between the kynurenine to tryptophan ratio levels in the mouse model and what was seen in SIV suggests that NR treatment can be used to treat HIV infection and related comorbidities including, but not limited to atherosclerosis.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of modulating a kynurenine to tryptophan ratio in a subject in need thereof, the method comprising administering a composition comprising a nicotinamide adenine dinucleotide (NAD+) precursor to the subject,
    wherein the composition comprising the NAD+ precursor modulates the kynurenine to tryptophan ratio in the subject;
    wherein the NAD+ precursor is administered in combination with an indoleamine 2,3-dioxygenase (IDO) antagonist.

2. The method of claim 1, wherein the NAD+ precursor is a nicotinamide riboside.

3. The method of claim 1, wherein the subject has a disease selected from the group consisting of a disease having an immunosuppressive character, viral infections, human immunodeficiency virus (HIV) infection, hepatitis C virus (HCV) infection, bacterial infections, parasitic infections, comorbidities of viral infections, cancers, neurodegenerative diseases or disorders, immune-mediated disorders, inflammatory diseases, cardiovascular diseases, kidney diseases, autoimmune diseases, lupus, systemic lupus erythematosus, age-related disorders, diabetes, obesity, insulin resistance, eating disorders, metabolic syndrome, pain, migraine, rheumatoid arthritis, osteoporosis, sleep disorders, mood disorders, psychiatric diseases or disorders, neurologic diseases or disorders, depression, schizophrenia, Alzheimer disease and Parkinson's Disease.

4. A method of treating a disease in a subject, the method comprising modulating the kynurenine to tryptophan ratio in the subject,
    wherein the method comprises administering a composition comprising a NAD+ precursor to the subject;
    wherein the composition comprising the NAD+ precursor modulates the kynurenine to tryptophan ratio in the subject;
    wherein the NAD+ precursor is administered in combination with an indoleamine 2,3 dioxygenase (IDO) antagonist; and
    wherein the disease is selected from the group consisting of a disease having an immunosuppressive character, viral infections, human immunodeficiency virus (HIV) infection, and comorbidities of viral infections.

* * * * *